United States Patent
Bhatia et al.

(10) Patent No.: US 11,021,529 B2
(45) Date of Patent: Jun. 1, 2021

(54) ANTIMICROBIAL CONSTRUCTS AND USES THEREOF

(71) Applicant: Massachusetts Institute of Technology, Cambridge, MA (US)

(72) Inventors: Sangeeta N. Bhatia, Lexington, MA (US); Ester Jihae Kwon, Cambridge, MA (US); Leslie W. Chan, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/909,006

(22) Filed: Mar. 1, 2018

(65) Prior Publication Data

US 2018/0371059 A1    Dec. 27, 2018

Related U.S. Application Data

(60) Provisional application No. 62/467,058, filed on Mar. 3, 2017.

(51) Int. Cl.
| | | |
|---|---|---|
| *C07K 14/79* | (2006.01) | |
| *A61K 47/64* | (2017.01) | |
| *C07K 7/06* | (2006.01) | |
| *C07K 14/47* | (2006.01) | |
| *B82Y 5/00* | (2011.01) | |

(52) U.S. Cl.
CPC .............. *C07K 14/79* (2013.01); *A61K 47/64* (2017.08); *A61K 47/644* (2017.08); *B82Y 5/00* (2013.01); *C07K 7/06* (2013.01); *C07K 14/4723* (2013.01)

(58) Field of Classification Search
None
See application file for complete search history.

(56) References Cited

U.S. PATENT DOCUMENTS

| | | |
|---|---|---|
| 8,071,540 B2 | 12/2011 | Montelaro et al. |
| 8,106,040 B2 | 1/2012 | Gao et al. |
| 8,821,933 B2 | 9/2014 | Yeoman et al. |
| 9,034,380 B2 | 5/2015 | Rademacher et al. |
| 2003/0171281 A1 | 9/2003 | Krieger et al. |
| 2004/0019181 A1 | 1/2004 | Falla et al. |
| 2013/0237476 A1 | 9/2013 | Hulvat |
| 2014/0005379 A1 | 1/2014 | Gu |
| 2015/0231274 A1 | 8/2015 | Cheng et al. |

FOREIGN PATENT DOCUMENTS

| | | |
|---|---|---|
| WO | 2000042973 A2 | 7/2000 |
| WO | 2012069089 A1 | 5/2012 |
| WO | 2015181138 A1 | 12/2015 |

OTHER PUBLICATIONS

Alves et al. "A proapoptotic peptide conjugated to penetratin selectively inhibits tumor cell growth" Biochimica et Biophysica Acta 1838:2087-2098. (Year: 2014).*
Durzynska et al. "Viral and Other Cell-Penetrating Peptides as Vectors of Therapeutic Agents in Medicine" J. Pharmacology and Experimental Therapeutics 354:32-42. (Year: 2015).*
McGrath et al. "Mechanism of action and initial evaluation of a membrane active all-D-enantiomer antimicrobial peptidomimetic" Proceedings of the National Academy of Science 110:3477-3482. (Year: 2013).*
Naidu et al. "Lactoferrin interaction with salmonellae potentiates antibiotic susceptibility in vitro" Diagnostic Microbiology and Infectious Disease 20:69-75. (Year: 1994).*
Bruni et al. "Antimicrobial Activity of Lactoferrin-Related Peptides and Applications in Human and Veterinary Medicine" Molecules 21,752. (Year: 2016).*
Pushpanathan, M. et al. "Antimicrobial Peptides: Versatile Biological Properties," Hindawi Publishing Corporation, International Journal of Peptides, vol. 2013, Article ID 675391, 15 pages (2013).
Reinhardt, A. et al., "Design and Application of Antimicrobial Peptide Conjugates," Int. J. Mol. Sci., vol. 17(701) 21 pages (2016).
Sun, G. et al., "Engineering dextran-based scaffolds for drug delivery and tissue repair," Nanomedicine (Lond)., vol. 7(11): 1771-1784 (2012).
Dutot, L. et al., "Glycosylated cell-penetrating peptides and their conjugates to a proapoptotic peptide: preparation by click chemistry and cell viability studies", J. Chem. Biol., vol. 3(2) 51-65 (2009).
Fowler, C. et al., "MICs of rifampicin and chloramphenicol for mucoid Pseudomonas aeruginosa strains are lower when human lactoferrin is present", Journal of Antimicrobial Chemotherapy, vol. 40(6) 877-879 (1997).
International Search Report and Written Opinion, PCT/US2018/020372, dated Jun. 6, 2018, 16 pages.
Kwon, E. et al., "Porous Silicon Nanoparticle Delivery of Tandem Peptide Anti-Infectives for the Treatment of Pseudomonas aeruginosa Lung Infections", Advance Materials, vol. 29(35) 1701527 (2017).
Law, B. et al., "A mitochondrial targeted fusion peptide exhibits remarkable cytotoxicity", Mol. Cancer Ther., vol. 5(8), 1944-1949 (2006).
Liu, D. et al., "Co-delivery of a hydrophobic small molecule and a hydrophilic peptide by porous silicon nanoparticles", Journal of Controlled Release, vol. 170(2) 268-278 (2013).
Naidu, A.S. et al., "Lactoferrin Interaction with Salmonellae Potentiates Antibiotic Susceptibility in vitro", Diagn. Microbiol. Infect Dis., vol. 20(2) 69-75 (1994).

(Continued)

*Primary Examiner* — Sudhakar Katakam
*Assistant Examiner* — Zachary J Miknis
(74) *Attorney, Agent, or Firm* — Nelson Mullins Riley & Scarborough LLP; Amy E. Mandragouras, Esq.; Ariana D. Harris

(57) ABSTRACT

Disclosed herein are antimicrobial constructs comprising a membrane interacting peptide and an antimicrobial agent. Also disclosed are methods for making and using the constructs.

19 Claims, 23 Drawing Sheets
(20 of 23 Drawing Sheet(s) Filed in Color)
Specification includes a Sequence Listing.

(56) References Cited

OTHER PUBLICATIONS

Nordstrom, R. et al., "Delivery systems for antimicrobial peptides", Advances in Colloid and Interface Science, vol. 242, 17-34 (2017).
The International Preliminary report on Patentability issued in International Application No. PCT/US2018/020372, dated Sep. 12, 2019 (11 pages).

* cited by examiner

FIG. 5A
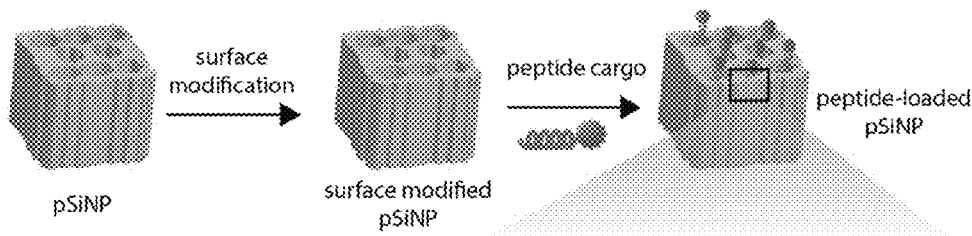
FIG. 5B
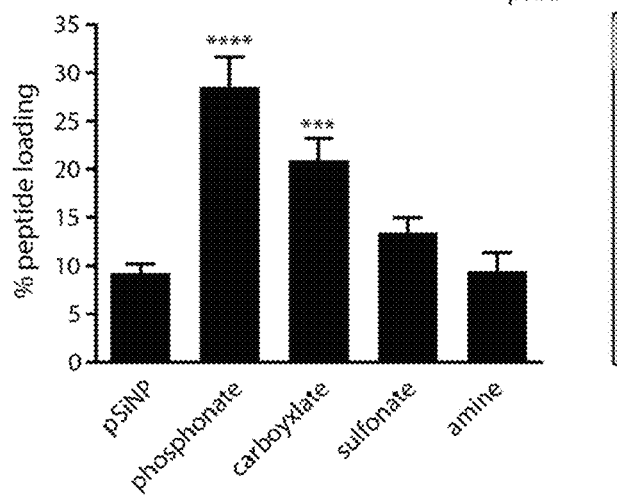
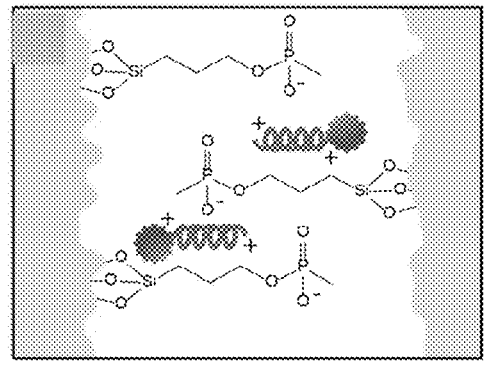
FIG. 5C
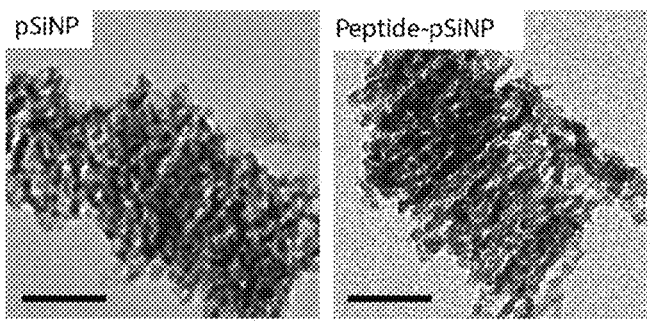
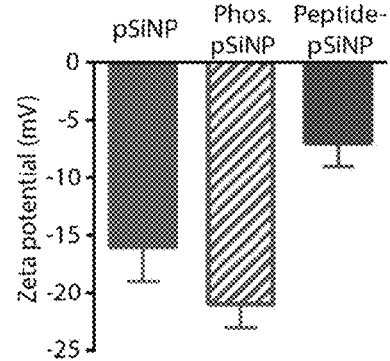
FIG. 5D
FIG. 5E FIG. 9A
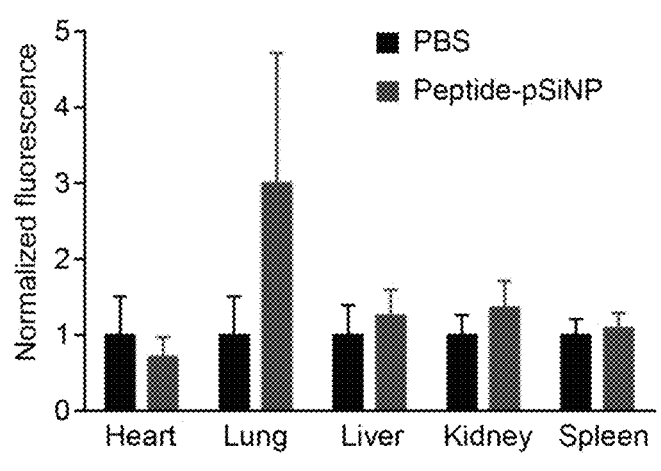
FIG. 9B
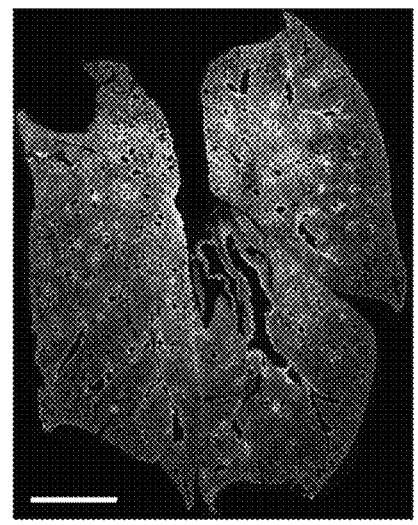
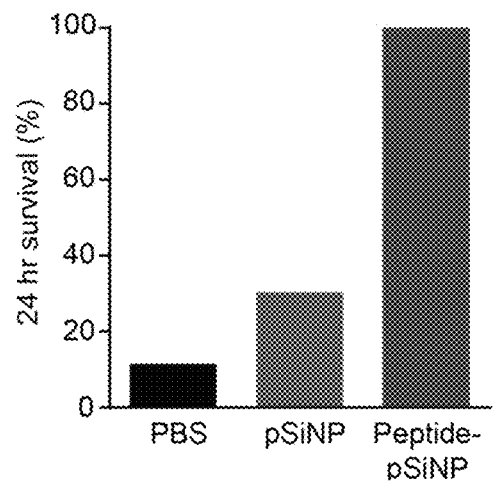
FIG. 9C
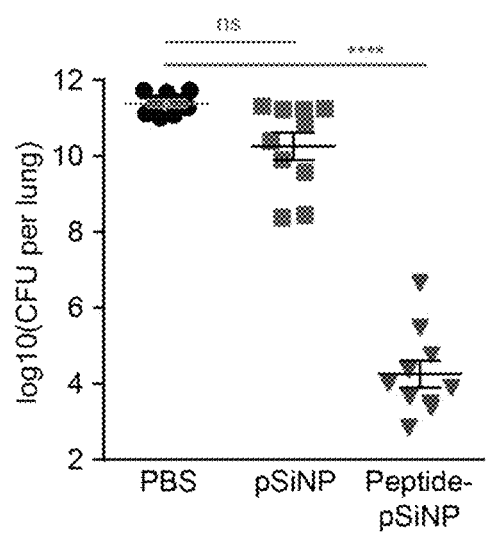
FIG. 9D

FIG. 10A
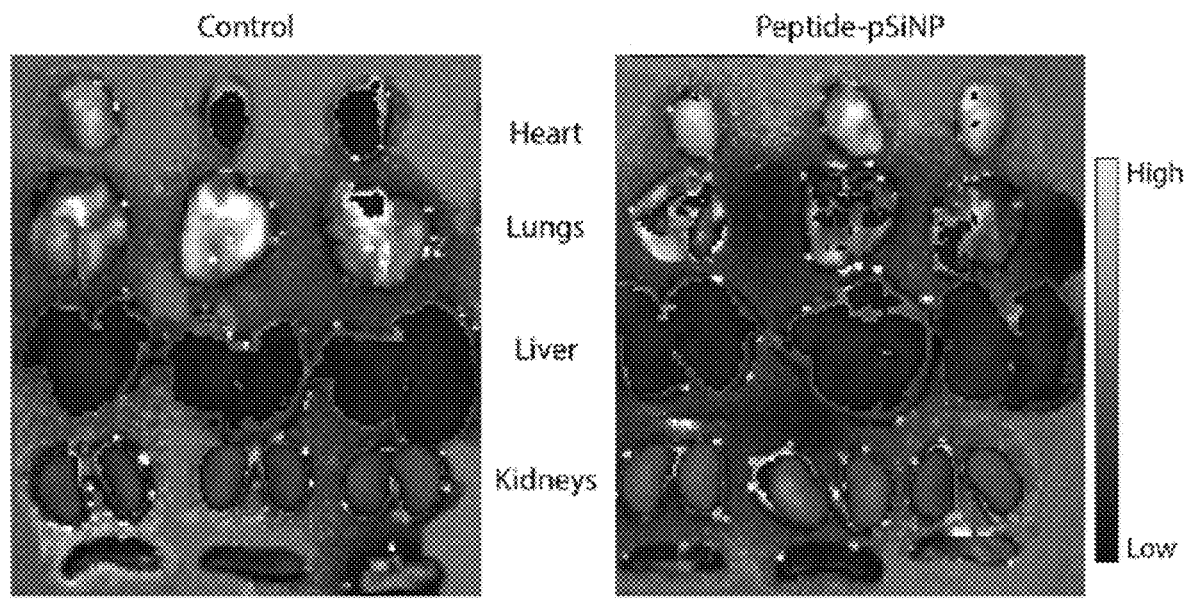
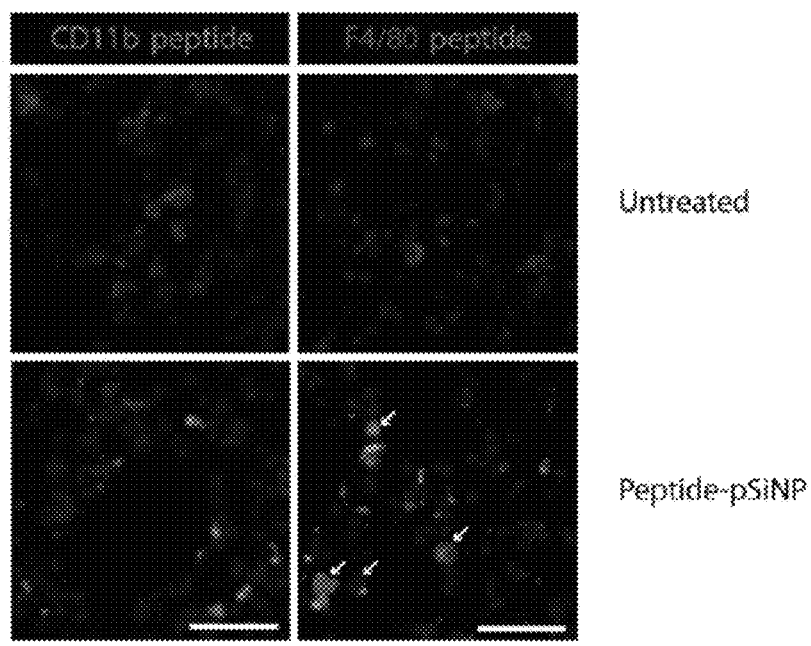
FIG. 10B

SEQUENCE LISTING

<160> NUMBER OF SEQ ID NOS: 39

<210> SEQ ID NO 1
<211> LENGTH: 22
<212> TYPE: PRT
<213> ORGANISM: Artificial Sequence
<220> FEATURE:
<223> OTHER INFORMATION: Synthetic: Lactoferrin-derived peptide

<400> SEQUENCE: 1

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 2
<211> LENGTH: 711

```
<212> TYPE: PRT
<213> ORGANISM: Homo sapiens
<220> FEATURE:
<221> NAME/KEY: misc_feature
<223> OTHER INFORMATION: Human lactoferrin

<400> SEQUENCE: 2
```

Met Lys Leu Val Phe Leu Val Leu Leu Phe Leu Gly Ala Leu Gly Leu
1               5                   10                  15

Cys Leu Ala Gly Arg Arg Arg Arg Ser Val Gln Trp Cys Ala Val Ser
            20                  25                  30

Gln Pro Glu Ala Thr Lys Cys Phe Gln Trp Gln Arg Asn Met Arg Arg
        35                  40                  45

Val Arg Gly Pro Pro Val Ser Cys Ile Lys Arg Asp Ser Pro Ile Gln
50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Asn Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
        355                 360                 365

Ala Val Gly Glu Gln Glu Leu Arg Lys Cys Asn Gln Trp Ser Gly Leu
    370                 375                 380

```
Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
            405                 410                 415

Gly Tyr Val Tyr Thr Ala Gly Lys Cys Gly Leu Val Pro Val Leu Ala
        420                 425                 430

Glu Asn Tyr Lys Ser Gln Gln Ser Ser Asp Pro Asp Pro Asn Cys Val
    435                 440                 445

Asp Arg Pro Val Glu Gly Tyr Leu Ala Val Ala Val Val Arg Arg Ser
450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
530                 535                 540

Tyr Tyr Gly Tyr Thr Gly Ala Phe Arg Cys Leu Ala Glu Asp Ala Gly
545                 550                 555                 560

Asp Val Ala Phe Val Lys Gly Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
690                 695                 700

Ala Cys Glu Phe Leu Arg Lys
705                 710

<210> SEQ ID NO 3
<211> LENGTH: 20
<212> TYPE: PRT
<213> ORGANISM: Artificial Sequence
<220> FEATURE:
<223> OTHER INFORMATION: Synthetic: S413-PV

<400> SEQUENCE: 3

Ala Leu Trp Lys Thr Leu Leu Lys Lys Val Leu Lys Ala Pro Lys Lys
1               5                   10                  15

Lys Arg Lys Val
            20
```

```
<210> SEQ ID NO 4
<211> LENGTH: 26
<212> TYPE: PRT
<213> ORGANISM: Artificial Sequence
<220> FEATURE:
<223> OTHER INFORMATION: Synthetic: CecroA+Mel

<400> SEQUENCE: 4

Lys Trp Lys Leu Phe Lys Lys Ile Gly Ile Gly Ala Val Leu Lys Val
1               5                   10                  15

Leu Thr Thr Gly Leu Pro Ala Leu Ile Ser
            20                  25

<210> SEQ ID NO 5
<211> LENGTH: 21
<212> TYPE: PRT
<213> ORGANISM: Artificial Sequence
<220> FEATURE:
<223> OTHER INFORMATION: Synthetic: Buforin 2

<400> SEQUENCE: 5

Thr Arg Ser Ser Arg Ala Gly Leu Gln Phe Pro Val Gly Arg Val His
1               5                   10                  15

Arg Leu Leu Arg Lys
            20

<210> SEQ ID NO 6
<211> LENGTH: 23
<212> TYPE: PRT
<213> ORGANISM: Artificial Sequence
<220> FEATURE:
<223> OTHER INFORMATION: Synthetic: Magainin

<400> SEQUENCE: 6

Gly Ile Gly Lys Trp Leu His Ser Ala Lys Lys Phe Gly Lys Ala Phe
1               5                   10                  15

Val Gly Glu Ile Met Asn Ser
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic: Pep1

<400> SEQUENCE: 7

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 8
<211> LENGTH: 26
<212> TYPE: PRT
<213> ORGANISM: Artificial Sequence
<220> FEATURE:
<223> OTHER INFORMATION: Synthetic: Melittin

<400> SEQUENCE: 8

Gly Ile Gly Ala Val Leu Lys Val Leu Thr Thr Gly Leu Pro Ala Leu
1               5                   10                  15

Ile Ser Trp Ile Lys Arg Lys Arg Gln Gln
```

```
                20                  25

<210> SEQ ID NO 9
<211> LENGTH: 30
<212> TYPE: PRT
<213> ORGANISM: Artificial Sequence
<220> FEATURE:
<223> OTHER INFORMATION: Synthetic: GALA

<400> SEQUENCE: 9

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 10
<211> LENGTH: 18
<212> TYPE: PRT
<213> ORGANISM: Artificial Sequence
<220> FEATURE:
<223> OTHER INFORMATION: Synthetic: Apidaecins

<400> SEQUENCE: 10

Gly Asn Asn Arg Pro Val Tyr Ile Pro Gln Pro Arg Pro Pro His Pro
1               5                   10                  15

Arg Leu

<210> SEQ ID NO 11
<211> LENGTH: 12
<212> TYPE: PRT
<213> ORGANISM: Artificial Sequence
<220> FEATURE:
<223> OTHER INFORMATION: Synthetic: Tat

<400> SEQUENCE: 11

Tyr Gly Arg Lys Lys Arg Arg Gln Arg Arg Arg Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic: KFFKFFKFFK

<400> SEQUENCE: 12

Lys Phe Phe Lys Phe Phe Lys Phe Phe Lys
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Synthetic: YTA4

<400> SEQUENCE: 13

Ile Ala Trp Val Lys Ala Phe Ile Arg Lys Leu Arg Lys Gly Pro Leu
1               5                   10                  15

Gly

<210> SEQ ID NO 14
<211> LENGTH: 22
<212> TYPE: PRT
<213> ORGANISM: Artificial Sequence
```

```
<220> FEATURE:
<223> OTHER INFORMATION: Synthetic: M918

<400> SEQUENCE: 14

Met Val Thr Val Leu Phe Arg Arg Leu Arg Ile Arg Arg Ala Cys Gly
1               5                   10                  15

Pro Pro Arg Val Arg Val
            20

<210> SEQ ID NO 15
<211> LENGTH: 16
<212> TYPE: PRT
<213> ORGANISM: Artificial Sequence
<220> FEATURE:
<223> OTHER INFORMATION: Synthetic: Penetratin

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 34
<212> TYPE: PRT
<213> ORGANISM: Artificial Sequence
<220> FEATURE:
<223> OTHER INFORMATION: Synthetic: VP22

<400> SEQUENCE: 16

Asn Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Gln

<210> SEQ ID NO 17
<211> LENGTH: 24
<212> TYPE: PRT
<213> ORGANISM: Artificial Sequence
<220> FEATURE:
<223> OTHER INFORMATION: Synthetic: HGP

<400> SEQUENCE: 17

Leu Leu Gly Arg Arg Gly Trp Glu Val Leu Lys Tyr Trp Trp Asn Leu
1               5                   10                  15

Leu Gln Tyr Trp Ser Gln Glu Leu
            20

<210> SEQ ID NO 18
<211> LENGTH: 24
<212> TYPE: PRT
<213> ORGANISM: Artificial Sequence
<220> FEATURE:
<223> OTHER INFORMATION: Synthetic: Bac7

<400> SEQUENCE: 18

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 19
<211> LENGTH: 6
<212> TYPE: PRT
<213> ORGANISM: Artificial Sequence
```

```
<220> FEATURE:
<223> OTHER INFORMATION: Synthetic: 6R

<400> SEQUENCE: 19

Arg Arg Arg Arg Arg Arg
1               5

<210> SEQ ID NO 20
<211> LENGTH: 22
<212> TYPE: PRT
<213> ORGANISM: Artificial Sequence
<220> FEATURE:
<223> OTHER INFORMATION: Synthetic: HuT-cell CPP

<400> SEQUENCE: 20

Tyr Ala Arg Val Arg Arg Arg Gly Pro Arg Gly Tyr Ala Arg Val Arg
1               5                   10                  15

Arg Arg Gly Pro Arg Arg
            20

<210> SEQ ID NO 21
<211> LENGTH: 18
<212> TYPE: PRT
<213> ORGANISM: Artificial Sequence
<220> FEATURE:
<223> OTHER INFORMATION: Synthetic: pVEC

<400> SEQUENCE: 21

Leu Leu Ile Ile Leu Arg Arg Arg Ile Arg Lys Gln Ala His Ala His
1               5                   10                  15

Ser Lys

<210> SEQ ID NO 22
<211> LENGTH: 20
<212> TYPE: PRT
<213> ORGANISM: Artificial Sequence
<220> FEATURE:
<223> OTHER INFORMATION: Synthetic: CADY

<400> SEQUENCE: 22

Gly Leu Trp Arg Ala Leu Trp Arg Leu Leu Arg Ser Leu Trp Arg Leu
1               5                   10                  15

Leu Trp Arg Ala
            20

<210> SEQ ID NO 23
<211> LENGTH: 18
<212> TYPE: PRT
<213> ORGANISM: Artificial Sequence
<220> FEATURE:
<223> OTHER INFORMATION: Synthetic: MAP

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 12
<212> TYPE: PRT
<213> ORGANISM: Artificial Sequence
<220> FEATURE:
<223> OTHER INFORMATION: Synthetic: LBU1

<400> SEQUENCE: 24
```

```
Arg Val Val Arg Val Val Arg Arg Val Arg Arg
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic: WLBU1

<400> SEQUENCE: 25

Arg Val Val Arg Val Val Arg Arg Trp Val Arg Arg
1               5                   10

<210> SEQ ID NO 26
<211> LENGTH: 24
<212> TYPE: PRT
<213> ORGANISM: Artificial Sequence
<220> FEATURE:
<223> OTHER INFORMATION: Synthetic: LBU2

<400> SEQUENCE: 26

Arg Arg Val Val Arg Arg Val Arg Arg Val Val Arg Arg Val Val Arg
1               5                   10                  15

Val Val Arg Arg Val Val Arg Arg
            20

<210> SEQ ID NO 27
<211> LENGTH: 24
<212> TYPE: PRT
<213> ORGANISM: Artificial Sequence
<220> FEATURE:
<223> OTHER INFORMATION: Synthetic: WLBU2

<400> SEQUENCE: 27

Arg Arg Trp Val Arg Arg Val Arg Arg Trp Val Arg Arg Val Val Arg
1               5                   10                  15

Val Val Arg Arg Trp Val Arg Arg
            20

<210> SEQ ID NO 28
<211> LENGTH: 9
<212> TYPE: PRT
<213> ORGANISM: Artificial Sequence
<220> FEATURE:
<223> OTHER INFORMATION: Synthetic: P9b

<400> SEQUENCE: 28

Gln Arg Lys Leu Ala Ala Lys Leu Thr
1               5

<210> SEQ ID NO 29
<211> LENGTH: 33
<212> TYPE: PRT
<213> ORGANISM: Artificial Sequence
<220> FEATURE:
<223> OTHER INFORMATION: Synthetic: P9b-WLBU2 tandem peptide

<400> SEQUENCE: 29

Gln Arg Lys Leu Ala Ala Lys Leu Thr Arg Arg Trp Val Arg Arg Val
1               5                   10                  15

Arg Arg Trp Val Arg Arg Val Val Arg Val Val Arg Arg Trp Val Arg
            20                  25                  30

Arg
```

```
<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

Lys Leu Ala Lys Leu Ala Lys Lys Leu Ala Lys Leu Ala Lys
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic

<400> SEQUENCE: 31

Lys Leu Ala Lys Lys Leu Ala Lys Leu Ala Lys Lys Leu Ala
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic

<400> SEQUENCE: 32

Lys Ala Ala Lys Lys Ala Ala Lys Ala Ala Lys Lys Ala Ala
1               5                   10

<210> SEQ ID NO 33
<211> LENGTH: 21
<212> TYPE: PRT
<213> ORGANISM: Artificial Sequence
<220> FEATURE:
<223> OTHER INFORMATION: Synthetic

<400> SEQUENCE: 33

Lys Leu Gly Lys Lys Leu Gly Lys Leu Gly Lys Lys Leu Gly Lys Leu
1               5                   10                  15

Gly Lys Lys Leu Gly
            20

<210> SEQ ID NO 34
<211> LENGTH: 14
<212> TYPE: PRT
<213> ORGANISM: Artificial Sequence
<220> FEATURE:
<223> OTHER INFORMATION: Synthetic - antimicrobial peptide comprised of
      D-amino acids

<400> SEQUENCE: 34

Lys Leu Ala Lys Leu Ala Lys Lys Leu Ala Lys Leu Ala Lys
1               5                   10

<210> SEQ ID NO 35
<211> LENGTH: 51
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

<222> LOCATION: (7)..(51)
<223> OTHER INFORMATION: "Gly4Ser" may or may not be present

<400> SEQUENCE: 35

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
                20                  25                  30

Gly Gly Gly Ser Gly Gly Gly Gly Ser Gly Gly Gly Gly Ser Gly Gly
        35                  40                  45

Gly Gly Ser
    50

<210> SEQ ID NO 36
<211> LENGTH: 16
<212> TYPE: PRT
<213> ORGANISM: Artificial Sequence
<220> FEATURE:
<223> OTHER INFORMATION: Synthetic

<400> SEQUENCE: 36

Ser Gly Gly Gly Gly Ser Gly Gly Gly Gly Ser Gly Gly Gly Gly Ser
1               5                   10                  15

<210> SEQ ID NO 37
<211> LENGTH: 21
<212> TYPE: PRT
<213> ORGANISM: Artificial Sequence
<220> FEATURE:
<223> OTHER INFORMATION: Synthetic

<400> SEQUENCE: 37

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 38
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(30)
<223> OTHER INFORMATION: "Gly4Ser" may or may not be present

<400> SEQUENCE: 38

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 39
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(24)
<223> OTHER INFORMATION: "Gly3Ser" may or may not be present

<400> SEQUENCE: 39

```
Gly Gly Gly Ser Gly Gly Gly Ser Gly Gly Gly Ser Gly Gly Gly Ser
1               5                   10                  15
Gly Gly Gly Ser Gly Gly Gly Ser
                20
```

ANTIMICROBIAL CONSTRUCTS AND USES THEREOF

RELATED APPLICATION

This application claims the benefit of U.S. Provisional Application Ser. No. 62/467,058, filed on Mar. 3, 2017. The entire contents of the above-referenced application is incorporated herein by this reference.

GOVERNMENT SUPPORT

The invention was made with Government support under Grant No. HR0011-13-2-0017 awarded by the Defense Advanced Research Projects Agency. The Government has certain rights in the invention.

STATEMENT REGARDING SEQUENCE LISTING

The Sequence Listing associated with this application has been submitted electronically in ASCII format, and is hereby incorporated by reference into the specification in its entirety. The name of the text file containing the Sequence Listing is MITN-040_Sequence-Listing.txt. The text file is 17801 bytes, was created on Aug. 6, 2018, and is being submitted electronically via EFS-Web.

BACKGROUND

The global fight against pathogenic bacteria has become increasingly challenging due to the rising incidence of antibiotic resistance coupled with a paucity of new antibacterial agents entering the clinic. This has resulted in an urgent need to develop new classes of antibiotics. One promising class of anti-infectives is antimicrobial peptides. Peptides are promising building blocks because they possess diverse abilities such as binding to specific receptors, stimulating or blocking signaling cascades, or forming structures that interact with membranes, and there are emerging strategies available that can optimize and stabilize peptides for translation as therapeutics in living systems. Antimicrobial peptides are found in evolutionarily diverse species including prokaryotes, plants, insects, and mammals. Antimicrobial peptides kill target cells rapidly, possess a broad spectrum of activity, and have activity against some of the more serious antibiotic-resistant and clinically-relevant pathogens. Importantly, antimicrobial peptide-resistant microorganisms are relatively difficult to select in vitro.

However, two major obstacles facing the development of new antibiotics into the clinic are poor penetration of drugs into bacteria and off-target toxicity. For example, some antimicrobial peptides have been found to be toxic to mammalian cells, have reduced activity in vivo, or are less potent than conventional antibiotics. Hence, a need exists for more effective delivery of antimicrobial peptides, antibiotics and small molecules that result in improved activity, reduced toxicity, and minimal off-target effects.

SUMMARY

The present disclosure is based, in part, on the discovery that a membrane interacting peptide, when coupled with an antimicrobial agent, was capable of delivering the agent to gram-negative bacteria, thereby allowing the antimicrobial agent to have an inhibitory effect on the bacteria. Therefore, administration of an antimicrobial construct comprising a membrane interacting peptide and an antimicrobial agent as provided herein, is useful for treating and/or preventing microbial infections.

Accordingly, in some aspects, the disclosure relates to an antimicrobial construct, comprising a membrane interacting peptide and an antimicrobial agent, wherein the membrane interacting peptide associates with a prokaryotic cell membrane, and wherein the antimicrobial agent is a peptide or a small molecule.

In some aspects, the antimicrobial agent is a peptide, and the peptide is conjugated to the membrane interacting peptide. In other aspects, the antimicrobial agent is a small molecule, and the small molecule is conjugated to the membrane interacting peptide. In further aspects, the antimicrobial agent is covalently conjugated to the membrane interacting peptide. In yet a further aspect, the antimicrobial agent is non-covalently conjugated to the membrane interacting peptide.

In some aspects, the disclosure relates to an antimicrobial construct wherein the antimicrobial agent is conjugated to the membrane interacting peptide via a linker. In some aspects, the linker is selected from the group consisting of a disulfide linker, an esterase sensitive linker, a glycine linker, and a heterobifunctional crosslinker.

In any of the foregoing or related aspects, the membrane interacting peptide is selected from the group consisting of: lactoferrin, buforin, LBU1, WLBU1, LBU2, and WLBU2. In some aspects, the membrane interacting peptide is a lactoferrin-derived peptide. In some aspects, the lactoferrin-derived peptide comprises an amino acid sequence set forth in SEQ ID NO: 1. In other aspects, the membrane interacting peptide is WLBU2.

In any of the foregoing or related aspects, the antimicrobial agent is a peptide, and the peptide is an antimicrobial peptide. In some aspects, the antimicrobial peptide comprises a sequence selected from the group consisting of: (KLAKLAK)$_2$ (SEQ ID NO: 30), (KLAKKLA)$_2$ (SEQ ID NO: 31), (KAAKKAA)$_2$ (SEQ ID NO: 32), or (KLGKKLG)$_3$ (SEQ ID NO: 33). In some aspects, the antimicrobial peptide comprises D-amino acids. In some aspects, the antimicrobial peptide comprises the sequence $_D$(KLAKLAK)$_2$ (SEQ ID NO: 34).

In any of the foregoing or related aspects, the antimicrobial construct described herein comprises a plurality of membrane interacting peptides and a plurality of antimicrobial agents.

In any of the foregoing or related aspects, the antimicrobial construct described herein further comprises a tissue specific targeting moiety.

In any of the foregoing or related aspects, the antimicrobial construct described herein further comprises a microbe specific targeting moiety. In some aspects, the microbe specific targeting moiety targets a gram-negative bacterium. In some aspects, the gram-negative bacterium is *Pseudomonas*. In some aspects, the gram-negative bacterium is *P. aeruginosa*. In some aspects, the microbe specific targeting moiety is a peptide, such as P9b.

In any of the foregoing or related aspects, the antimicrobial agent is a small molecule, wherein the small molecule is selected from the group consisting of: linezolid, rifampin, mupirocin, erythromycin, clarithromycin, retapamulin, novobiocin, and fusidic acid.

In any of the foregoing or related aspects, association of the membrane interacting peptide with a prokaryotic membrane induces a change in membrane structure to allow for translocation of the antimicrobial agent. In some aspects, the change in membrane structure comprises formation of at least one pore in the membrane.

In any of the foregoing or related aspects, the antimicrobial construct described herein has minimal toxicity to mammalian cells in vitro or in vivo relative to toxicity to microbes.

In any of the foregoing or related aspects, the antimicrobial construct described herein has minimal propensity to lyse red blood cells in vitro or in vivo relative to propensity of microbes.

In any of the foregoing or related aspects, the antimicrobial construct described herein has selective activity against gram-negative bacteria.

In some aspects, the disclosure relates to an antimicrobial construct, comprising a membrane interacting peptide and an antimicrobial agent, wherein the membrane interacting peptide comprises an amino acid sequence set forth in SEQ ID NO: 1, and wherein the antimicrobial agent is a peptide comprising an amino acid sequence set forth in SEQ ID NO: 34.

In some aspects, the disclosure relates to an antimicrobial construct, comprising a membrane interacting peptide, and an antimicrobial small molecule, wherein the membrane interacting peptide comprises an amino acid sequence set forth in SEQ ID NO: 27.

In any of the foregoing or related aspects, the antimicrobial construct described herein further comprises a carrier.

Other aspects of the disclosure relate to a composition formulated for in vivo delivery, comprising at least one antimicrobial construct described herein, and a carrier. In some aspects, the membrane interacting peptide of the antimicrobial construct is conjugated to the carrier.

Other aspects of the disclosure relate to a composition formulated for in vivo delivery, comprising at least one membrane interacting peptide conjugated to a carrier, and an antimicrobial agent, wherein the antimicrobial agent is a peptide or small molecule. In some aspects, a plurality of membrane interacting peptides is conjugated to a single carrier. In some aspects, the at least one membrane interacting peptide or the plurality of membrane interacting peptides are conjugated to the carrier via a linker.

In any of the foregoing or related aspects, the carrier is a porous silicon nanoparticle, a lipid nanoparticle, a polymer nanoparticle, or a liposome. In some aspects, the carrier is a dextran molecule.

Other aspects of the disclosure relate to a composition formulated for in vivo delivery, comprising at least one membrane interacting peptide conjugated to a first carrier, and an antimicrobial agent conjugated to a second carrier, wherein the antimicrobial agent is a peptide or small molecule. In some aspects, the first and second carriers are co-formulated. In some aspects, the first carrier is a dextran molecule, and the second carrier is a porous silicon nanoparticle, a lipid nanoparticle, a polymer nanoparticle, or a liposome. In some aspects, the first carrier is a dextran molecule, and the second carrier is a dextran molecule.

In any of the foregoing or related aspects, the antimicrobial agent is conjugated to the carrier or the first carrier.

In any of the foregoing or related aspects, the composition described herein results in greater antimicrobial activity relative to free antimicrobial construct which lacks a carrier.

Other aspects of the disclosure relate to a method of treating a microbial infection in a subject, comprising administering a therapeutically effective amount of the antimicrobial construct described herein, or the composition described herein.

Other aspects of the disclosure relate to a method of prolonging survival of a subject with a microbial infection, comprising administering a therapeutically effective amount of the antimicrobial construct described herein, or the composition described herein.

In any of the foregoing or related aspects, the microbial infection is a bacterial infection. In some aspects, the bacterial infection is caused by a gram-negative bacterium. In some aspects, the gram-negative bacterium is *P. aeruginosa*.

Other aspects of the disclosure relate to a method of inducing selective toxicity in vivo in a microbe, comprising administering to a subject an effective amount the antimicrobial construct described herein, or the composition described herein, thereby inducing toxicity in the microbe.

In any of the foregoing aspects, the disclosure provides use of an antimicrobial construct described herein, in the manufacture of a medicament for treating a microbial infection in a subject or prolonging survival of a subject with a microbial infection, wherein the medicament comprises the antimicrobial construct, and an optional pharmaceutically acceptable carrier, and wherein the treatment comprises administration of the medicament.

In another aspect, the disclosure provides an antimicrobial construct for use in a method of treating a microbial infection in a subject, wherein the antimicrobial construct comprises a membrane interacting peptide and an antimicrobial agent, wherein the membrane interacting peptide associates with a prokaryotic cell membrane, and wherein the antimicrobial agent is a peptide or a small molecule.

In another aspect, the disclosure provides an antimicrobial construct for use in a method of prolonging survival of a subject with a microbial infection, wherein the antimicrobial construct comprises a membrane interacting peptide and an antimicrobial agent, wherein the membrane interacting peptide associates with a prokaryotic cell membrane, and wherein the antimicrobial agent is a peptide or a small molecule.

In another aspect, the disclosure provides a composition for use in a method of treating a microbial infection in a subject, wherein the composition comprises at least one antimicrobial construct and a carrier, wherein the antimicrobial construct comprises a membrane interacting peptide and an antimicrobial agent, wherein the membrane interacting peptide associates with a prokaryotic cell membrane, and wherein the antimicrobial agent is a peptide or a small molecule.

In another aspect, the disclosure provides a composition for use in a method of prolonging survival of a subject with a microbial infection, wherein the composition comprises at least one antimicrobial construct and a carrier, wherein the antimicrobial construct comprises a membrane interacting peptide and an antimicrobial agent, wherein the membrane interacting peptide associates with a prokaryotic cell membrane, and wherein the antimicrobial agent is a peptide or a small molecule.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 5A is a schematic showing how peptide cargo can be loaded in a biodegradable porous silicon nanoparticle (pSiNP) for improved biodistribution.

FIG. 5B shows the percent peptide loading in pSiNP modified with phosphonate, carboxylate, sulfonate, and amine surface chemistries.

FIG. 5C is a diagram of the electrostatic interactions between negatively-charged phosphonate-modified pores of pSiNP and positively-charged peptides.

FIG. 5D compares TEM images of unloaded pSiNP and peptide-loaded pSiNP and shows that the porous structure was maintained in both cases. Scale bar represents 50 nm.

FIG. 5E is a graph of the zeta potential measurements of pSiNP, phosphonate modified pSiNP, and LACT-dKK pSiNP.

FIG. 9A shows distribution of LACT-dKK formulated in pSiNP (peptide-pSiNP) in heart, lungs, liver, kidney, and spleen, as measured by peptide fluorescence 4 hours after the last administration.

FIG. 9B is a microscopy image showing the distribution of *P. aeruginosa* (PA, red) and LACT-dKK pSiNP (peptide, green) in the mouse lung. Scale bar represents 2 mm.

FIG. 9C is a bar graph showing the percent of mice that survive for at least 24 hours after co-administration of intratracheal *P. aeruginosa* and PBS, pSiNP, or LACT-dKK formulated into pSiNP (peptide-pSiNP).

FIG. 9D is a graph of the number of bacteria recovered from the lungs from mice that survived for at least 24 hours.

FIG. 10A shows IVIS images of organs from mice administered PBS (control) or LACT-dKK formulated into pSiNP (peptide-pSiNP).

FIG. 10B shows lung sections from untreated mice and mice delivered LACT-dKK formulated into pSiNP (peptide-pSiNP; peptide-FAM; green) stained for monocytes (magenta, CD11b Abcam 1:1000) or alveolar macrophages (red, F4/80; Abcam 1:50). White arrows indicate peptide co-localization with F4/80. Scale bar represents 40 μm.

DETAILED DESCRIPTION

Overview

Figure 1A:
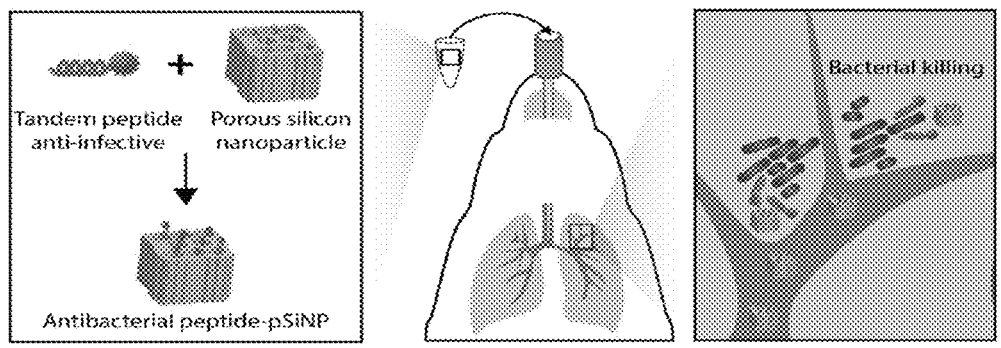
FIG. 1A is a schematic showing the overall approach for designing materials composed of a tandem peptide anti-infective (i.e., an antimicrobial construct) loaded in biodegradable porous silicon nanoparticles for delivery to lung infection models.

The present disclosure is based, at least in part, on the results of screening a library of membrane-interacting peptides conjugated to antimicrobial peptide $_D$(KLAKLAK)$_2$ ("dKK") or linezolid, to identify peptides that could efficiently deliver antimicrobial agents that were previously ineffective against gram-negative bacteria. Specifically, membrane interacting peptides lactoferrin and WLBU2 were capable of selectively delivering the antimicrobial agent to *P. aeruginosa*, a gram-negative bacterium. This delivery resulted in inhibition of bacterial growth and prolonged survival of infected mice. The coupling of membrane interacting peptides and antimicrobial agents was found to be synergistic.

Definitions

Terms used in the claims and specification are defined as set forth below, unless otherwise specified.

It must be noted that, as used in the specification and the appended claims, the singular forms "a," "an" and "the" include plural referents unless the context clearly dictates otherwise.

As used herein, the term "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

Every amino acid (except glycine) can occur in two isomeric forms, because of the possibility of forming two different enantiomers (stereoisomers) around the central carbon atom. These are called L- and D-forms, analogous to left-handed and right-handed configurations. Generally, only L-amino acids are manufactured in cells and incorporated into proteins. Some D-amino acids are found in the cell walls of bacteria, but not in bacterial proteins. In some embodiments, the antimicrobial constructs described herein comprise peptides comprising L-amino acids. In some embodiments, the antimicrobial constructs described herein comprise peptides comprising D-amino acids.

As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

As used herein, the term "antibacterial", or "antibiotic", refers to the ability to kill or slow the growth of one or more bacteria. Antibacterials are used in the treatment and prevention of bacterial infections.

As used herein, the term "antimicrobial" refers to the ability to kill or slow the growth of one or more microbes. Microbes include bacteria, including gram-positive and gram-negative bacteria, fungi, parasites such as protozoa, and viruses.

As used herein, the term "antimicrobial agent" refers to a peptide or small molecule that exhibits antimicrobial activity. In some embodiments, the antimicrobial agent is a peptide or small molecule that is known in the art for having antimicrobial activity. In some embodiments, the antimicrobial agent is a peptide or small molecule that was previously ineffective against gram-negative bacteria. In some embodiments, the antimicrobial agent is an antibiotic.

As used herein, the term "antimicrobial peptide" means a naturally occurring or synthetic peptide having antimicrobial activity. An antimicrobial peptide can, for example, kill or slow the growth of one or more strains of bacteria including a gram-positive or gram-negative bacteria, or a fungi or protozoa. Thus, an antimicrobial peptide can have, for example, bacteriostatic (inhibition of growth) or bactericidal (killing) activity against, for example, one or more strains of *Escherichia coli, Pseudomonas aeruginosa* or *Staphylococcus aureus*.

An antimicrobial peptide is typically highly basic and can have a linear or cyclic structure. As discussed further below, an antimicrobial peptide can have an amphipathic α-helical structure (see U.S. Pat. No. 5,789,542 Javadpour et al., 1996 *J. Med. Chem*. Vol. 39: 3107-3113, 1996; Blondelle and Houghten, in Bristol (Ed.), Annual Reports in Medicinal Chemistry pages 159-168 Academic Press, San Diego). An antimicrobial peptide also can be, for example, a β-strand/sheet-forming peptide as described in Mancheno et al., J. Peptide Res. 51:142-148 (1998).

As used herein, the terms "associate", "associates" and "association" refers to the interaction or connection of a peptide (e.g., membrane interacting peptide) with a microbe (e.g., the surface of a prokaryote, e.g., the lipid membrane of a prokaryote). In some embodiments, association of a peptide (e.g., membrane interacting peptide) with a microbe disrupts the membrane of the microbe. In some embodiments, the peptide (e.g., membrane interacting peptide) associates with a microbe for a sufficient time to disrupt the membrane of the microbe. In some embodiments, the peptide (e.g., membrane interacting peptide) associates with a microbe for a sufficient time to disrupt the membrane of the microbe and deliver a cargo (e.g., an antimicrobial agent). In some embodiments, efficacy of the antimicrobial construct described herein requires association of the membrane-interacting peptide with the microbe. In some embodiments, efficacy of the antimicrobial construct described herein requires association of the membrane-interacting peptide with the microbe and disruption of the membrane of the microbe.

As used herein, the term "coupled" refers to a juxtaposition wherein the components described are in a relationship permitting hem to function in their intended manner.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions. A polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain embodiments, there is one amino acid difference between a starting polypeptide sequence and the sequence derived there from. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity. In certain embodiments, a polypeptide consists of, consists essentially of, or comprises an amino acid sequence selected from a sequence set forth in the Summary of Sequences Table. In certain embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from a sequence set forth in the Summary of Sequences Table. In certain embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from a sequence set forth in the Summary of Sequences Table. In certain embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from a sequence set forth in the Summary of Sequences Table.

In certain embodiments, the polypeptides of the disclosure are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, and the like.

It will also be understood by one of ordinary skill in the art that the polypeptides suitable for use in the methods disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The polypeptides suitable for use in the methods disclosed herein may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain embodiments, a string of amino acids can be replaced with a structurally similar string that differs in order and/or composition of side chain family members. Alternatively, in certain embodiments, mutations may be introduced randomly along all or part of a coding sequence, such as by saturation mutagenesis, and the resultant mutants can be incorporated into binding polypeptides of the invention and screened for their ability to bind to the desired target.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "gly-ser polypeptide linker" refers to a peptide that consists of glycine and serine residues. An exemplary gly-ser polypeptide linker comprises the amino acid sequence Ser(Gly$_4$Ser)n. In certain embodiments, n=1. In certain embodiments, n=2. In certain embodiments, n=3, i.e., Ser(Gly$_4$Ser)3. In certain embodiments, n=4, i.e., Ser(Gly$_4$Ser)4. In certain embodiments, n=5. In certain embodiments, n=6. In certain embodiments, n=7. In certain embodiments, n=8. In certain embodiments, n=9. In certain embodiments, n=10. Another exemplary gly-ser polypeptide linker comprises the amino acid sequence (Gly$_4$Ser)n. In certain embodiments, n=1. In certain embodiments, n=2. In certain embodiments, n=3. In certain embodiments, n=4. In certain embodiments, n=5. In certain embodiments, n=6. Another exemplary gly-ser polypeptide linker comprises the amino acid sequence (Gly$_3$Ser)n. certain embodiments, n=1. In certain embodiments, n=2. In certain embodiments, n=3. In certain embodiments, n=4. In certain embodiments, n=5. In certain embodiments, n=6.

As used herein, the term "inhibits growth" (e.g., referring to cells) is intended to include any measurable decrease in the growth of a cell, e.g., the inhibition of growth of a cell by at least about 10%, 20%, 30%, 40%, 50%, 60%, 70%, 80%, 90%, 99%, or 100%. In some embodiments, the term "inhibits growth" refers to any measure decrease in the growth of a microbe (e.g., bacterium), e.g., the inhibition of growth of a microbe by at least about 10%, 20%, 30%, 40%, 50%, 60%, 70%, 80%, 90%, 99% or 100%.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising polypeptide described herein).

The term "in vivo" refers to processes that occur in a living organism.

The term "in vitro" refers to processes that occur outside of a living organism, for example, in a test tube.

In some embodiments, the antimicrobial constructs described herein comprise one or more "linker domains," such as polypeptide linkers. As used herein, the term "linker" or "linker domain" refers to a sequence which connects two or more domains or peptides (e.g., the membrane interacting peptide and antimicrobial agent, or membrane interacting peptide and carrier) in a linear sequence. As used herein, the term "polypeptide linker" refers to a peptide or polypeptide sequence (e.g., a synthetic peptide or polypeptide sequence) which connects two or more domains in a linear amino acid sequence of a polypeptide chain. For example, polypeptide linkers may be used to couple a membrane interacting peptide to an antimicrobial agent (e.g., a peptide). In some embodiments, such polypeptide linkers can provide flexibility to the antimicrobial construct.

As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

As used herein, the term "membrane interacting peptide" refers to a peptide that associates with the cell membrane of a prokaryote. In some embodiments, the membrane interacting peptide delivers the antimicrobial construct described herein to the microbe of interest (e.g., gram-negative bacteria). In some embodiments, association with the membrane includes binding to the membrane covalently or non-covalently. In some embodiments, the membrane interacting peptide disrupts the structure of the membrane in a way that allows the antimicrobial agent described herein, to effectuate a response. In some embodiments, the membrane interacting peptide allows for translocation of the antimicrobial agent into the microbe. In some embodiments, the membrane interacting peptide forms a pore, allowing the antimicrobial agent to enter the microbe. In some embodiments, the membrane interacting peptide physically locates the antimicrobial agent to the membrane. In some embodiments, the membrane interacting peptide lacks antimicrobial activity. In some embodiments, the membrane interacting peptide has antimicrobial activity outside of an antimicrobial construct, and lacks antimicrobial activity once formed in an antimicrobial construct. In some embodiments, the membrane interacting peptide lacks toxicity against mammalian cells. In some embodiments, the membrane interacting peptide confers toxicity against mammalian cells out of an antimicrobial construct, and lacks toxicity against mammalian cells once formed in an antimicrobial construct. In some embodiments, the membrane interacting peptide does not induce hemolysis. In some embodiments, the membrane interacting peptide induces hemolysis outside of an antimicrobial construct, and lacks hemolytic activity once formed in an antimicrobial construct.

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell.

Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "subject" includes any human or non-human animal. For example, the methods and compositions of the present invention can be used to treat a subject with a microbial infection. The term "non-human animal" includes all vertebrates, e.g., mammals and non-mammals, such as non-human primates, sheep, dog, cow, chickens, amphibians, reptiles, etc.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and)(BLAST programs (version 2.0) of Altschul, et al. (1990) *J Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g.,)(BLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present disclosure, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired.

As used herein, the term "targeting moiety" refers to a tissue-specific or microbe-specific moiety that delivers the antimicrobial construct, or corresponding composition, described herein, to a tissue or microbe of interest. In some embodiments, the targeting moiety is a receptor or ligand that binds to a corresponding ligand or receptor present on the tissue or microbe of interest. In some embodiments, the tissue of interest is lung. In some embodiments, the microbe of interest is a gram-negative bacteria. In some embodiments, the microbe of interest is *P. aeruginosa.*

As used herein, the terms "therapeutically effective amount" or "therapeutically effective dose," or similar terms used herein are intended to mean an amount of an agent that will elicit the desired biological or medical response (e.g., an improvement in one or more symptoms of a bacterial infection).

The terms "treat," "treating," and "treatment," as used herein, refer to therapeutic or preventative measures described herein. The methods of "treatment" employ administration to a subject, in need of such treatment, an antimicrobial construct of the present disclosure, for example, a subject who ultimately may acquire such an infection, in order to prevent, cure, delay, reduce the severity of, or ameliorate one or more symptoms of the infection, or in order to prolong the survival of a subject beyond that expected in the absence of such treatment.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Antimicrobial Constructs

The present disclosure is based on the discovery that a non-antimicrobial lactoferrin-derived peptide coupled with either antimicrobial peptide dKK or antibiotic linezolid, having efficacy against gram positive bacteria, forms an antimicrobial construct having antibacterial activity against the gram negative bacteria, P. aeruginosa. In addition, the disclosure is based on the discovery that a WLBU2 peptide, previously shown to have antimicrobial activity, when coupled with the antibiotic linezolid, forms an antimicrobial construct having antibacterial activity against P. aeruginosa. Accordingly, without being bound by theory, the present disclosure provides an antimicrobial construct comprising a membrane interacting peptide and an antimicrobial agent. In some aspects, the antimicrobial construct further comprises a targeting moiety.

Important characteristics of the antimicrobial construct include high antimicrobial activity and low mammalian cell toxicity. Mammalian cell toxicity can be assessed using routine assays. For example, mammalian cell toxicity can be assayed by lysis of human erythrocytes in vitro as described in Javadpour et al. 1996 J. Med. Chem. Vol. 39: 3107-3113, herein incorporated by reference in its entirety. In some embodiments, an antimicrobial peptide having "low mammalian cell toxicity" is not lytic to human erythrocytes. Antimicrobial activity can be assessed using routine assays and are described infra.

Moreover, the antimicrobial constructs described herein were found capable of altering the efficacy of an antimicrobial agent. For example, an antimicrobial construct comprising an antibiotic for gram-positive bacteria, provided efficacy of the antibiotic against gram-negative bacteria.

Membrane Interacting Peptides

The antimicrobial construct described herein comprises at least one membrane interacting peptide. The membrane interacting peptide associates with the cell membrane of a prokaryote, thereby delivering the antimicrobial agent of the construct to the prokaryote. In some embodiments, the membrane interacting peptide has antimicrobial activity. In some embodiments, the membrane interacting peptide lacks antimicrobial activity. In some embodiments, the membrane interacting peptide has antimicrobial activity, but lacks antimicrobial activity in an antimicrobial construct described herein. In some embodiments, the membrane interacting peptide has mammalian cell toxicity. In some embodiments, the membrane interacting peptide lacks mammalian cell toxicity. In some embodiments, the membrane interacting peptide has mammalian cell toxicity, but lack mammalian cell toxicity in an antimicrobial construct described herein. In some embodiments, the membrane interacting peptide has hemolytic activity. In some embodiments, the membrane interacting peptide lacks hemolytic activity. In some embodiments, the membrane interacting peptide has hemolytic activity, but lacks hemolytic activity in an antimicrobial construct described herein.

In some embodiments, the membrane interacting peptide disrupts the cell membrane of the prokaryote. In some embodiments, the membrane interacting peptide forms a barrel-stave pore, wherein peptides insert perpendicularly in the bilayer, associate and form a pore. The peptides line the pore lumen in a parallel direction relative to the phospholipid chains, which remain perpendicular to the bilayer plane. In some embodiments, the membrane interacting peptide disrupts the membrane via the carpet mechanism. Specifically, peptides adsorb parallel to the bilayer and, after reaching sufficient coverage, produce a detergent-like effect that disintegrates the membrane. In some embodiments, the membrane interacting peptide forms a toroidal pore. Similar to the barrel-stave pore, the peptides insert perpendicularly to the bilayer, but instead of packing parallel to the phospholipid chains, induce a local membrane curvature in such a way that the pore lumen is lined partly by peptides and partly by phospholipid head groups. Here, continuity between inner and outer leaflets is established. In some embodiments, the membrane interacting peptide forms a disordered toroidal pore, wherein there are less-rigid peptide conformations, and the pore lumen is lined by the phospholipid head groups.

Methods for analyzing the mechanism of disruption of the cell membrane of a prokaryote by the membrane interacting peptide are known to those of skill in the art. For example, molecular dynamic stimulations of peptides with membrane, as described by Jean-Francois, F. et al. Biophys J. 2008 Dec. 15; 95(12): 5748-5756, incorporated herein by reference in its entirety. Another method is electrochemical scanning tunneling spectroscopy to image peptides in a phospholipid matrix, as described by Pieta, P. et al. PNAS 2012 December; 109(52): 21223-21227, and Smetanin, M. et al. Biochimica et Biophysica Act 2014; 1838: 3130-3136, each of which is incorporated herein by reference in its entirety. Additional visualization methods include NMR, circular dichroism, and X-ray scattering, as reviewed by Sato, H. and Feix, J B, Biochim Biophys Acta 2006 Sep. 17; 1758(9): 1245-56, incorporated herein by reference in its entirety.

In some embodiments, the membrane interacting peptide is lactoferrin or is derived from human lactoferrin. The native human lactoferrin protein comprises the amino acid sequence set forth in SEQ ID NO: 2. In some embodiments, the membrane interacting peptide has an amino acid sequence having at least 50%, 60%, 70%, 80%, 90% or 100% identity to SEQ ID NO: 2. In some embodiments, the lactoferrin-derived peptide has a length of 14 to 30, 19 to 30, 20 to 30, 21 to 23, or 22 amino acids. In some embodiments, the lactoferrin-derived peptide has a length of 22 amino acids. In some embodiments, the lactoferrin-derived peptide includes at least two cysteine residues. In some embodiments, the at least two cysteine residues forms an internal cysteine-cysteine-bridge. In some embodiments, the lactoferrin-derived peptide comprises at least 4, at least 6, 4 to 8, 5, 6 or 7 amino acids with, at or below pH 7, positively charged side chains, such as arginine and lysine.

In some embodiments, the lactoferrin-derived peptide comprises the amino acid sequence set forth in SEQ ID NO: 1. In some embodiments, the lactoferrin-derived peptide does not differ in more than 8, 7, 6, 5, 4, 3, 2 or 1 amino acid positions from SEQ ID NO: 1. In some embodiments, the lactoferrin-derived peptide comprises an amino acid sequence having at least 80 to 90% identity to SEQ ID NO: 1. In some embodiments, the lactoferrin-derived peptide comprises an amino acid sequence having at least 80% identity to SEQ ID NO: 1. In some embodiments, the lactoferrin-derived peptide comprises an amino acid sequence having at least 85% identity to SEQ ID NO: 1. In some embodiments, the lactoferrin-derived peptide comprises an amino acid sequence having at least 90% identity to SEQ ID NO: 1. In some embodiments, the lactoferrin-derived peptide comprises an amino acid sequence having at least 95% identity to SEQ ID NO: 1. In some embodiments, the lactoferrin-derived peptide comprises an amino acid sequence having at least 96%, at least 97%, at least 98% or at least 99% identity to SEQ ID NO: 1.

In some embodiments, the lactoferrin-derived peptide is one described in WO 2007/048599 or WO 2012/069089, herein incorporated by reference in their entirety.

In some embodiments, the membrane interacting peptide is buforin 2. Buforin 2 is a 21-amino acid peptide with pore-forming activity. In some embodiments, buforin 2 comprises the amino acid sequence set forth in SEQ ID NO: 5. In some embodiments, the membrane interacting peptide has an amino acid sequence having at least 50%, 60%, 70%, 80%, 90% or 100% identity to SEQ ID NO: 5. In some embodiments, the membrane interacting peptide does not differ in more than 8, 7, 6, 5, 4, 3, 2 or 1 amino acid positions from SEQ ID NO: 5.

In some embodiments, the membrane interacting peptide is a Lytic Base Unit (LBU) peptide (e.g., LBU-1, LBU-2, LBU-3, LBU-3.5, LBU-4, WLBU-1, WLBU-2, WLBU-3, and WLBU-4), as described in U.S. Pat. No. 8,071,540; Deslouches, B., et al., 2005, *Antimicrobial Agents and Chemotherapy*, Vol. 49(1): 316-322; and Deslouches, B., et al. 2005, *Antimicrobial Agents and Chemotherapy*, Vol. 49 (8): 3208-3216, each of which is herein incorporated by reference in its entirety. These LBU peptides are lentiviral lytic peptide 1 (LLP1) analogs, wherein the LLP1 parent sequence corresponds to amino acids 828-856 of the HIV-1 viral isolate HXB2R Env, which have been previously described (see Tencza et al., 1999, *Journal of Antimicrobial Chemotherapy*, Vol. 44: 33-41, and U.S. Pat. Nos. 5,714,577 and 5,945,507, each of which is herein incorporated by reference in its entirety). In some embodiments, the LBU peptides comprise modifications that (i) optimize amphipathicity, (ii) substitute with Arg on the charged face and Val on the hydrophobic face, (iii) increase peptide length, and (iv) periodically substitute Val with Trp.

In some embodiments, the membrane interacting peptide is WLBU-2 (SEQ ID NO: 27). In some embodiments, the membrane interacting peptide has an amino acid sequence having at least 50%, 60%, 70%, 80%, 90% or 100% identity to SEQ ID NO: 27. In some embodiments, the membrane interacting peptide does not differ in more than 8, 7, 6, 5, 4, 3, 2 or 1 amino acid positions from SEQ ID NO: 27.

It will be obvious to one of skill in the art to determine whether a peptide interacts with the cell membrane of a prokaryote. Methods include, but are not limited to, tryptophan fluorescence measurement (tryptophans in membranes will shift absorbance measurement), super resolution microscopy, transmission electron microscopy, imaging flow cytometry, subcellular fractionation, and liposome leakage assay, wherein peptides are incubated with liposomes as a model membrane leakage of dye from inside of the liposome is assessed.

Assays for determining disruption of the cell membrane are known to those of skill in the art. See Wimley, W., Methods Mol Biol. 2015; 1324: 89-106 for exemplary methods. To fully communicate the effect that a peptide has on the integrity of a lipid bilayer, four properties can be assessed: potency, kinetics, transience and pore size. The potency of a peptide describes the ability of a peptide to disrupt a lipid bilayer, on a peptide per lipid basis. Potency is best described using the ratio of bound peptide to total lipid (Pbound:L). To determine Pbound, membrane binding is measure. Exemplary methods for measuring fractional peptide binding is equilibrium dialysis, fluorescence titration, circular dichroism titration, and filter binding. Potency is important to note because almost any membrane-interacting peptide will disrupt bilayers at a high enough Pbound:L. (P:L≥1:50), a concentration range that is likely not relevant to the biological activity of the peptide. The most informative way to express potency is to record the Pbound:lipid that causes 50% effect, or PL50. This parameter ranges from ≥1, for peptides that have no effect on bilayers, to ≤1:2000, for the most potent membrane-disrupting peptides known (Krauson A J, et al. Biochim Biophys Acta. 2012; 1818: 1625-1632; Parente R A, et al. Biochemistry. 1990; 29: 8720-8728). The kinetics of leakage describe the rate at which leakage occurs and the rate at which it stops. Rate measurements provide important information about the permeabilization mechanism. Peptide-induced leakage of solutes from lipid vesicles can range from almost instantaneous (t½<30 seconds) to very slow with T½>10 hours. However most peptide-induced leakage occurs within 2-30 minutes after peptide addition.

The transience of permeabilization describes the lifetime of the disruption of bilayer integrity. Surprisingly, the majority of published examples of peptide-induced membrane permeabilization occur through transient, non-equilibrium processes (Krauson A J, et al., supra; Krauson A J, et al. J Am Chem Soc. 2012; 134: 12732-12741). Leakage occurs only in the minutes immediately after peptide addition. The system then relaxes to a state where leakage slows or stops completely despite the continued presence of the peptides in the bilayer. Transient leakage cannot be correctly modeled as an equilibrium state of the membrane. Even the archetypal pore forming peptide melittin causes transient, non-equilibrium permeabilization at moderate peptide concentrations (Pbound:L≤1:100). The reason for transient leakage has not been definitively proven. The leading hypothesis is that the initial binding of peptide to the surface of the bilayer causes an imbalance of mass, charge or surface tension, which is dissipated by the stochastic, transient failure of the bilayer structure. When the asymmetry of peptide distribution has been relieved, the permeabilization no longer occurs. Transient membrane disruption means that simulations and structural modelling based on equilibrium phenomena are unlikely to reveal true mechanistic details.

The "pore" size allows a description of the size of the disruption of bilayer integrity. Peptide-induced release of molecules is generally probed using small fluorescent probes of a few hundred Daltons. But important information on the characteristics of the membrane disruption can also be obtained by examining the dependence of membrane permeabilization on the size of the probe. Some membrane permeabilizing peptides, at high concentration (Pbound: L≥1:50), disrupt bilayers catastrophically (Ladokhin A S, White S H, Biochim Biophys Acta. 2001; 1514:253-260; Hristova K, et al. J Biol Chem. 1997; 272:24224-24233; Goñi F M, Ostolaza H. Brazilian Journal of Medical and Biological Research. 1998; 31:1019-1034), such that all entrapped probes escape equally well, independent of size. Other peptides show a distinct size dependence for leakage, indicating a more well-defined pathway for solute escape (Ladokhin A S, Biophys J. 1997; 72:1762-1766). Finally, some peptides do not release macromolecules at all, indicating that only small pores are formed. Information on pore size provides important clues to the mechanism of peptide-induced disruption of lipid bilayer membranes.

Antimicrobial Agents

The antimicrobial construct described herein comprises an antimicrobial agent. In some embodiments, the antimicrobial agent is conjugated to the membrane interacting peptide. Antimicrobial agents for use in the constructs and methods described herein, are peptides and small molecules. In some embodiments, the antimicrobial agent has known antimicrobial activity. In some embodiments, the antimicrobial agent is a peptide or small molecule not previously identified as having antimicrobial activity. Selection of the antimicrobial agent will depend on the microbe being targeted.

Methods of assessing whether an agent has antimicrobial activity are readily available to those of skill in the art. For example, microdilution assays, such as agar dilution and broth dilution, are used to determine minimum inhibitory concentrations (MIC), the lowest concentration of the agent at which there is no bacterial growth, as standardized by the Clinical and Laboratory Standards Institute. In some embodiments, checkerboard assays can be used to determine if two antimicrobial agents have synergy, additive, or antagonistic effects when dosed together. Checkboard assays determine the interaction and potency of two test articles when used concurrently. Using Lorian methodology, the effect on potency of the combination of antimicrobials in comparison to their individual activities, represented as the Fractional Inhibitory Concentration (FIC) index value. To quantify the interactions between the antimicrobials being tested, the FIC index (the combination of antimicrobials that produced the greatest change from the individual antimicrobial's MIC) value is calculated for each strain and antimicrobial combination: $(A/MIC_A)+(B/MIC_B)=FIC_A+FIC_B=FIC$ Index, where A and B are the MIC of each antimicrobial in combination (in a single well), and $MIC_A$ and $MIC_B$ are the MIC of each antimicrobial individually.

In some embodiments, the antimicrobial agent is toxic to the microbe of interest. In some embodiments, the antimicrobial agent is not toxic to the microbe of interest until it is delivered in the antimicrobial construct described herein. Methods for determining toxicity to a microbe of interest are known to those of skill in the art and further described herein.

In some embodiments, the antimicrobial agent is toxic to mammalian cells. In some embodiments, the antimicrobial agent is not toxic to mammalian cells when delivered in the antimicrobial construct described herein. Methods for determining toxicity to mammalian cells are known to those of skill in the art. For example, a variety of cultured cells are exposed to escalating doses of agents for 24-72 hours and assayed for viability using endpoint measurements. These endpoint measurements include 3-(4,5-dimethylthiazol-2-yl)-2,5-diphenyltetrazolium bromide (MTT) assay, lactate dehydrogenase (LDH) leakage. The MTT assay is described in Morris, M et al. Nature Biotech December 2001; 19: 1173-1176, incorporated herein by reference in its entirety. The LDH assay is described in Lindgren, M. et al. Biochemical Pharmacology 2006; 71: 416-425, incorporated herein by reference in its entirety.

In some embodiments, the toxicity of an antimicrobial construct or antimicrobial agent to mammalian cells corresponds to the ability of the construct or agent to induce hemolysis (i.e., lysis of red blood cells). Hemolysis can lead to hemoglobinemia due to hemoglobin released into the blood plasma. In some embodiments, the antimicrobial agent lyses red blood cells. In some embodiments, the antimicrobial agent does not lyse red blood cells when delivered in the antimicrobial construct described herein. Methods for determining red blood cell lysis are known to those of skill in the art. For example, erythrocytes can be exposed to escalating doses of agents and free hemoglobin from lysed cells can be separated from unlysed cells using centrifugation. Hemoglobin absorbance can be measured by measuring the absorbance at 570 nm. See, for example, Hawrani, A. et al. Journal of Biological Chemistry, 2008 Jul. 4; 283(27): 18636-18645, incorporated herein by reference in its entirety.

Antimicrobial Peptides

In some embodiments, the antimicrobial agent used in the antimicrobial construct described herein, is an antimicrobial peptide. An antimicrobial peptide can be a naturally occurring or synthetic peptide. Naturally occurring antimicrobial peptides have been isolated from biological sources such as bacteria, insects, amphibians and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, Biopolymers 37:105-122 (1995); Alvarez-Bravo et al., Biochem. J. 302:535-538 (1994); Bessalle et al., FEBS 274:151-155 (1990); and Blondelle and Houghten in Bristol (Ed.), Annual Reports in Medicinal Chemistry pages 159-168 Academic Press, San Diego, each of which is herein incorporated by reference). In some embodiments, an antimicrobial peptide also can be an analog of a natural peptide, especially one that retains or enhances amphipathicity.

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn, see Creighton, Proteins: Structures and Molecular Properties W.H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis. The amphipathic α-helical structure allows the peptide to interact with cell membrane. Specifically, the inner leaflet of the outer membrane contains lipids which are amphipathic. Accordingly, an antimicrobial peptide having amphipathicity allows it to interact with the outer membrane.

Antimicrobial peptides of widely varying sequence have been isolated, sharing an amphipathic α-helical structure as a common feature (Saberwal et al., Biochim. Biophvs. Acta 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., Biopolymers 37:105-122 (1995)).

As used herein in reference to an antimicrobial peptide, the term "amphipathic α-helical structure" means an α-helix with a hydrophilic face containing several polar residues at physiological pH and a hydrophobic face containing non-polar residues. A polar residue can be, for example, a lysine or arginine residue, while a nonpolar residue can be, for example, a leucine or alanine residue. An antimicrobial peptide having an amphipathic α-helical structure generally has an equivalent number of polar and nonpolar residues within the amphipathic domain and a sufficient number of basic residues to give the peptide an overall positive charge at neutral pH (Saberwal et al., Biochim. Biophvs. Acta 1197:109-131 (1994), which is incorporated by reference herein). One skilled in the art understands that helix-promoting amino acids such as leucine and alanine can be advantageously included in an antimicrobial peptide disclosed herein (see, for example, Creighton, supra, 1984).

A variety of antimicrobial peptides having an amphipathic α-helical structure are well known in the art. Such peptides include synthetic, minimalist peptides based on a heptad building block scheme in which repetitive heptads are composed of repetitive trimers with an additional residue.

Such synthetic antimicrobial peptides include, for example, peptides of the general formula [(X$_1$X$_2$X$_2$) (X$_1$X$_2$X$_2$) X$_1$]$_n$ (SEQ ID NO: 35) or [(X$_1$X$_2$X$_2$)X$_1$(X$_1$X$_2$X$_2$)]$_n$ (SEQ ID NO: 36), where X$_1$ is a polar residue, X$_2$ is a nonpolar residue; and n is 2 or 3 (see Javadpour et al., supra, 1996. (KLAK-LAK)$_2$ (SEQ ID NO: 30); (KLAKKLA), (SEQ ID NO: 31); (KAAKKAA), (SEQ ID NO: 32); and (KLGKKLG)$_3$ (SEQ ID NO: 33) are examples of synthetic antimicrobial peptides having an amphipathic α-helical structure. Similar synthetic, antimicrobial peptides having an amphipathic α-helical structure also are known in the art, for example, as described in U.S. Pat. No. 5,789,542.

Helicity readily can be determined by one skilled in the art, for example, using circular dichroism spectroscopy. Percent α-helicity can be determined, for example, after measuring molar ellipticity at 222 nm as described in Javadpour et al., supra, 1996 (see, also, McLean et al., Biochemistry 30:31-37 (1991), which is incorporated by reference herein). An amphipathic α-helical antimicrobial peptide of the invention can have, for example, at least about 200 helicity when assayed in amphipathic media such as 25 mM SDS. One skilled in the art understands that such an antimicrobial peptide having an amphipathic α-helical structure can have, for example, at least about 25%, 30%, 35% or 40% helicity when assayed in 25 mM SDS. An antimicrobial peptide having an α-helical structure can have, for example, from 25% to 90% helicity; 25% to 60% helicity; 25% to 50% helicity; 25% to 40% helicity; 30% to 90% helicity; 30% to 60% helicity; 30% to 50% helicity; 40% to 90% helicity or 40% to 60% helicity when assayed in 25 mM SDS. Amphipathicity can readily be determined, for example, using a helical wheel representation of the peptide (see, for example. Blondelle and Houghten, supra, 1994).

In some embodiments, the antimicrobial peptide is a bactericidal cationic peptide. There is a general consensus that highly cationic peptides kill bacteria primarily by injuring their membranes. In some embodiments, a cationic peptide renders bacteria non-viable by activating their autolytic wall enzymes, muramidases, resulting in bacteriolysis. In this respect, cationic peptides mimic the bactericidal/bacteriolytic effects exerted by beta-lactam antibiotics. Accordingly, in some embodiments, a bactericidal cationic peptide mimics beta-lactam antibiotics. See Ginsburg, I., 2004 *Medical Hypotheses*, Vol. 62(3): 367-374 for a review of these peptides, herein incorporated by reference. Examples of such cationic peptides, include, but are not limited to: lysozyme, neutrophil-derived permeability increases peptides, defensins, elastase, cathepsin G, and secretory phospholipase A$_2$.

In some embodiments, the antimicrobial peptide is a cathelicidin-derived peptide. Peptides of the cathelicidin family contribute to innate immunity and have been found to have antimicrobial activity, specifically against gram-negative bacteria. Cathelicidins are stored in neutrophil granules as propeptides (lacking antimicrobial activity), with neutrophil activation leading to elastase-mediated endoproteolytic cleavage and generation of the C-terminal antimicrobial peptide. The human cathelicidin, referred to alternatively as FALL-39, hCAPI8. LL-37, or CAMP, in its processed (active) form is a 37-amino acid amphiphilic α-helical cationic peptide (see Zanetti, Gennaro and Romeo. 1995, *FEBS Letters* 374: 1-5). Cathelicidin-derived peptides that can be employed in the antimicrobial construct described herein are described in Travis, S., et al. 2000 *Infect Immun*, Vol. 68(5): 2748-2755, herein incorporated by reference in its entirety.

An antimicrobial peptide can also be a peptidomimetic. As used herein, the term "peptidomimetic" is used broadly to mean a peptide-like molecule that has substantially the activity of the corresponding peptide. Peptidomimetics include chemically modified peptides, peptide-like molecules containing non-naturally occurring amino acids, peptoids and the like, have the selective homing activity and the high toxicity of the peptide from which the peptidomimetic is derived (see, for example, "Burger's Medicinal Chemistry and Drug Discovery" 5th ed., vols. 1 to 3 (ed. M. E. Wolff: Wiley Interscience 1995), which is incorporated herein by reference). For example, D amino acids can be advantageously included in the antimicrobial peptide portion of a chimeric peptide of the invention. Peptidomimetics provide various advantages over a peptide, including increased stability during passage through the digestive tract and, therefore, can be advantageously used as oral therapeutics.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystalloqr. Section B, 35:2331 (1979)). This structural depository is continually updated as new crystal structures are determined and can be screened for compounds having suitable shapes, for example, the same shape as an antimicrobial peptide, as well as potential geometrical and chemical complementarity to a target molecule bound by a tumor homing peptide. Where no crystal structure of an antimicrobial peptide is available, a structure can be generated using, for example, the program CONCORD (Rusinko et al., J. Chem. Inf Comput. Sci. 29:251 (1989)). Another database, the Available Chemicals Directory (Molecular Design Limited, Informations Systems, San Leandro Calif.), contains about 100,000 compounds that are commercially available and also can be searched to identify potential peptidomimetics of an antimicrobial peptide.

Small Molecules

In some embodiments, the antimicrobial agent used in the antimicrobial construct described herein, is a small molecule. Small molecules having antimicrobial activity are described in U.S. Pat. Nos. 8,367,680, 8,835,476, 9,119,857; and PCT Published Application No. WO 2001/066147, each of which is herein incorporated by reference in its entirety.

In some embodiments, the small molecule is an antibiotic (i.e., used for the treatment of bacterial infections). In some embodiments, the small molecule is an antibiotic for gram-positive bacteria, wherein delivery with a membrane interacting peptide described herein results in efficacy of the antibiotic against gram-negative bacteria. In some embodiments, the small molecule is an antibiotic for gram-negative bacteria, wherein delivery with a membrane interacting peptide described herein results in enhanced efficacy (e.g., bactericidal activity) of the antibiotic relative to the antibiotic without the membrane interacting peptide.

In some embodiments, broad spectrum antibiotics are employed, including but not limited to beta-lactams (including but not limited to penicillins), cephalosporins, macrolides, tetracyclines, lincosamides, and aminoglycosides. In some embodiments, the antibiotic is linezolid, rifampin, mupirocin, erythromycin, clarithromycin, retapamulin, novobiocin, or fusidic acid. In some embodiments, the antibiotic is of the tetracycline class or sulfonamide class. In some embodiments, the antibiotic is of the quinolone class. In some embodiments, the antibiotic is colistin. In some embodiments, a combination of antibiotics is employed in the antimicrobial construct described herein. A review of studies combining aminoglycosides and beta-lactams is provided in Lador, P. et al., 2014 *Cochrane Database of Systematic Reviews*, Issue 1, Art. No. CD003344, herein incorporated by reference in its entirety. Lang, B. et al. also reviewed combinations of antibiotics in cystic fibrosis patients infected with *P. aeruginosa* (Lang, B. et al 2000 *American Journal of Respiratory and Critical Care Medicine*, Vol. 162(6): 2241-2245, herein incorporated by reference in its entirety). Non limiting examples of antibiotic combinations include: tobramycin and meropenem; tobramycin and piperacillin/tazobactam; tobramycin and ciprofloxacin; meropenem and ciprofloxacin; meropenem and tobramycin; and meropenem and cefipime.

Targeting Moiety

In some embodiments, the antimicrobial construct described herein comprises a targeting moiety. In some embodiments, the targeting moiety targets the construct to a specific tissue. In some embodiments, the targeting moiety targets the construct to a specific microbe (e.g., gram-negative bacteria).

Moieties that target the construct to a specific tissue can be determined by those of skill in the art. For example, where a tissue exhibits a tissue-specific receptor or ligand, the antimicrobial construct can contain the corresponding ligand or receptor to deliver the construct to the tissue. In some embodiments, the antimicrobial construct comprises pHLIP, shown to target regions of lung injury associated with influenza infection (see Li, N. et al. 2013 *Future Microbiol*, Vol. 8(2): 259-69, herein incorporated by reference in its entirety). In some embodiments, the antimicrobial construct comprises Lyp-1, the ligand for stress response protein p32 (see Hamazah, J. et al., 2011 *Proc Natl Acad Sci USA*, Vol. 108(17): 7154-7159, describing use of Lyp-1 in targeting compounds into atherosclerotic plagues and herein incorporated by reference in its entirety).

Moieties that target the construct to a specific microbe can be determined by those of skill in the art. For example, in some embodiments, the target moiety drives localization to a specific microbe. In some embodiments, microbes with specific peptides on their surface can be selectively targeted using at least one moiety that binds to a microbe specific peptide. In some embodiments, the microbe specific peptide is not expressed on mammalian cells. In some embodiments, the microbe specific peptide is expressed minimally on mammalian cells relative to expression on the microbe of interest. In some embodiments, the moiety targets the construct to a fungus. Exemplary peptides that bind to the fungus *Candida albicans* are described in Anandakumar, S. et al. PLoS ONE 2011; 6(2): e16868, incorporated herein by reference in its entirety. In some embodiments, the moiety targets the construct to parasite. Exemplary peptides that bind *Leishmania* are described in Rhaeim R B and Houimel M, Acta Trop 2016 July; 159: 11-9, incorporated herein by reference in its entirety. In some embodiments, the moiety targets the construct to a virus. Exemplary peptides that bind the avian influenza A virus (HPAI) are described in Wu, D. et al. PLoS ONE 2011; 6(8): e23058, incorporated herein by reference in its entirety. In some embodiments, the moiety targets the construct to bacteria. In some embodiments, the moiety targets the construct to gram-positive bacteria. In some embodiments, the moiety targets the construct to gram-negative bacteria. For example, P9b specifically binds to the cell surface of *P. aeruginosa* (see Carnazza, S. et al. 2008 *Biosensors and Bioelectronics*, Vol. 23: 1137-1144, herein incorporated by reference in its entirety). Therefore, in some embodiments, the antimicrobial construct comprises P9b.

Linkers

In some embodiments, the antimicrobial construct comprises a membrane interacting peptide conjugated to an antimicrobial agent via a linker. In some embodiments, the antimicrobial construct comprises a membrane interacting peptide conjugated to a carrier via a linker. In some embodiments, the antimicrobial construct comprises an antimicrobial agent conjugated to a carrier via a linker. In some embodiments, the antimicrobial construct further comprises a targeting moiety which is conjugated to a membrane interacting peptide, a carrier, or an antimicrobial agent via a linker.

The components of the antimicrobial construct described herein can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other.

Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate). Preferably the cross-linking of two proteins will not interfere or significantly interfere with the function of the proteins (e.g., antimicrobial activity). One of skill in the art is well aware of methods to evaluate the activity of cross-linked proteins, such as cross-linked antimicrobial constructs, including the functional studies exemplified in the working examples.

In some embodiments, exemplary linkers include gly-ser polypeptide linkers, glycine-proline polypeptide linkers, and proline-alanine polypeptide linkers. In a certain embodiment, the linker is a gly-ser polypeptide linker, i.e., a peptide that consists of glycine and serine residues.

Exemplary gly-ser polypeptide linkers comprise the amino acid sequence Ser(Gly$_4$Ser)n. In one embodiment, n=1. In one embodiment, n=2. In another embodiment, n=3, i.e., Ser(Gly$_4$Ser)3. In another embodiment, n=4, i.e., Ser(Gly$_4$Ser)4. In another embodiment, n=5. In yet another embodiment, n=6. In another embodiment, n=7. In yet another embodiment, n=8. In another embodiment, n=9. In yet another embodiment, n=10. Another exemplary gly-ser polypeptide linker comprises (Gly$_4$Ser)n. In one embodiment, n=1. In one embodiment, n=2. In a certain embodiment, n=3. In another embodiment, n=4. In another embodiment, n=5. In yet another embodiment, n=6. Another exemplary gly-ser polypeptide linker comprises (Gly$_3$Ser)n. In one embodiment, n=1. In one embodiment, n=2. In a certain embodiment, n=3. In another embodiment, n=4. In another embodiment, n=5. In yet another embodiment, n=6.

In some embodiments, linkers that are used in antibody-drug conjugates are employed in the antimicrobial construct described herein, including disulfide linkers. J. McCombs and S. Owen review linker chemistry in antibody-drug conjugates in McCombs, J. and Owen, S. 2015, *The AAPS Journal*, Vol. 17(2): 339-351, herein incorporated by reference in its entirety.

In some embodiments, the antimicrobial construct described herein employs an esterase sensitive linker. Y. Yang et al. review these enzymes and linkers in Yang, Y., et al. 2011 *Acta Pharmaceutica Sinica B*, Vol. 1(3): 143-159, herein incorporated by reference in its entirety.

Methods of Making the Antimicrobial Construct

In some embodiments, the antimicrobial construct described herein is made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The methods of making antimicrobial constructs also include a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be suitable for use in the methods disclosed herein. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

The nucleic acid molecules described herein can be contained within a vector that is capable of directing their expression in, for example, a cell that has been transduced with the vector. Accordingly, in addition to antimicrobial constructs, expression vectors containing a nucleic acid molecule encoding a mutant and cells transfected with these vectors are among the certain embodiments.

Vectors suitable for use include T7-based vectors for use in bacteria (see, for example, Rosenberg et al., Gene 56: 125, 1987), the pMSXND expression vector for use in mammalian cells (Lee and Nathans, J. Biol. Chem. 263:3521, 1988), and baculovirus-derived vectors (for example the expression vector pBacPAKS from Clontech, Palo Alto, Calif.) for use in insect cells. The nucleic acid inserts, which encode the antimicrobial construct in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance ($neo^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes an antimicrobial construct are also suitable for use. A cell is a transfected cell, i.e., a cell into which a nucleic acid molecule, for example a nucleic acid molecule encoding an antimicrobial construct, has been introduced by means of recombinant DNA techniques. The progeny of such a cell are also considered suitable for use in the methods disclosed herein.

The precise components of the expression system are not critical. For example, an antimicrobial construct can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed antimicrobial constructs can be purified from the expression system using routine biochemical procedures, and can be used, e.g., as therapeutic agents, as described herein.

Formulations

In certain embodiments, the disclosure provides for a composition formulated for in vivo delivery, comprising an antimicrobial construct described herein, and a carrier. In some embodiments, the membrane interacting peptide of the antimicrobial construct is conjugated to the carrier. In some embodiments, the antimicrobial agent of the construct is conjugated to the carrier. In some embodiments, antimicrobial construct, comprising a membrane interacting peptide conjugated to an antimicrobial agent, wherein either the membrane interacting peptide, antimicrobial agent, or both, is conjugated to a carrier. In some embodiments, the membrane interacting peptide and antimicrobial agent are conjugated to a carrier without being conjugated to each other.

In some embodiments, the composition comprises an antimicrobial construct comprising a membrane interacting peptide, a targeting moiety, and an antimicrobial agent. In some embodiments, the targeting moiety is conjugated to the carrier. In some embodiments, the targeting moiety is conjugated to the membrane interacting peptide, which is conjugated to the carrier. In some embodiments, the targeting moiety is conjugated to the antimicrobial agent, which is conjugated to the carrier. In some embodiments, the membrane interacting peptide, targeting moiety and antimicrobial agent are conjugated to the carrier, without being conjugated to each other.

In some embodiments, the composition comprises a plurality of membrane interacting peptides conjugated to a single carrier. In some embodiments, the composition comprises at least one membrane interacting peptide conjugated to a first carrier, and an antimicrobial agent conjugated to a second carrier. In some embodiments, the first and second carriers are co-formulated. In some embodiments, the composition comprises a plurality of antimicrobial agents conjugated to a single carrier.

In some embodiments, the carrier is a porous silicon nanoparticle, a lipid nanoparticle, a polymer nanoparticle or a liposome. Nanoparticles have been developed as sustained release vehicles used in the administration of small molecule drugs as well as protein and peptide drugs and nucleic acids. The drugs are typically encapsulated in a polymer matrix which is biodegradable and biocompatible. As the polymer is degraded and/or as the drug diffuses out of the polymer, the drug is released into the body. Typically, polymers used in preparing these particles are polyesters such as poly(lactide-co-glycolide) (PLGA), polyglycolic acid, poly-beta-hydroxybutyrate, polyacrylic acid ester, etc. These particles can also protect the drug from degradation by the body. Furthermore, these particles can be administered using a wide variety of administration routes. Various types of materials used for synthesizing nanoparticle drug carriers have been disclosed, for example, in US. Pat. No. 2011/0300219, incorporated herein by reference. Amphiphilic compound assisted nanoparticles for targeted delivery have been disclosed, for example, in US. Pat. Publication No. 2010/0203142, incorporated herein by reference.

A "polymer," as used herein, refers to a molecular structure comprising one or more repeat units (e.g. monomers), connected by covalent bonds. The repeat units may be identical, or in some cases, there may be more than one type of repeat unit present within the polymer. Polymers may be obtained from natural sources or they may be chemically synthesized. In some cases, the polymer is a biopolymer, such as a polysaccharide, polypeptide or polynucleotide. Biopolymers may comprise naturally-occurring monomers or derivatives or analogs thereof, for example, derivatives or analogs comprising modified sugars, nucleotides or amino acids. Several such modifications are known to those skilled in the art. In some cases, the polymer is a synthetic polymer, such as polylactide (PLA), polyglycolide (PGA), or poly (lactide-co-glycolide) (PLGA) or poly($\varepsilon$-caprolactone) (PCL).

Since the nanoparticle will be exposed to bodily tissues, it is preferable that the nanoparticle comprises a biocompatible polymer, for example, the polymer does not induce a significant adverse response when administered to a living subject, for example, it can be administered without causing significant inflammation, irritation and/or acute rejection by the immune system.

In some embodiments, the biocompatible polymer is biodegradable, for example, the polymer is able to degrade, chemically and/or biologically, within a physiological environment, such as when exposed to a body tissue. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of hours, days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

Non-limiting examples of biodegradable polymers include, but are not limited to, polysaccharides, polynucleotides, polypeptides, poly(lactide) (or poly(lactic acid)), poly(glycolide) (or poly(glycolic acid)), poly(orthoesters), poly(caprolactones), polylysine, poly(ethylene imine), poly (acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In certain embodiments, copolymers may contain poly(ester-ether)s, e.g., polymers having repeat units joined by ester bonds (e.g., R—C(O)—O—R' bonds) and ether bonds (e.g., R—O—R' bonds). In some embodiments, the nanoparticle may further include a polymer able to reduce immunogenicity, for example, a poly(alkylene glycol) such as poly(ethylene glycol) ("PEG"). The amount of polymer (e.g., PEG) in the nanoparticle should be limited however, so as not to substantiality compromise the tunability of the nanoparticles, which is enhanced by selection of a polymer with a backbone having multiple functional groups per monomer unit, such as a polysaccharide, as compared to PEG which has only reactive functional group per polymer chain. In some embodiments, the nanoparticle composition is free of PEG.

In some embodiments, the carrier is a dextran molecule. In some embodiments, the dextran molecule has a high molecular weight (40 kDa). Among the natural polymers, dextran is a colloidal, hydrophilic, and nontoxic polysaccharide composed of linear α-1,6-linked D-glucopyranose residues with a low fraction of -1,2, -1,3 and -1,4 linked side chains. Dextran can be biodegraded by dextranase, which exists in mammalian (including human) tissues. Engineering dextran-based scaffolds for drug delivery is further described in Sun, G. and Mao, J. 2012 *Nanomedicine (Lond)*, Vol. 7(11): 1771-1784, herein incorporated by reference in its entirety.

In some embodiments, the disclosure provides for a composition comprising an antimicrobial construct, wherein membrane interacting peptides are conjugated to a first dextran molecule, and antimicrobial agents are conjugated to a second dextran molecule. In some embodiments, the dextran molecules are co-formulated together. In some embodiments, the dextran molecules are co-formulated in a porous silicon nanoparticle, a lipid nanoparticle, a polymer nanoparticle or a liposome. In some embodiments, the dextran molecules are formulated in separate compositions and are co-administered. In some embodiments, the membrane interacting peptide(s) and antimicrobial agent(s) are conjugated to the same dextran molecule.

In some embodiments, the disclosure provides for a composition comprising an antimicrobial construct described herein formulated in a porous silicon nanoparticle, a lipid nanoparticle, a polymer nanoparticle or a liposome.

In certain embodiments, the disclosure provides for a pharmaceutical composition comprising an antimicrobial construct with a pharmaceutically acceptable diluents, carrier, solubilizer, emulsifier, preservative and/or adjuvant.

In certain embodiments, the membrane interacting peptide and antimicrobial agent can be formulated in separate compositions.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the antimicrobial construct.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an antimicrobial construct can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an antimicrobial construct can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising the antimicrobial construct in a pharmaceutically acceptable vehicle. In certain embodiments, a vehicle for parenteral injection is sterile distilled water in which antimicrobial constructs are formulated as a sterile, isotonic solution, and properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments the antimicrobial construct can be formulated as a dry powder for inhalation. In certain embodiments, an inhalation solution comprising the antimicrobial construct can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, the antimicrobial construct that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of the antimicrobial construct. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of antimicrobial construct in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving the antimicrobial construct, in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, the effective amount of a pharmaceutical composition comprising the antimicrobial construct to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the antimicrobial construct is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of the antimicrobial construct in the formulation used. In certain embodiments, a clinician will administer the composition until a dosage is reached that achieves the desired effect. In certain embodiments, the composition can therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intraocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising the antimicrobial construct in an ex vivo manner. In such instances, cells, tissues and/or organs that have been removed from the patient are exposed to a pharmaceutical composition comprising the antimicrobial construct, after which the cells, tissues and/or organs are subsequently implanted back into the patient.

In certain embodiments, the antimicrobial construct can be delivered by implanting certain cells that have been genetically engineered, using methods such as those described herein, to express and secrete the antimicrobial constructs. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Exemplary Antimicrobial Constructs

The antimicrobial constructs of the disclosure are modular, and can be configured to incorporate various individual domains (i.e., membrane interacting peptides, antimicrobial agents, and targeting moieties). For example, in some embodiments, the antimicrobial construct may include the lactoferrin-derived peptide set forth in SEQ ID NO: 1. in some embodiments, the antimicrobial construct may include the WLBU2 protein set forth in SEQ ID NO: 27. In some embodiments, the antimicrobial construct may include the LBU1 protein set forth in SEQ ID NO: 24. In some embodiments, the antimicrobial construct may include the WLBU1 protein set forth in SEQ ID NO: 25. In some embodiments, the antimicrobial construct may include the LBU2 protein set forth in SEQ ID NO: 26. In some embodiments, the antimicrobial construct may include the dKK peptide set forth in SEQ ID NO: 34. In some embodiments, the antimicrobial construct may include linezolid. In some embodiments, the antimicrobial construct may include the P9b peptide set forth in SEQ ID NO: 28.

It will be understood to the skilled artisan that these individual peptides can be coupled to each other in any order to form an antimicrobial construct. For example, as detailed in the specific examples below, the lactoferrin-derived peptide can be coupled to the dKK peptide. In another example, the lactoferrin-derived peptide can be coupled to linezolid. In yet another example, the WLBU2 peptide can be coupled to the dKK peptide. In another example, the WLBU2 peptide can be coupled to linezolid. In another example, the P9b peptide can be coupled to the WLBU2 peptide to form a P9b-WLBU2 tandem peptide. In another example, the P9b-WLBU2 tandem peptide can be coupled to linezolid. In another example, the P9b-WLBU2 tandem peptide can be coupled to the dKK peptide.

In some embodiments, the antimicrobial construct further comprises a carrier. In some embodiments, the carrier is a porous silicon nanoparticle (pSiNP). In one example, the lactoferrin-derived peptide is coupled to the dKK peptide, and formulated in a pSiNP. In another example, multiple lactoferrin-derived peptides are coupled to the dKK peptide and formulated in a pSiNP. In another example, the lactoferrin-derived peptide is coupled to multiple dKK peptides and formulated in a pSiNP. In another example, multiple lactoferrin-derived peptides are coupled to multiple dKK peptides and formulated in a pSiNP. In another example, the lactoferrin-derived peptide is coupled to linezolid, and formulated in a pSiNP. In another example, multiple lactoferrin-derived peptides are coupled to linezolid and formulated in a pSiNP. In another example, the lactoferrin-derived peptide is coupled to multiple linezolid molecules and formulated in a pSiNP. In another example, multiple lactoferrin-derived peptides are coupled to multiple linezolid molecules and formulated in a pSiNP. In another example, the WLBU2 peptide is coupled to linezolid, and formulated in a pSiNP. In another example, multiple WLBU2 peptides are coupled to linezolid and formulated in a pSiNP. In another example, the WLBU2 peptide is coupled to multiple linezolid molecules and formulated in a pSiNP. In another example, multiple WLBU2 peptides are coupled to multiple linezolid molecules and formulated in a pSiNP. In another example, the WLBU2-P9b tandem peptide is coupled to linezolid, and formulated in a pSiNP. In another example, multiple WLBU2-P9b tandem peptides are coupled to linezolid and formulated in a pSiNP. In another example, the WLBU2-P9b tandem peptide is coupled to multiple linezolid molecules and formulated in a pSiNP. In another example, multiple WLBU2-P9b tandem peptides are coupled to multiple linezolid molecules and formulated in a pSiNP. In another example, the lactoferrin-derived peptide (s), WLBU2 peptide(s), or WLBU2-P9b tandem peptide(s) are formulated in a first pSiNP, and the dKK peptide or linezolid are formulated in a second pSiNP. In some embodiments, the first and second pSiNPs are formulated into a single composition.

In some embodiments, the antimicrobial construct further comprises a carrier, wherein the carrier is a dextran molecule. In one example, the lactoferrin-derived peptide is coupled to the dKK peptide, and the lactoferrin-derived peptide is coupled to a dextran molecule. In one example, the lactoferrin-derived peptide is coupled to the dKK peptide, and the dKK peptide is coupled to a dextran molecule. In one example, the lactoferrin-derived peptide and dKK peptide are separately coupled to a dextran molecule without being coupled to each other. In another example, the lactoferrin-derived peptide is coupled to a first dextran molecule, and the dKK peptide is coupled to a second dextran molecule. In one example, the first and second dextran molecules are formulated into the same pSiNP. In another example, the first and second dextran molecules are formulated into separate pSiNPs.

In another example, the WLBU2 peptide is coupled to linezolid, and the WLBU2 peptide is coupled to a dextran molecule. In another example, the WLBU2 peptide is coupled to linezolid, and the linezolid is coupled to a dextran molecule. In another example, multiple WLBU2 peptides are coupled to linezolid, and the multiple WLBU2 peptides are coupled to a dextran molecule. In another example, multiple WLBU2 peptides are coupled to linezolid, and the linezolid is coupled to a dextran molecule. In another example, the WLBU2 peptide is coupled to multiple linezolid molecules, and the WLBU2 peptide is coupled to a dextran molecule. In another example, the WLBU2 peptide is coupled to multiple linezolid molecules, and the multiple linezolid molecules are coupled to a dextran molecule. In another example, multiple WLBU2 peptides are coupled to multiple linezolid molecules, and the multiple WLBU2 peptides are coupled to a dextran molecule. In another example, multiple WLBU2 peptides are coupled to multiple linezolid molecules, and the multiple linezolid molecules are coupled to a dextran molecule. In one example, the WLBU2 peptide or multiple WLBU2 peptides, and linezolid or multiple linezolid molecules, are separately coupled to a dextran molecule without being coupled to each other. In one example, the WLBU2 peptide, or multiple WLBU2 peptides, are coupled to a first dextran molecules, and the linezolid, or multiple linezolid molecules are coupled to a second dextran molecules. In one example, the first and second dextran molecules are formulated into the same pSiNP. In another example, the first and second dextran molecules are formulated into separate pSiNPs.

In another example, the WLBU2-P9b tandem peptide is coupled to linezolid, and the WLBU2-P9b tandem peptide is coupled to a dextran molecule. In another example, the WLBU2-P9b tandem peptide is coupled to linezolid, and the linezolid is coupled to a dextran molecule. In another example, multiple WLBU2-P9b tandem peptides are coupled to linezolid, and the multiple WLBU2-P9b tandem peptides are coupled to a dextran molecule. In another example, multiple WLBU2-P9b tandem peptides are coupled to linezolid, and the linezolid is coupled to a dextran molecule. In another example, the WLBU2-P9b tandem peptide is coupled to multiple linezolid molecules, and the WLBU2-P9b tandem peptide is coupled to a dextran molecule. In another example, the WLBU2-P9b tandem peptide is coupled to multiple linezolid molecules, and the multiple linezolid molecules are coupled to a dextran molecule. In another example, multiple WLBU2-P9b tandem peptides are coupled to multiple linezolid molecules, and the multiple WLBU2-P9b tandem peptides are coupled to a dextran molecule. In another example, multiple WLBU2-P9b tandem peptides are coupled to multiple linezolid molecules, and the multiple linezolid molecules are coupled to a dextran molecule. In one example, the WLBU2-P9b tandem peptide or multiple WLBU2-P9b tandem peptides, and linezolid or multiple linezolid molecules, are separately coupled to a dextran molecule without being coupled to each other. In one example, the WLBU2-P9b tandem peptide, or multiple WLBU2-P9b tandem peptides, are coupled to a first dextran molecules, and the linezolid, or multiple linezolid molecules are coupled to a second dextran molecules. In one example, the first and second dextran molecules are formulated into the same pSiNP. In another example, the first and second dextran molecules are formulated into separate pSiNPs.

Kits

A kit can include an antimicrobial construct, as disclosed herein, and instructions for use. The kit may comprise, in a suitable container, an antimicrobial construct, one or more controls, and various buffers, reagents, enzymes and other standard ingredients well known in the art. Certain embodiments include a kit with an antimicrobial construct and a carrier in the same vial. In certain embodiments, a kit includes an antimicrobial construct and a carrier in separate vials. In some embodiments, a kit includes the components of an antimicrobial construct and instructions for generating the antimicrobial construct. For example, in some embodiments, a kit comprises the membrane interacting peptide and antimicrobial agent in separate vials. In some embodiments, a kit comprises the membrane interacting peptide, antimicrobial agent, and targeting moiety in separate vials.

The container can include at least one vial, well, test tube, flask, bottle, syringe, or other container means, into which an antimicrobial construct and carrier, may be placed, and in some instances, suitably aliquoted. Where an additional component is provided, the kit can contain additional containers into which this component may be placed. The kits can also include a means for containing an antimicrobial construct, and any other reagent containers in close confinement for commercial sale. Such containers may include injection or blow-molded plastic containers into which the desired vials are retained. Containers and/or kits can include labeling with instructions for use and/or warnings.

Methods of Use

The effect of the antimicrobial constructs described herein on the viability of prokaryotic and eukaryotic cells may be assayed by any method that determines survival after treatment or exposure to the peptides. For screening purposes, in some embodiments, standard bacterial broth dilution assays are used and can be compared with red blood cell lysis assays (see Tencza et al., 1999, *Journal of Antimicrobial Chemotherapy* 44:33-41). However, ultimately this selective toxicity comparison should be performed when both prokaryotic and eukaryotic cells are exposed to peptide under identical conditions. In addition, the effect of the antimicrobial peptides on the viability of other pathogens, including yeast, *mycoplasma* and viruses, may also be tested.

The antibacterial properties of the antimicrobial constructs described herein may be determined, e.g., from a bacterial lysis assay, as well as by other methods, including, inter alia, growth inhibition assays (Blondelie et al., *Biochemistry* 31:12688, 1992), fluorescence-based bacterial viability assays (e.g., Molecular Probes BacLight), flow cytometry analyses (Arroyo et al., *J. Virol.* 69: 4095-4102, 1995), and other standard assays known to those skilled in the art.

Determination of the antifungal properties of the antimicrobial constructs described herein may be performed by techniques well known to those skilled in the art (Selitrennikoff, C., Screening for Antifungal Drugs, in Biotechnology of Filamentous Fungi, Finkelstein et al., eds., Butterworth-Heinemann, Boston, 1992).

Determination of the antiviral properties of the antimicrobial constructs described herein may be performed by techniques well known to those skilled in the art, for example by the ability of a peptide to inhibit viral plaque formation in standard, art recognized, in vitro assays (e.g., Wild et al., *Proc. Natl. Acad. Sci. USA* 89: 10537-10541, 1992).

The assays for growth inhibition of a microbial target can be used to derive a minimum bactericidal concentration (MBC) value for the peptide, i.e., the concentration of peptide required to kill 99.9% (3-log decrease) of the microbial sample being tested. This value is well known to those in the art as representative of the effectiveness of a particular antimicrobial agent (e.g., an antibiotic) against a particular organism or group of organisms. In assays to detect the MBC of a construct, growth inhibition of a bacterial population also can be measured with reference to the number of colony forming units (cfu) after exposure to a construct relative to a control experiment without a peptide.

In some embodiments, the same assays are used to derive a minimum inhibitory concentration (MIC), which is the lowest concentration of an antimicrobial that will inhibit the visible growth of a microorganism after overnight incubation.

Another parameter useful in identifying and measuring the effectiveness of the antimicrobial constructs described herein is the determination of the kinetics of the antimicrobial activity of a construct. Such a determination can be made by performing any of the assays described herein and determining antimicrobial activity as a function of time. In some embodiments, the constructs display kinetics that result in efficient killing of a microorganism. Exemplary kinetics include, but are not limited to, kinetics of pore formation, kinetics of microbe death (e.g., individual bacterial cell death), and binding kinetics of the antimicrobial construct to the microbe of interest. Methods for evaluating such kinetics are known to those of skill in the art.

The antimicrobial constructs described herein display selective toxicity to target microorganisms and minimal toxicity to mammalian cells. Determining the toxicity of the constructs described herein on mammalian cells may be performed using tissue culture assays. For mammalian cells, such assay methods include, inter alia, trypan blue exclusion or MTT assays (see Moore et al., 1994, *Peptide Research* 7:265-269). Where a specific cell type may release a specific metabolite upon changes in membrane permeability, that specific metabolite may be assayed, e.g., the release of hemoglobin upon the lysis of red blood cells (see Srinivas et al., 1992, *Journal of Biological Chemistry* 267:7121-7127). In addition, the disruption of the trans epithelial resistance (Rte) of a cell monolayer that have formed tight junctions can be monitored. The antimicrobial constructs described herein are preferably tested against primary cells, e.g., using human bronchial epithelial (HBE) cells in polarized culture, or other primary cell cultures routinely used by those skilled in the art. Permanently transformed cell lines may also be used, e.g., Jurkat cells.

In determining the therapeutic potential of an antimicrobial construct, a lower MBC and/or MIC for bacterial, fungal, protozoal, or viral samples relative to that observed for mammalian cells defines the therapeutic window and reflects the selective antimicrobial toxicity of the agent. Characterization of the antimicrobial activity of the antimicrobial peptides described herein can be performed using any microorganism that can be cultured and assayed, as above, including bacteria, fungi, protozoa or viruses.

Antibacterial assays for the antimicrobial peptides described herein can be performed to determine the bacterial killing activity toward both gram-positive and gram-negative microorganisms. *E. coli* and *P. aeruginosa* are examples of gram-negative organisms. *S. aureus* may be used as a model of a gram-positive microorganism, and this is a significant clinical target since most strains are refractive to most systemic antibiotic treatments. Methicillin-resistant *S. aureus* may be used as an antibiotic-resistant model organism. *E. faecalis* can be assayed, and in particular, the vancomycin-resistant isolates found in clinical settings, e.g. hospitals. *S. marcescens* is a source of ophthalmic and other topical infections, and can be readily assayed. The constructs may be used in the treatment of external ear infections (otitis externa), or in the treatment of sexually transmitted diseases such as those caused by *Neisseria gonorrhoeae*. Other bacterial pathogens, often found extracellularly on mucosal surfaces, which may be targets for the antimicrobial constructs described herein include, but are not limited to, *Streptococcus pneumonia, Streptococcus pyogenes*, Group B Streptococci, *Gardnerella vaginalis, Klebsiella pneumoniae, Acinetobacter* spp., *Haemophilus aegyptius, Haemophilus influenzae, S. epidermis, Propionibaclerium acnes*, and oral pathogens such as *Actinomyces* spp., *Porphyromonas* spp., and *Prevotella melaminogenicus*. Other microbial pathogens may also be targets for these constructs. These microbial pathogens, and the infections that they cause, are known to those skilled in the art.

*Mycoplasma* spp. belong to the class Mollicutes, eubacteria that appear to have evolved regressibly by genome reduction from gram-positive ancestors. Unlike classic bacteria, they have no cell wall but instead are bounded by a membrane, and may be susceptible to certain antimicrobial constructs described herein. Antimycoplasma assays may be performed to test the antimycoplasma activity of the antimicrobial constructs described herein. *Mycoplasma* human pathogens include *Mycoplasma pneumoniae* (a respiratory pathogen), *Mycoplasma hominis* (a urogenital pathogen) and *Ureaplasma urealyticum* (a urogenital pathogen). The antimicrobial constructs described herein may be used to treat diseases related to *mycoplasma* infection. In addition, *mycoplasma* contamination is a frequent problem in culturing cells in vitro and is very difficult to effectively eliminate. Therefore, the antimicrobial constructs described herein may be useful in selectively eliminating *mycoplasma* contamination in tissue culture.

Certain fungi also are susceptible to the antimicrobial constructs described herein, including members of the medically important *Candida* and *Cryptococcus* genera. The membranes of fungi contain ergosterol, which is not found in human cells. This differentiation may be exploited in therapeutic applications so as to design antimicrobial constructs, which selectively inhibit fungi, yet do not interfere with human or mammalian membrane function. Precedent for a mechanism of selective antifungal membrane targeting is found, for example, in the use of the antifungal agent, amphotericin B, which binds ergosterol and forms pores in the membrane (Goodman et al., The Pharmacological Basis of Therapeutics, Macmillan Publishing, New York, 1985). All fungi can be considered as potential targets of these constructs, including, but not limited to, dermatophytes, yeasts, dimorphic fungi, and filamentous molds. Specific fungal pathogens which may be targets for the antimicrobial peptides described herein, but are not limited to, *Microsporum, Epidermophyton, Candida, Cryptococcus*, and *Trichophyton* genera, *Sporothrix schenkii* and *Aspergillus fumigatus*, as well as other fungal pathogens known to those skilled in the art.

Both DNA and RNA viruses are potential targets of the antimicrobial constructs described herein. In a particular embodiment, an enveloped virus may be susceptible to the antiviral effect of the constructs due to their ability to target and disrupt membrane structures. While all viruses are potential targets, the enveloped viruses, such as poxvirus, herpesvirus, rhabdovirus, hepadnavirus, baculovirus, orthomyxovirus, paramyxovirus, retrovirus, togavirus, bunyavirus and flavivirus, for example and without limitation, may be particularly susceptible to the antimicrobial constructs described herein. In one embodiment, the virus is a lentivirus, such as HIV-1; a herpes virus, such as HSV; or an orthomyxovirus, such as an influenza virus. In one embodiment, the virus is HIV-1. The spread of this virus on a mucosal surface might be manipulated by the topical administration of an antimicrobial constructs described herein. In another embodiment, the virus is an orthomyxovirus, for example an influenza virus.

The constructs described herein are useful for inhibiting or treating a particular microbial infection, such as, but not limited to, cystic fibrosis lung infection, joint sepsis, ocular infections, periodontal disease, STDs, otitis extema, cutaneous infections, burn infections, vaginal infections, Candidiasis, and diabetic foot ulcers.

Furthermore, the antimicrobial constructs described herein may be useful to inhibit microbial colonization. For example, the constructs may be delivered prophylactically and expressed by eukaryotic cells in vivo, via transfection using viral vectors. The continued expression of the constructs in the cells and secretion into their environment may interfere with colonization of microbes and prevent microbial infection. This may be particularly useful to prevent infections associated with cystic fibrosis by delivering the antimicrobial constructs to airway epithelial cells. The constructs may inhibit colonization of bacteria involved in cystic fibrosis. Cells expressing the constructs may be able to continuously combat the colonization of a range of pathogenic microbes.

In the treatment of cystic fibrosis or other airway diseases (e.g., infectious diseases or conditions), an antimicrobial construct described herein may be administered by aerosol in an amount and in a dosage regimen effective to prevent and/or treat a microbial infection, such as an infection by a bacterial, fungal or viral agent. In one embodiment, the dosage form comprises one or more antimicrobial peptides as described herein in hypotonic saline, which is commonly used to loosen sputum in cystic fibrosis patients. In the treatment of cystic fibrosis, a combination dosage form comprising the constructs along with another therapeutic agent for the treatment of cystic fibrosis also may be utilized. Other active agents that may be combined with the construct include, without limitation, deoxyribonuclease (DNAse, such as dornase alfa (e.g., Pulmozyme), a human DNAse), N-acetylcysteine, albuterol and ipratropium bromide. The constructs or combination dosage forms typically can be packaged as a dosage form in any useful aerosolizing/nebulizing device as are available. The constructs or combination dosage forms may be liquid or powdered solid, for instance, lyophilized. A large number of suitable aerosolization devices are known in the pharmaceutical arts and are appropriate for airway delivery of the antimicrobial constructs alone or in combination with one or more additional active agents.

The evaluation of an antimicrobial construct for inhibiting or treating a particular microbial infection may also involve the use of animal models of infection that are acknowledged by those skilled in the art to be relevant to such infections in a human or other mammal. The Examples infra describe a mouse model of *P. aeruginosa* infection, wherein less than 20% of infected mice live for longer than 24 hours. The antimicrobial constructs described herein increased survival to 24 hours to 100%.

Systemic administration of the antimicrobial constructs described herein may induce an immunogenic response in a host. Therefore, techniques known in the art, such as waxing with polyethylene glycol, may be employed to reduce the immunogenicity of the peptides when administered systemically.

In the context of delivery of the constructs described herein to prevent or treat an infection, an "effective amount" of a given therapeutic agent, compound, etc., is an amount effective to achieve a desired prophylactic or therapeutic goal in a patient. In the context of a prevention or treatment of an infection by an infectious agent, such as a bacterial, fungal or viral agent, this means that either infection is prevented and/or ameliorated by the agent as compared to a negative control (without the construct). The status of any disease or condition may be monitored by any suitable method known to those in the medical arts, including, without limitation, those methods described herein.

The precise effective amount of constructs to be used in the methods described herein to control infection can be determined without undue experimentation by those skilled in the art who understand the nature of the activity of antibiotics and the nature of an infectious process. The amount of an antibiotic construct that must be utilized can vary with the magnitude of the infection and the microorganism to be treated. The amount of an antimicrobial construct described herein per unit volume of combined medication for administration may also be determined without undue experimentation by those skilled in the art. However, it can generally be stated that the peptides should preferably be present in an amount of at least about 1.0 nanogram per milliliter of combined composition, more preferably in an amount up to about 1.0 milligram per milliliter. Systemic dosages also depend on the age, weight and conditions of the patient and on the administration route. For example, a suitable dosage for the administration to adult humans can range from about 0.01 to about 100 mg per kilogram body weight. The preferred dosage can range from about 0.5 to about 5.0 mg per kilogram body weight. As used herein, a physiologically acceptable carrier includes any and all solvents, dispersion media, coatings, and the like. The use of such media and agents are well known in the art.

Because the antimicrobial construct compositions described herein are designed to eliminate an ongoing infectious process, a continual application or periodic reapplication of the compositions may be indicated and preferred.

Unless otherwise indicated, conventional techniques of synthetic organic chemistry, protein chemistry, molecular biology, microbiology, recombinant DNA technology, and pharmacology, which are within the skill of the art, may be used in practicing any embodiment of the methods, compositions and compounds described herein. Such techniques are explained fully in the literature (See, e.g., Scopes, R. K. Protein Purification: Principles and Practices, 2nd edition, Springer-Verlag, 1987; Methods in Enzymology, S. Colwick and N. Kaplan, editors, Academic Press; Sambrook et al., Molecular Cloning: A Laboratory Manual, 2nd edition, Cold Spring Harbor Press, Cold Spring Harbor, N.Y.; Ausubel et al., Current Protocols in Molecular Biology, John Wiley and Sons, New York, 1995; Remington's Pharmaceutical Sciences, 17th ed., Mack Publishing Co., Easton, Pa., 1985).

EXAMPLES

Example 1: Selection of *Pseudomonas*-Specific Antimicrobial Construct

To address the challenges associated with antibiotic development, nanomaterials were engineered for anti-bacterial activity using two design principles to increase localization and therefore efficacy. First, a screen was performed using a library of bifunctional peptides that can localize to bacterial membranes and deliver a toxic payload to select for agents that can specifically kill *P. aeruginosa* over off-target host cells. Second, cargo was protected in biodegradable porous silicon nanoparticles (pSiNPs) for controlled-release of the peptide payload in lung tissue. Together, these elements combine to form an anti-infective nanomaterial that was applied to a *P. aeruginosa* lung infection model (FIG. 1A). This work demonstrates that anti-infective nanomaterial can significantly decrease bacterial numbers and improve survival of mice in a mouse model of lung infection.

In *P. aeruginosa*, two concentric membrane structures studded with efflux pumps surround the degradative periplasmic compartment, creating a formidable barrier to antibacterial agents. To mediate efficient bacterial interaction, a library of membrane-interacting peptides fused in tandem with a synthetic bacterial toxin, $_D$[KLAKLAK]$_2$ was designed and tested. $_D$[KLAKLAK]2 function is not dependent on its stereochemistry, thus it was synthesized with D-amino acids to limit proteolytic degradation and is referred to as dKK. Since membrane permeability is a significant barrier to the activity of antibiotics in gram-negative bacteria, the peptide library was designed to encompass membrane-interacting peptides in tandem with the toxic dKK cargo. 25 peptides documented to have membrane-active properties were selected and synthesized N-terminally to dKK (22 of the 25 tandem peptides were soluble in water; Table 1). The peptide library was synthesized with FAM-conjugated lysine at the C-terminal end of the membrane-interactive peptide and with or without $_D$[KLAKLAK]$_2$ on the C-terminus by the Koch Institute Swanston Biotechnology Center by standard Fmoc chemistry for initial screening. All peptides were synthesized with N-terminal myristic acid and C-terminal amine. They were resynthesized to 80% purity in small scales for follow up in vitro studies. Large scale peptides for animal studies were synthesized by CPC Scientific to 90% purity.

(KCFQWQRNMRKVRGPPVSCIKR, SEQ ID NO: 1) is from a protein in the transferrin family with known membrane interactions with bacteria. Analysis of physicochemical properties of peptides did not predict relative activity for killing *P. aeruginosa* (Table 1), indicating the need for empirical screening. LACT-dKK was synthesized to higher purity and the dose-response of dKK alone, membrane-active peptide alone, and tandem peptides were tested at concentrations up to 100 μM (FIG. 1C).

Cellular morphology and membranes of *P. aeruginosa* were examined when incubated with LACT-dKK at the MIC for 15 minutes. FIG. 1D shows that membrane blebs were formed. Further, LACT-dKK led to distinctive gross morphological changes relative to untreated bacteria.

Figure 3:
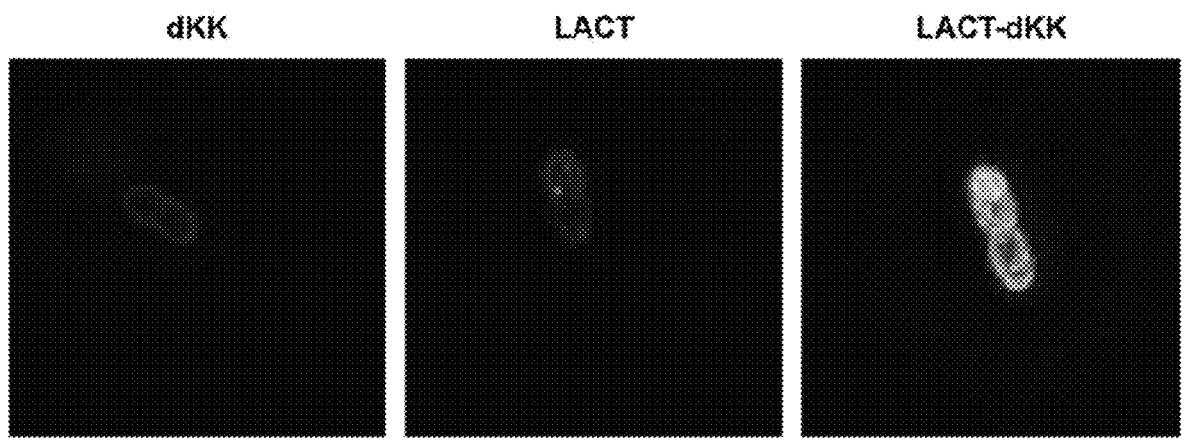
FIG. 3 shows three dimensional structured illumination microscopy of PA01 incubated with dKK, LACT, or LACT-dKK peptides (FAM labeled; green). Membranes were labeled with a lipophilic dye (FM 4-64FX; red).

LACT-dKK was 128-fold more potent than LACT alone and 32-fold more potent than dKK alone, and was able to associate with *P. aeruginosa* (FIG. 3). Three dimensional structured illumination microscopy of PAO1 incubated with dKK, LACT, or LACT-dKK peptides (FAM labeled; green). Membranes were stained with a lipophilic dye (FM 4-64FX; red). 1×10$^8$ CFU/sample were incubated with 1 uM of

TABLE 1

| Name | SEQ ID NO. | Mw | AA | +AA (%) | −AA (%) | pI | AI |
|---|---|---|---|---|---|---|---|
| Lactoferrin | 1 | 2718.3 | 22 | 32 | 0 | 11.6 | 44 |
| S413-PV | 3 | 2377.0 | 20 | 45 | 0 | 11.5 | 117 |
| CecroA + Mel | 4 | 2795.5 | 26 | 19 | 0 | 10.6 | 150 |
| Buforin 2 | 5 | 2434.8 | 21 | 29 | 0 | 12.6 | 88 |
| Magainin | 6 | 2505.9 | 23 | 17 | 4 | 10.0 | 72 |
| Pep1 | 7 | 2848.2 | 21 | 29 | 14 | 9.8 | 14 |
| Melittin | 8 | 2847.4 | 26 | 19 | 0 | 12.0 | 135 |
| GALA | 9 | 3032.4 | 30 | 0 | 23 | 3.8 | 138 |
| Apidaecins | 10 | 2108.4 | 18 | 17 | 0 | 11.7 | 59 |
| Tat | 11 | 1616.9 | 12 | 67 | 0 | 12.3 | 0 |
| KFFKFFKFFK | 12 | 1413.7 | 10 | 40 | 0 | 10.5 | 0 |
| YTA4 | 13 | 1953.4 | 17 | 29 | 0 | 12.0 | 121 |
| M918 | 14 | 2652.3 | 22 | 32 | 0 | 12.4 | 110 |
| Penetratin | 15 | 2246.7 | 16 | 44 | 0 | 12.3 | 49 |
| VP22 | 16 | 3656.0 | 34 | 26 | 0 | 12.9 | 32 |
| HGP | 17 | 3137.6 | 24 | 13 | 8 | 8.5 | 110 |
| Bac7 | 18 | 2938.5 | 24 | 38 | 0 | 12.9 | 49 |
| 6R | 19 | 955.1 | 6 | 100 | 0 | 12.7 | 0 |
| HuT-cell CPP | 20 | 2768.2 | 22 | 50 | 0 | 12.4 | 35 |
| pVEC | 21 | 2209.7 | 18 | 33 | 0 | 12.5 | 141 |
| CADY | 22 | 2622.2 | 13 | 40 | 0 | 12.6 | 147 |
| MAP | 23 | 1877.4 | 18 | 28 | 0 | 10.6 | 185 |

Figure 1B:
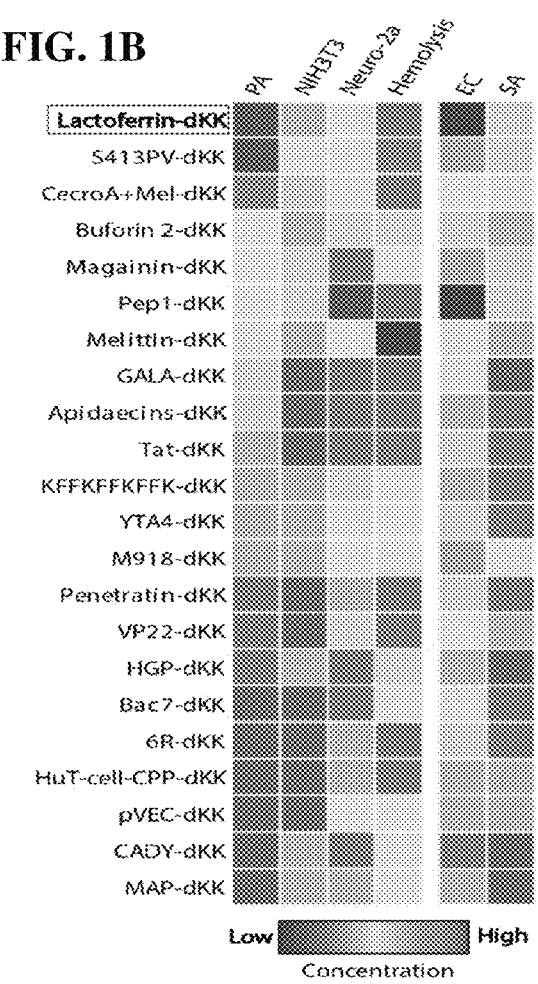
FIG. 1B shows the minimum inhibitory concentration (MIC) required of each peptide candidate to inhibit the growth of *P. aeruginosa* (PA), *E. coli* (EC), and *S. aureus* (SA). Peptide candidates were also evaluated for the level of exposure that leads to 50% lethality (LD50) in NIH3T3 normal fibroblasts and Neuro-2a mouse neuroblastoma cells, and by the concentration required to lyse 50% of red blood cells.
Figure 1C:
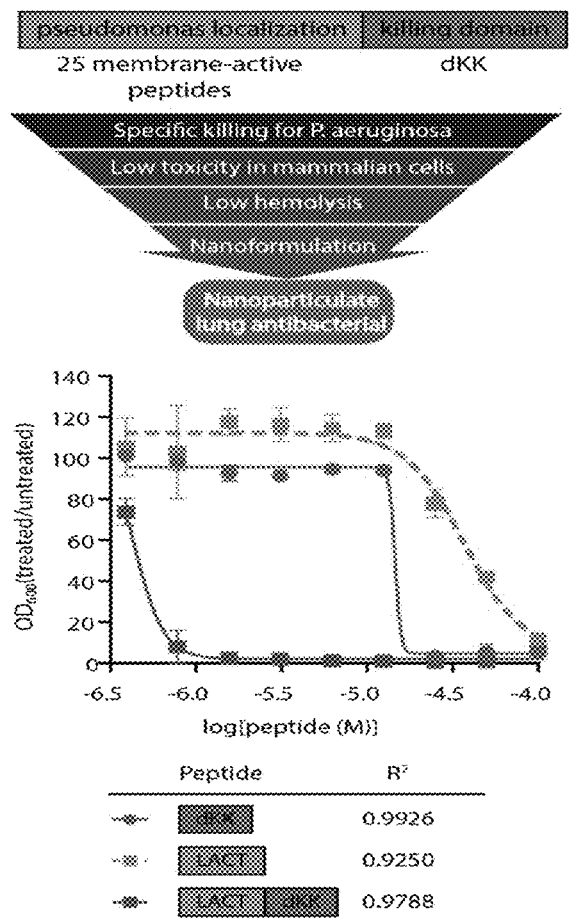
FIG. 1C provides a schematic of the approach used to design and screen tandem peptides with antimicrobial activity against *P. aeruginosa* (top), and a graph showing a MIC assay for individual peptide domains dKK and lactoferrin (LACT), and a LACT-dKK tandem peptide incubated with *P. aeruginosa* (bottom).
Figure 1D:
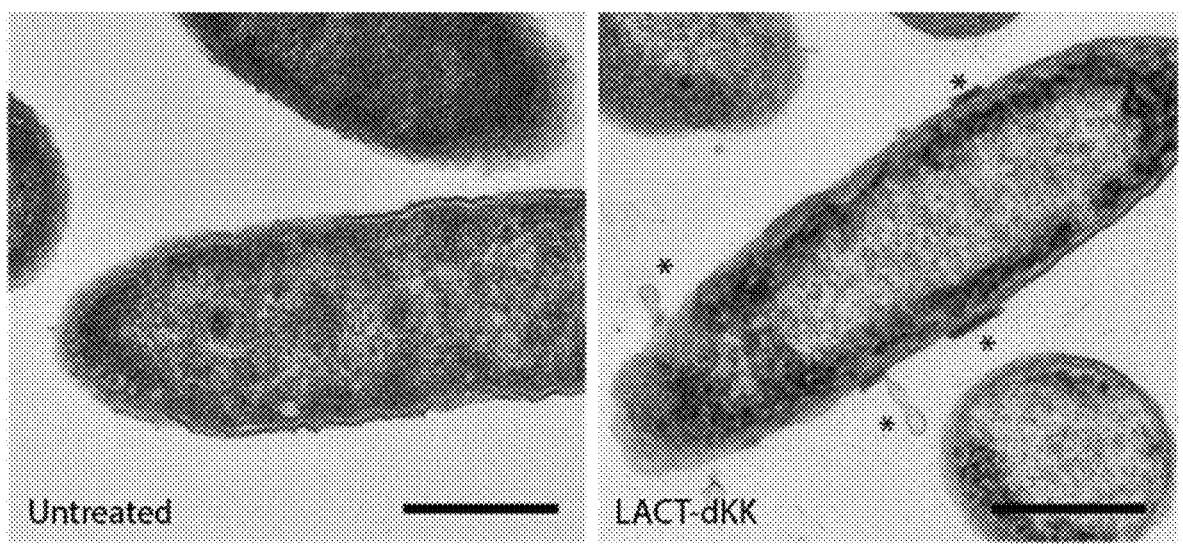
FIG. 1D shows transmission electron microscopy (TEM) images of *P. aeruginosa* untreated (left) and treated with LACT-dKK (right). Stars indicate membrane blebs.
Figure 2:
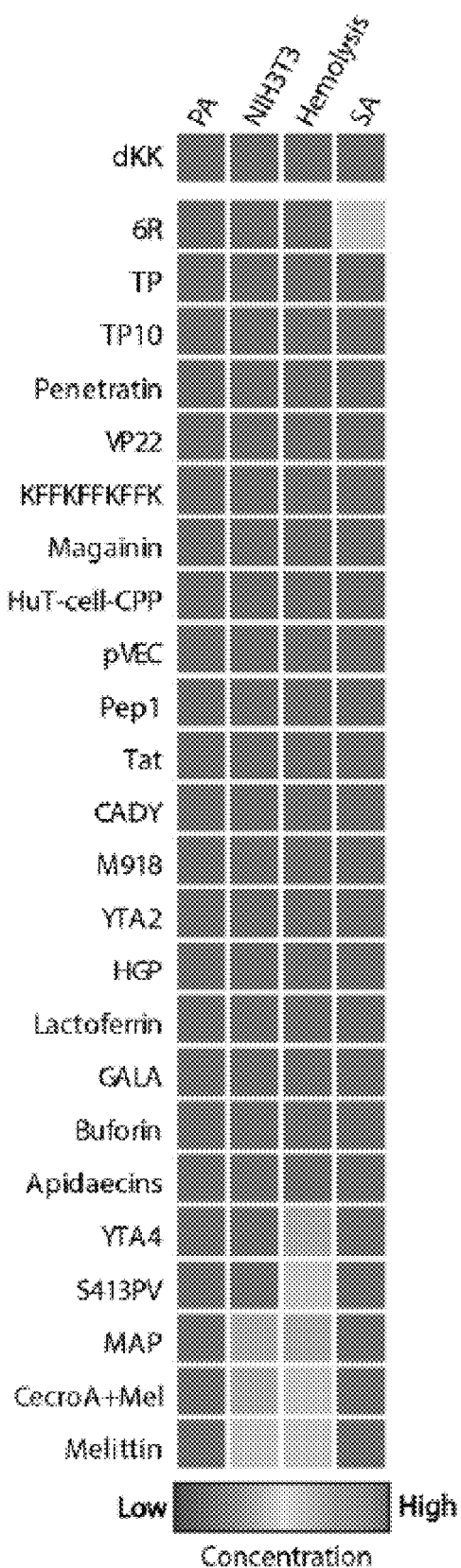
FIG. 2 provides a heatmap showing no membrane-targeting peptides tested had inhibitory activity against bacteria when not in tandem, as measured by *P. aeruginosa* killing, NIH 3T3 toxicity, blood hemolysis, and *S. aureus* killing.

Next, the tandem peptide library was screened using a series of assays to identify agents which mediate specific killing of *P. aeruginosa*, while also exhibiting limited off-target toxicity (FIG. 1B). The minimal inhibitory concentrations (MIC) were measured in *P. aeruginosa* and cell viability in mammalian cells at a peptide concentration range between 0-5 μM. Toxicity was evaluated in NIH 3T3 mouse fibroblasts and Neuro-2a neuroblastoma. To negatively select against tandem peptides that may cause red blood lysis when administered in animals, the peptides were also screened in a hemolysis assay. In the range of concentrations tested, no membrane-active peptide had inhibitory activity against bacteria when not in tandem with dKK (FIG. 2), supporting the rationale of the tandem peptide architecture. At these concentrations, dKK alone also had no activity against *P. aeruginosa* (FIG. 2). Since it is advantageous to identify antibacterial agents which have narrow-spectrum activity, antibacterial efficacy against other gram-negative bacterial species (*E. coli*) and a gram-positive bacterial species (*S. aureus*; FIG. 1B) was also assessed. The best performing tandem peptide was lactoferrin-dKK (LACT-dKK). Lactoferrin peptide LACT, dKK, or LACT-dKK peptide for 90 minutes at 37° C. and stained with the membrane dye FM 4-64FX (ThermoFisher) for 10 minutes at 5 μg/mL. After washing and fixation, samples were mounted with VectaShield (VectorLabs) and imaged on an Applied Precision DeltaVision-OMX Super-Resolution Microscope (GE Life Sciences).

When dose-response curves were analyzed in GraphPad Prism for Bliss independence testing, the response from tandem peptide mediated killing exceeded the expected additive response of the two single peptide domains, indicating that there was synergy between the two peptide domains in the tandem peptide construct.

Example 2: Antimicrobial Constructs Formulated in Biodegradable Porous Silicon Nanoparticles Maintain Anti-Infective Properties To minimize toxicity, the best performing peptide (LACT-dKK) was formulated into nanoparticles to influence peptide biodistribution by increasing local drug concentrations and mitigating off-target toxicity profiles. As a strategy to improve biodistribution and mitigate toxicity, peptides were loaded in a biodegradable porous silicon nanoparticle (pSiNP).

pSiNPs were prepared as described previously (Joo, et al. *Advanced Functional Materials*. 2014, 24, 5688). Briefly, highly boron-doped p$^{++}$-type crystalline silicon wafers, polished on the (100) face, were electrochemically etched in an electrolyte consisting of 3:1 (v:v) 48% aqueous HF:ethanol under current control. The etching waveform consisted of a current density-time profile consisting of two current levels (50 mA/cm$^2$ for 1.8 sec; 400 mA/cm$^2$ for 0.36 sec), repeated for 150 cycles The resulting film was removed from the silicon substrate by application of a current density pulse of 3.7 mA/cm$^2$ for 250 sec in 1:29 (v:v) 48% aqueous HF:ethanol and fragmented by ultrasonication overnight. The resulting pSiNPs were dispersed in an aqueous solution of sodium tetraborate to grow a thin layer of silicon oxide on the particle surface.

Figure 4:
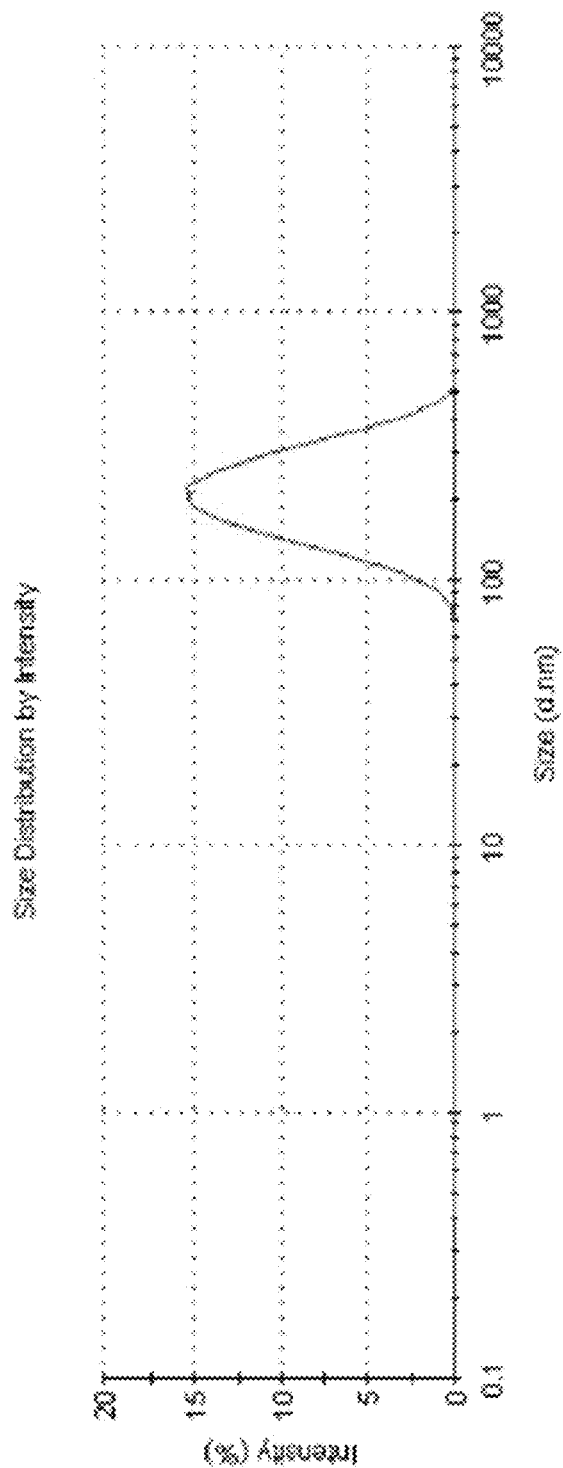
FIG. 4 is a graph of the representative size distribution (hydrodynamic diameter) of porous silicon nanoparticles used in the studies, measured by dynamic light scattering.

The resulting nanoparticles had a hydrodynamic diameter of 225±10 nm as measured by dynamic light scattering (n=6, representative plot in FIG. 4). These particles were of 50% porosity and contained pores of average diameter ~10 nm, sufficient to accommodate the ~6,400 molecular weight peptide. In order to optimize the nanoparticle formulation for loading capacity, a set of different chemical functionalizations was investigated to mediate physical interactions with the peptide cargo. The surface of pSiNPs was modified with phosphonates, carboxylates, sulfonates, and amines via silane chemistry and subsequent loading of peptide was achieved by infiltration (FIG. 5A). Amine groups were introduced by stirring the pSiNPs overnight in an ethanol solution 12 mM in 3-aminopropyl-dimethyl-ethoxy silane (APDMES) containing a catalytic amount of triethyl amine (TEA). Carboxylate modification was achieved by overnight reaction of the above amine-modified pSiNPs (3 mg) with succinic anhydride (10 mg) in 3 mL of DMF. Phosphonate modification was achieved by reacting pSiNPs in ethanol with 11.2 mM tetraethyl orthosilicate (TEOS) and a catalytic amount of TEA at room temperature for 1 hour. Subsequently, 3-(trihydroxysilyl)propyl methylphosphonate was added to a final concentration of 26.3 mM and further reacted overnight. Sulfonate modification was carried out following the same procedure as for the phosphonate modification but using 3-(trihydroxysilyl)-1-propane sulfonic acid as the silanating reagent.

Peptide was loaded into phosphonate-modified pSiNPs by incubating 33% (w:w) peptide:pSiNP for 2 hours at room temperature in water. Peptide-pSiNPs were purified by 3 rounds of centrifugation and resuspension in deionized water. Of the surface chemistries investigated, phosphonate modification yielded a high (~30%) weight loading of peptide by final mass (FIG. 5B), comparable to other charge-based assemblies of pSiNPs. Phosphonate modified pSiNPs also displayed high loading efficiency (80±9%, n=5), likely due to strong electrostatic interactions between the negatively-charged phosphonate-modified pores of pSiNP and positively-charged peptide cargo (FIG. 5C). Comparing transmission electron microscopy images of unloaded pSiNPs and peptide-loaded pSiNPs showed that the porous structure was maintained in each case (FIG. 5D). Transmission Electron Microscope (TEM) images were acquired with a JEOL-1200 EX II instrument. Zeta potential measurements of oxidized pSiNPs, phosphonate-modified pSiNPs, and peptide-loaded pSiNPs measured by DLS (Zetasizer ZS90, Malvern Instruments) revealed a negative surface potential for all of the particle types (FIG. 5E). Size measurements were carried out with particles dispersed in water, whereas the zeta potential analysis was performed in phosphate buffered saline (PBS), pH=7.4. Although all particle types displayed a net negative surface charge, the phosphonate modification showed values of zeta potential that were more negative than the oxidized pSiNPs, whereas the peptide-loaded pSiNPs showed a less negative zeta potential than the oxidized pSiNPs. The negative zeta potential for peptide-loaded pSiNPs indicates that the surface negative charge was not completely neutralized by surface-bound peptide (since the peptide itself carries a positive charge), and that at least a portion of the peptides had loaded into the pores.

Figure 5F:
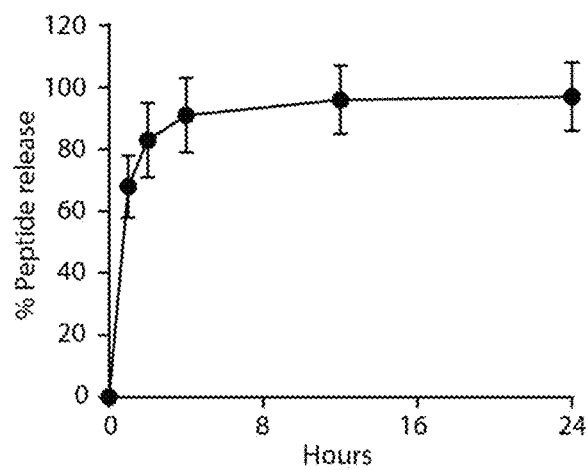
FIG. 5F shows the release of peptides (LACT-dKK) from phosphonate modified pSiNPs into phosphate buffered saline (PBS) by measuring fluorescence signal of peptide in the supernatant.

The release of peptide from phosphonate modified pSiNPs was monitored by incubation in phosphate buffered saline (PBS) and measuring fluorescently labeled peptide in the supernatant after centrifugation of intact pSiNPs (FIG. 5F). Peptide-loaded pSiNPs (0.3 mg, n=3) were dispersed in 1 mL of PBS, pH 7.4 at room temperature with mild shaking. The supernatant containing released fluorescein-labeled peptides was collected at different incubation time points (1 h, 2 h, 4 h, 12 h, 24 h, 48 h) and analyzed by optical absorbance spectroscopy ($\lambda$=495 nm). Concentrations of the released peptides were determined using a calibration curve obtained with standard solutions of the same peptide in PBS.

Figure 5G:
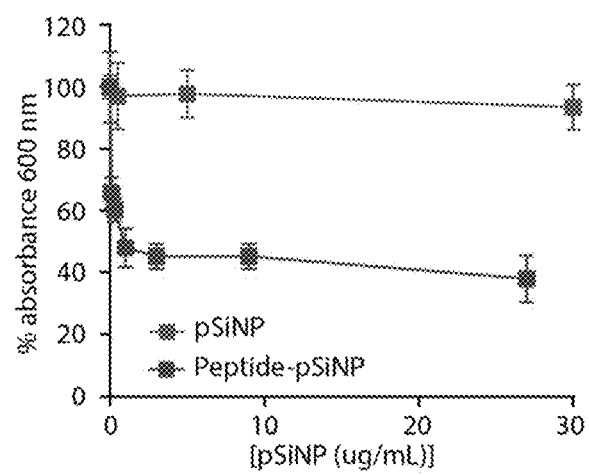
FIG. 5G shows that peptides (LACT-dKK) formulated into phosphonate modified pSiNPs were able to mediate killing of *P. aeruginosa*.
Figure 6A:
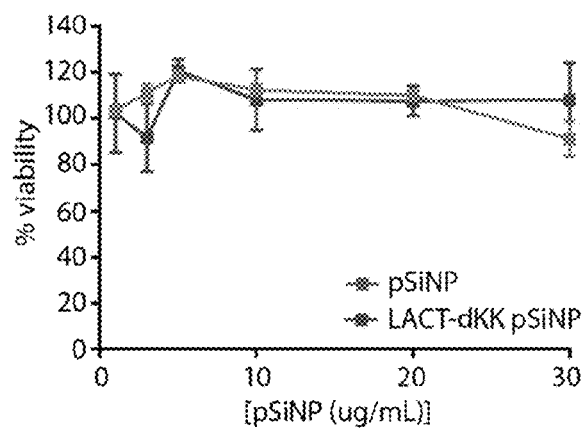
FIGS. 6A and 6B are line graphs showing that LACT-dKK peptides formulated into pSiNP show minimal toxicity to NIH 3T3 mammalian cells and little propensity to lyse red blood cells, respectively.
Figure 6B:
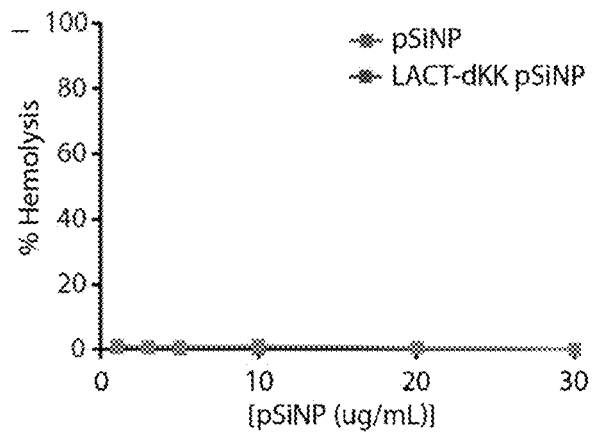

Peptides formulated into phosphonate modified pSiNP were able to mediate killing of *P. aeruginosa* (FIG. 5G) while showing minimal toxicity to mammalian cells (FIG. 6A) and minimal red blood cell lysis (FIG. 6B). For each experiment, *P. aeruginosa* strain PA01 was started from a frozen glycerol stock and cultured overnight. A 1:100 dilution from the overnight culture was grown at 37° C. with shaking to an OD$_{600}$ between 0.2-0.6. The number of colony forming units (CFU) per mL was determined by titering cultures with known absorbance values.

For growth assays, PA01 were diluted in LB media to a final concentration of 2×10$^6$ CFU/ml. For screening, peptides were tested in triplicates of a series of 8 2-fold dilutions starting from 5 uM. After 16 hours of incubation, bacterial turbidity was examined or the absorbance at 600 nm was measured to determine the minimal inhibitory concentration (MIC).

To perform hemolysis assays, red blood cells were collected from mouse blood harvested in 5 mM EDTA and stored on ice. Red blood cells were washed in 150 mM NaCl and harvested by centrifugation. Red blood cells and peptide were incubated together for 1 hour at 37° C. For screening, peptides were tested in triplicates of a series of 8 2-fold dilutions starting from 5 uM. Unlysed red blood cells were removed by centrifugation, and released hemoglobin was quantified by measuring absorbance at 541 nm. Percent hemolysis was determined by normalizing to red blood cells incubated with 0.1% Triton-X 100.

Mammalian cell toxicity assay were performed using NIH 3T3 or Neuro-2a cells plated at 2,000 cells per well in at 96-well plate 24 hours before treatment with peptides at the indicated concentrations for 4 hours. Cell viability was measured with the Aqueous One Cell Proliferation Assay (Promega) 72 hours after treatment. For screening, peptides were tested in triplicates of a series of 8 2-fold dilutions starting from 5 uM. Formulations of pSiNP were tested at 24 hours after treatment in NIH-3T3 cells.

Example 3: pSiNP Formulation of Antimicrobial Constructs Improves Toxicity Profile and Reduces *P. aeruginosa* Lung Infection in an Animal Model To examine the utility of this peptide-pSiNP platform in vivo, LACT-dKK formulated into pSiNPs were delivered in the context of a P. aeruginosa lung infections. First the histological response of the nanomaterials after direct administration to the lungs of healthy mice was tested. Sample solutions (PBS, unloaded pSiNPs, free peptide, or peptide-pSiNP) were instilled into the lung via a catheter inserted into the trachea. 6-8 week old CD-1 mice were obtained from Charles River. Neutropenia was introduced by injecting cyclophosphamide at 150 mg/kg four days and 100 mg/kg one day pre-infection. For co-treatment, mice were anesthetized by isoflurane and infected with $2\times10^5$ CFU in 50 µL by tracheal instillation via a 22 G catheter (EXCEL International). Mice received two doses of 1.5 nmole peptide in free form or peptide-pSiNP (~30 µg of pSiNP) in 50 µL of PBS via tracheal instillation during initial infection and 2 hours post-infection. Mice were monitored for 24 hours post-infection and lung tissue was collected for homogenization when mice reached euthanasia criteria or at 24 hours. For post-treatment, mice received $1e10^3$ CFU and were treated with four doses of 2 nmole peptide by tracheal instillation. CFUs of PA01 per lung were calculated by plating dilutions of lung homogenates on agar plates and counting colonies. All therapeutic studies were repeated in at least two independent trials.

Mice that received free peptide displayed slowed, labored breathing compared to PBS treated mice between 4-8 hours after dosing, whereas no change what observed when mice were administered peptide-pSiNPs. To correlate these observations with any changes in tissue pathology and circulating cytokine levels, organs and blood were harvested at 4 or 24 hours after dosing. Hematoxylin and eosin staining of lung sections were assessed by a pathologist blinded to treatment conditions. Lung sections were blocked in 2% bovine serum albumin, 5% goat serum in PBS and stained for antibodies against *pseudomonas* (Abcam, 1:500). Appropriately labeled secondary antibodies were used to detect primary antibodies. Lung scans were acquired on a Perkin Elmer Pannoramic250 and high magnification images were taken on a Nikon Ti Eclipse microscope.

Figure 6C:
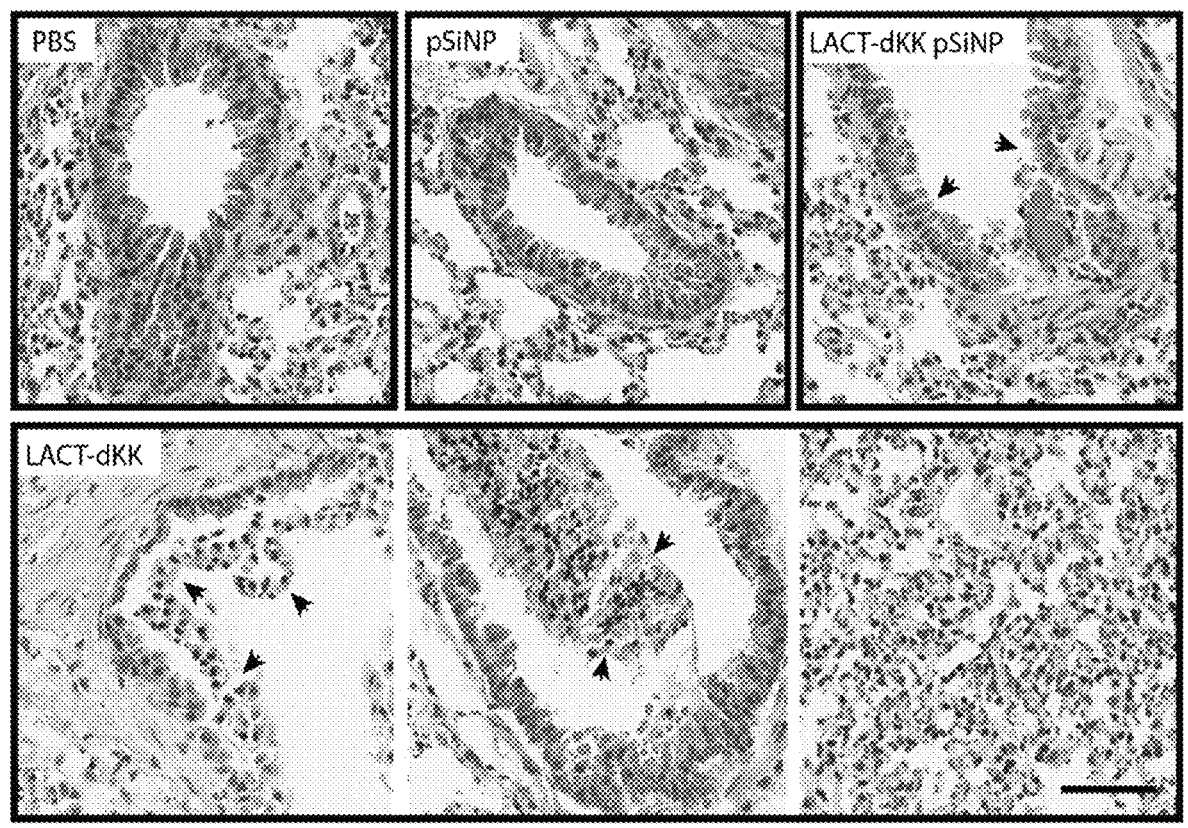
FIG. 6C provides representative images of H&E staining of lung sections from mice treated with PBS, pSiNP, LACT-dKK formulated into pSiNP, or LACT-dKK peptide administered directly to the lungs. Arrowheads indicate signs of mild lung epithelial damage (LACT-dKK pSiNP), epithelial sloughing and bronchitis (free LACT-dKK; bottom, left to right). Free LACT-dKK treated mice also had signs of interstitial pneumonitis (bottom, far right panel). Scale bar represents 50 μm.
Figure 7:
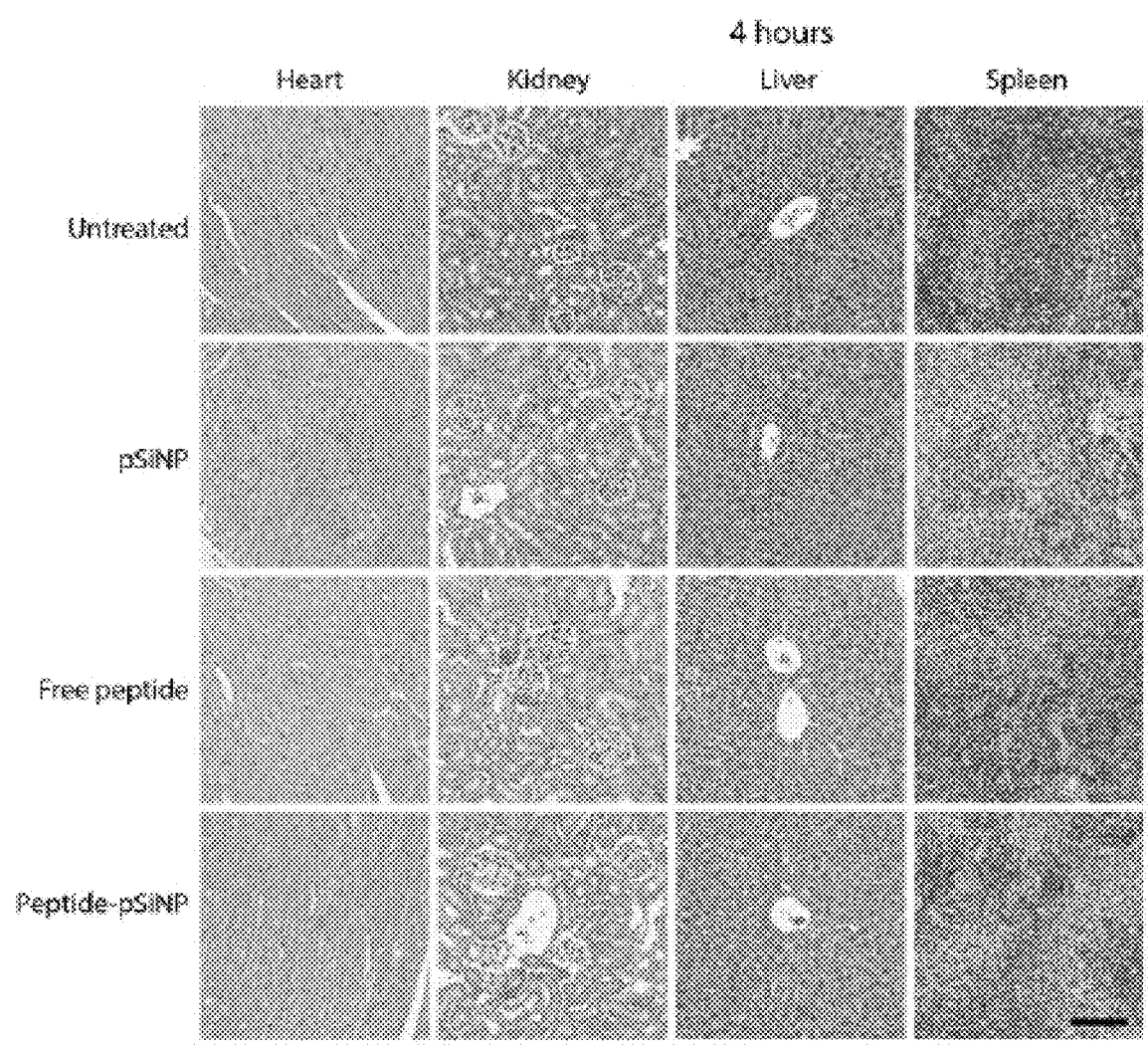
FIG. 7 provides representative images of H&E staining of specified organs at 4 hours (top) and 24 hours (bottom) after administration of indicated treatments. Peptide=LACT-dKK. Scale bar represents 100 μm.
Figure 7:
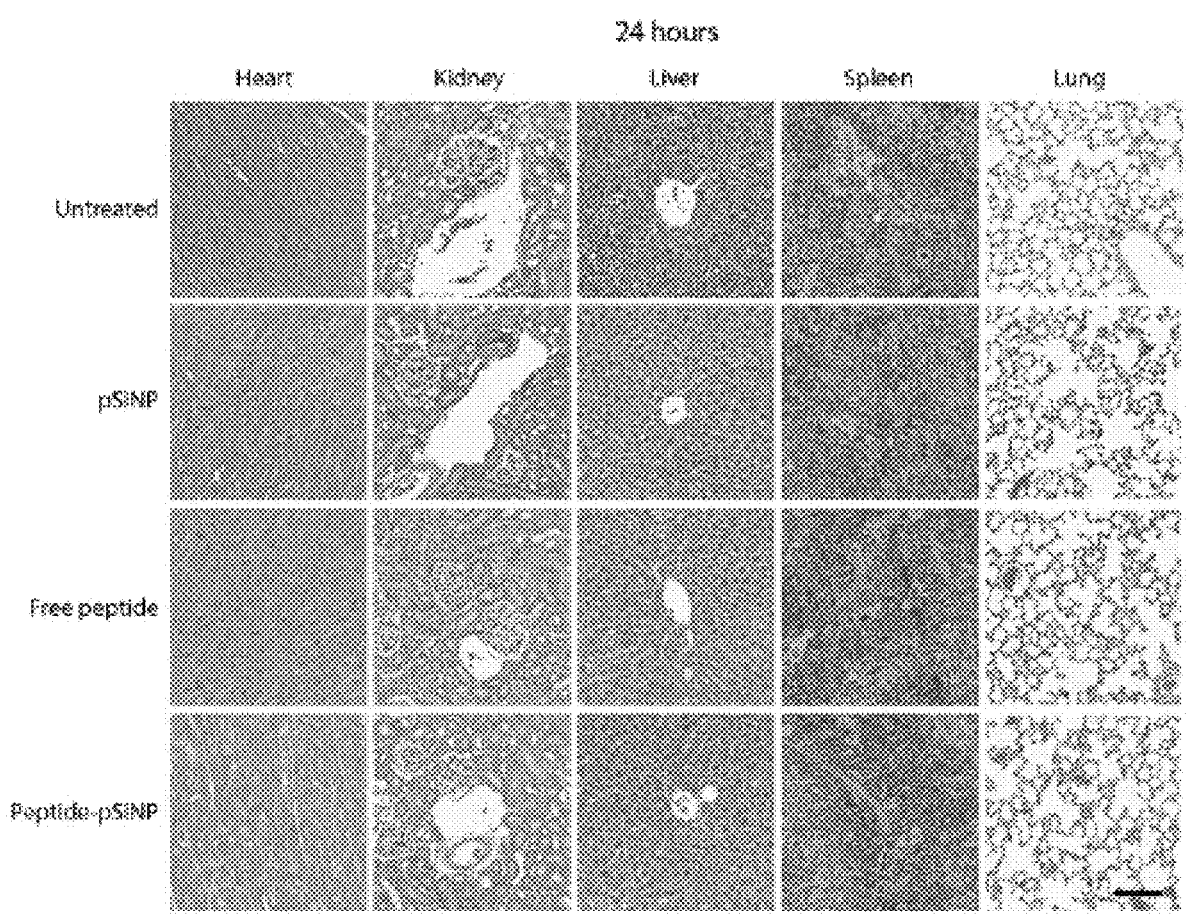
Figure 8A:
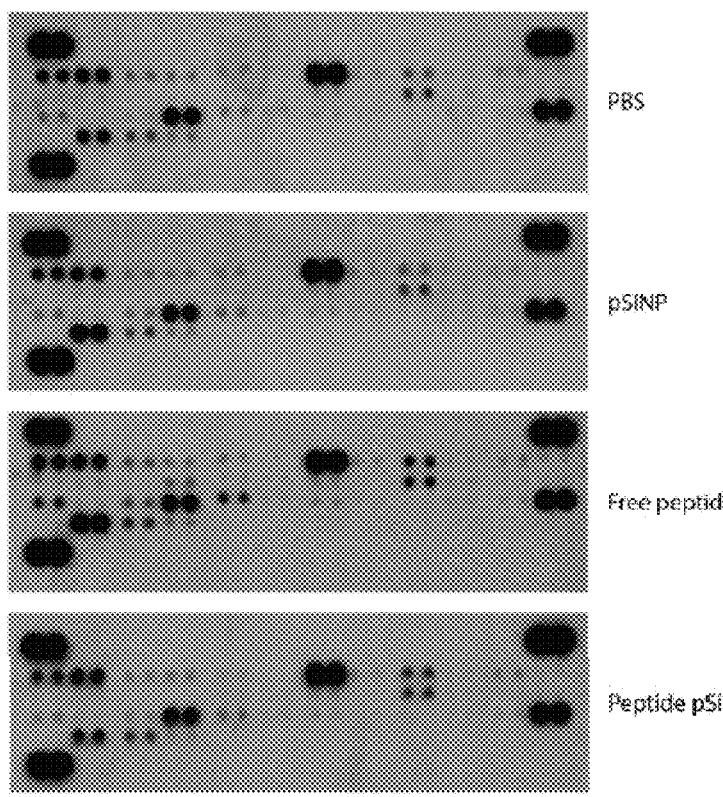
FIG. 8A shows blots of serum collected from mice 4 hours after lung delivery of pSiNP, free peptide, or peptide-pSiNP was applied to a mouse cytokine array. Peptide=LACT-dKK.
Figure 8B:
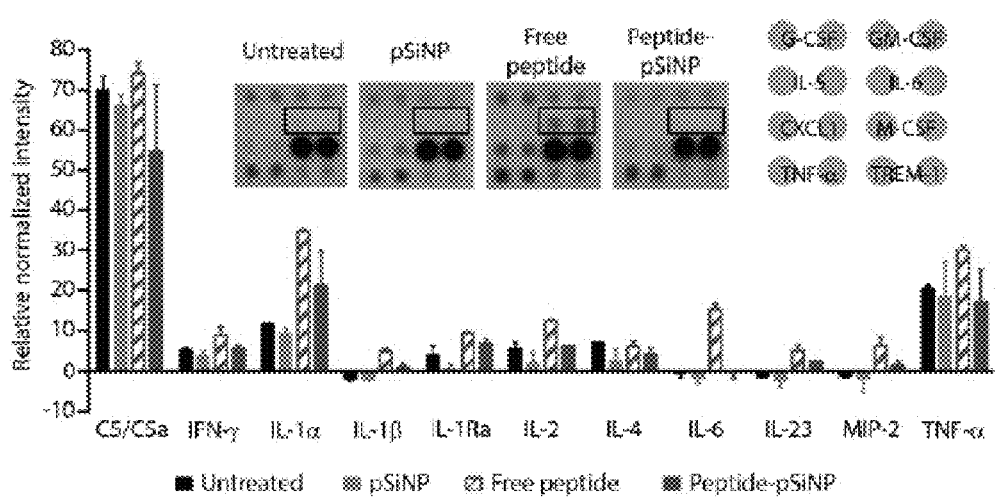
FIG. 8B shows the serum cytokine profile for mice treated with pSiNP, LACT-dKK formulated in pSiNP (peptide-pSiNP), or LACT-dKK peptide (free peptide), compared to untreated mice. Inset shows a portion of representative blots, with a box around IL-6.

Lungs from untreated mice and mice administered either peptide-loaded or empty pSiNP displayed generally normal morphology, and peptide-pSiNP administered mice presented with mild bronchial epithelial damage (FIG. 6C; top row). By contrast, evidence of damage in the lungs at 4 hours after administration of free peptide was substantial as assessed by a pathologist: sloughing of the bronchial epithelium, bronchitis, and interstitial pneumonitis were all observed (FIG. 6C; bottom row). However, evidence of toxicity appeared to subside by 24 hours and were not present in any other organs (FIG. 7), indicating a local and transient response. To investigate the molecular pathways involved at the time point during which histological changes were observed, serum collected from mice at 4 hours was assayed for the presence of a panel of cytokines and revealed upregulation of cytokines documented as part of the acute response to antimicrobial peptides (FIGS. 8A and 8B). In particular, an increase in cytokine IL-6 in mice administered free peptide compared to the other treatment groups was observed (FIG. 8B). These results were consistent with the histopathological analysis. Together, the mouse behavior, histopathology, and cytokine data present a strong motivation to package toxic peptide antibacterial agents during administration, and underscore the advantages of a suitable biodegradable carrier for lung delivery. Based on these toxicity studies, free peptide was deemed unacceptable to be dosed in animals without adverse effects. Therefore the subsequent functional studies were performed using only peptide-loaded pSiNPs.

In order to assess the therapeutic impact of peptide-pSiNP administration, the peptide nanomaterial was applied to a mouse model of P. aeruginosa lung infection. PA01 was instilled into the lungs via a catheter and infection levels were determined by titering the number of CFU harvested from lung tissue. First, the localization of peptide-pSiNP in the context of P. aeruginosa pneumonia was characterized. The distribution of fluorescently labeled peptide payload delivered 2 and 4 hours after the mice were inoculated with bacteria via lung instillation was examined.

For toxicity studies, organs were collected 4 or 24 hours after the first dose of treatment and organs were drop-fixed in 10% formalin. Organs were embedded in paraffin, cut into 6 µm sections, and stained with hematoxylin & eosin using standard protocols. Signs of tissue damage were assessed by a pathologist blinded to treatment conditions. For cytokine analysis, blood was collected 4 hours after first dose of treatment in 5 mM EDTA-PBS and red blood cells were cleared by centrifugation. Serum was stored at −80° C. until analysis. Serum was analyzed by Mouse Cytokine Antibody Array, Panel A (R&D Biosystems). Full map of cytokines can be found on the product data sheet. Two mice were used for each time point and condition. Representative images and blots were used for figures.

Organs were retrieved and assessed for payload fluorescence 4 hours after the last administration. Signal was detected in the lungs, whereas no detectable off-target organ accumulation was observed, as expected from a direct lung administration route (FIG. 9A; FIG. 10A).

To study the bulk biodistribution of particles in the lung and how they interact with cell types in the lung, particles (1.5 nmole peptide dose) were delivered 2 and 4 hours post infection ($2\times10^5$ CFU/mouse) and organs were retrieved 8 hours after infection. After IVIS imaging of organs, lungs were drop-fixed in 10% formalin overnight, washed with PBS and embedded in paraffin for sectioning.

Staining and imaging of cross-sections through the lung reveal widespread distribution of both peptide and P. aeruginosa throughout the lung, and a representative image is shown in FIG. 9B. Cellular-level examination of untreated and peptide-pSiNP treated lungs reveal some evidence of payload internalization into $F4/80^+$ resident interstitial and alveolar macrophages, but not into infiltrating $CD11b^+$ monocytes recruited to the infected areas (FIG. 10B).

Improvement of survival and bacterial titers after peptide-pSiNP administration were tested in the P. aeruginosa lung infection model. At $2\times10^5$ CFU/mouse, development of lung infection with P. aeruginosa is aggressive, with only 10-20% 24-hour survival without therapeutic intervention. First the potential therapeutic efficacy of peptide-pSiNP materials when co-administered with the bacteria at high titer inoculums was tested. Mice were given two doses of peptide-pSiNP at 30 µg of pSiNP and 1.5 nmoles peptide, or the equivalent amount of empty pSiNP carrier. The mice were observed and their lungs harvested at the survival endpoint, or at 24 hours. The peptide-pSiNP formulations greatly improved the survival to 24 hours. A lower than 20% survival observed with vehicle treatment improved to 100% survival when either of the peptide-pSiNP formulations was administered (FIG. 9C). Empty pSiNPs appeared to cause a slight improvement in survival, but the difference to control treatment was not statistically significant. To confirm that the improvement in survival was due to decreased lung titers of P. aeruginosa, lungs were excised and the number of CFU in the organ titered. A dramatic decrease in bacteria was observed, with lung titers 4-6 $\log_{10}$ lower than when no therapeutic intervention was administered (FIG. 9D).

Figure 9E:
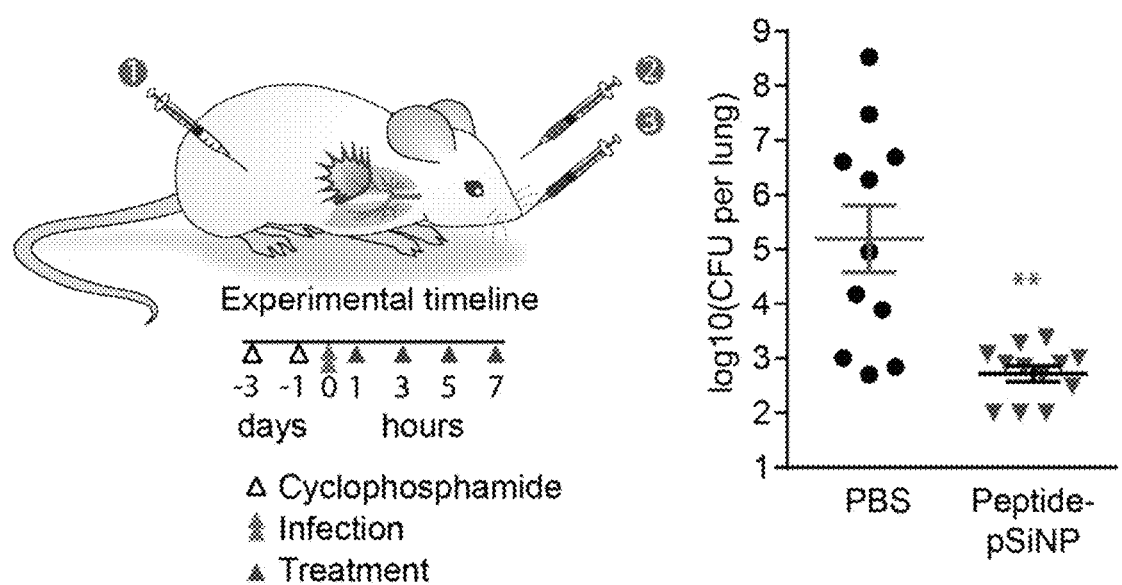
FIG. 9E is a schematic of the experimental design modified for physiological infection timescales of infection with *P. aeruginosa* to allow for intervention with 100% survival at 24 hours. The graph shows bacterial CFU titered from lungs of mice 24 hours post treatment with LACT-dKK formulated into pSiNP (peptide-pSiNP), compared to PBS control.

Based on these encouraging findings, it was determined whether the construct could perform as a more clinically relevant anti-infective, by administering peptide-pSiNP material 1 hour after bacterial instillation. Mice were infected with 1×10$^3$ CFU *P. aeruginosa*/mouse to establish an infection that resulted in near 100% 24-hour survival to create a timeframe that allows for intervention. The mice were treated at 1, 3, 5, and 7 hours after infection with 2 nmoles of peptide/40 μg of pSiNP per dose. The lungs were harvested at 24 hours and titered for bacteria. Untreated mice had titers that ranged from log$_{10}$ 2-9 with an average log$_{10}$ value of 5.2 CFU/lung, whereas mice treated with peptide-pSiNP had an average log$_{10}$ value of 2.7 CFU/lung (FIG. 9E). Total dosage of anti-infective peptide was 0.7 mg/kg per mouse for co-treatment and 1.9 mg/kg for post-treatment, on par with the 1.5-2.5 mg/kg dosing used clinically for colistin. Colistin, a peptide-based antibacterial considered a drug of last resort due to its toxicity profile, has limited efficacy in the context of pneumonia, supporting the benefit of developing additional agents to combat infections.

Figure 13A:
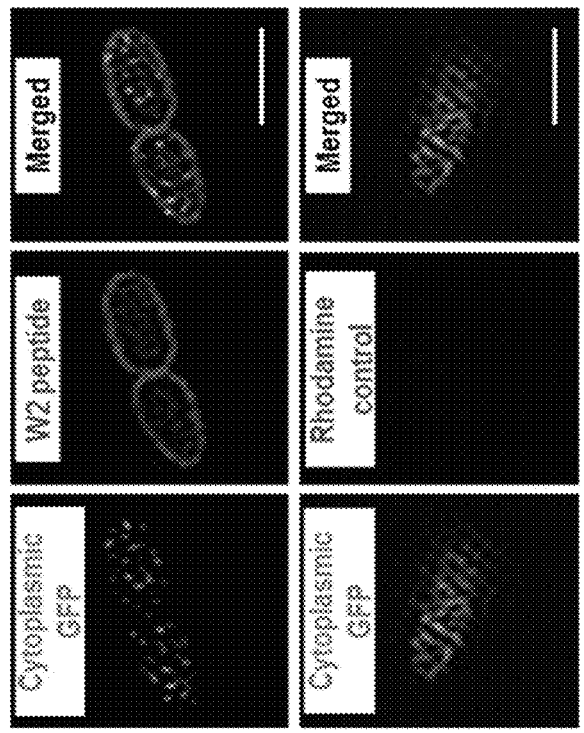
FIG. 13A shows growth inhibition of *P. aeruginosa* after incubation with W2 peptide, a mixture of W2 peptide and free linezolid (LZD), and W2-LZD conjugate. W2=WLBU2
Figure 13B:
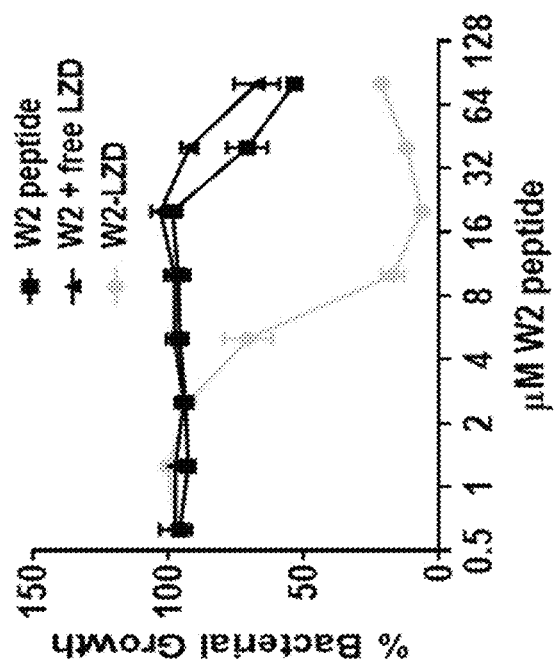
FIG. 13B shows super-resolution microscopy images of *P. aeruginosa* after incubation with rhodamine-labeled W2 peptide (top row) and rhodamine alone (bottom row). W2=WLBU2
Figure 13D:
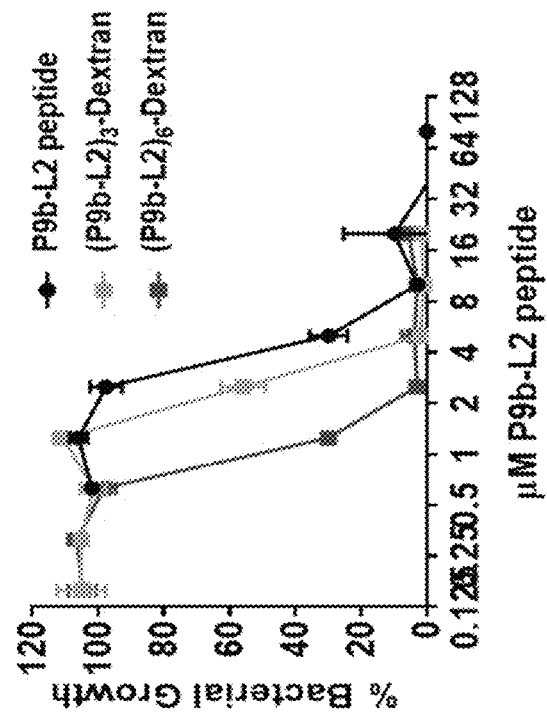
FIG. 13D is a line graph showing growth inhibition of *P. aeruginosa* treated with P9b-L2-grafted dextrans. LBU2=L2.
Figure 13C:
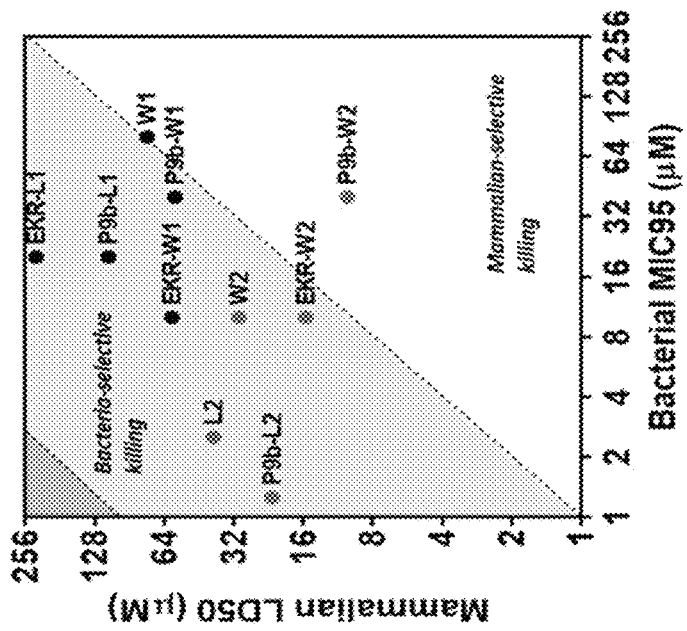
FIG. 13C is a dot plot showing cytotoxic concentrations of peptide-LZD conjugates in mammalian cells versus *P. aeruginosa*. Bacteria-selective killing conjugates lie in the orange region of the plot. Conjugates with better activity than their respective peptides alone are denoted by green dots.

Lastly, to determine whether the tandem peptide anti-infective was extensible to other strains of *P. aeruginosa* beyond the lab strain PA01, peptide in clinical isolates taken from human patient lungs were tested (Table 2). Of the five clinical isolates tested, three of the strains were resistant to first-line antibiotics as reported previously. All strains that were evaluated were susceptible to tandem peptide mediated killing, and displayed MIC values between 2- to 4-fold to that of the PA01 MIC.

terial growth compared to WLBU2 alone or WLBU2 with free linezolid (FIG. 13A). Super-resolution microscopy shows that this peptide is able to associate with the membrane and localize to the cytosol of *P. aeruginosa* (FIG. 13B). WLBU2 is part of a family of helical cationic peptides that were designed to specifically kill *P. aeruginosa*. Other members of this peptide family, WLBU1 and LBU2, were synthesized in tandem with *P. aeruginosa* targeting peptides (P9b and EKR) and conjugated to linezolid. These peptide-drug conjugates were evaluated for their ability to inhibit *P. aeruginosa* and cross validated for mammalian cell toxicity. FIG. 13C shows the cytotoxic concentrations of the peptide-drug conjugates.

WLBU2, LBU2, and LBU2-P9b peptides were grafted onto high molecular weight dextrans (40 kDa) to generate long-circulating bacteria-penetrating nanoplatforms. Amine-modified dextran-40 was synthesized by oxidation of dextran-40 using sodium periodate and subsequent amination in a reaction with ethylene diamine and cyanoborohydride. The product was purified using gel filtration and dialysis and lyophilized. Cysteine-terminated W2 peptides were attached to amine-modified dextran-40 at a molar feed ratio of 5-20 peptides per dextran via an SIA linker.

Figure 13E:
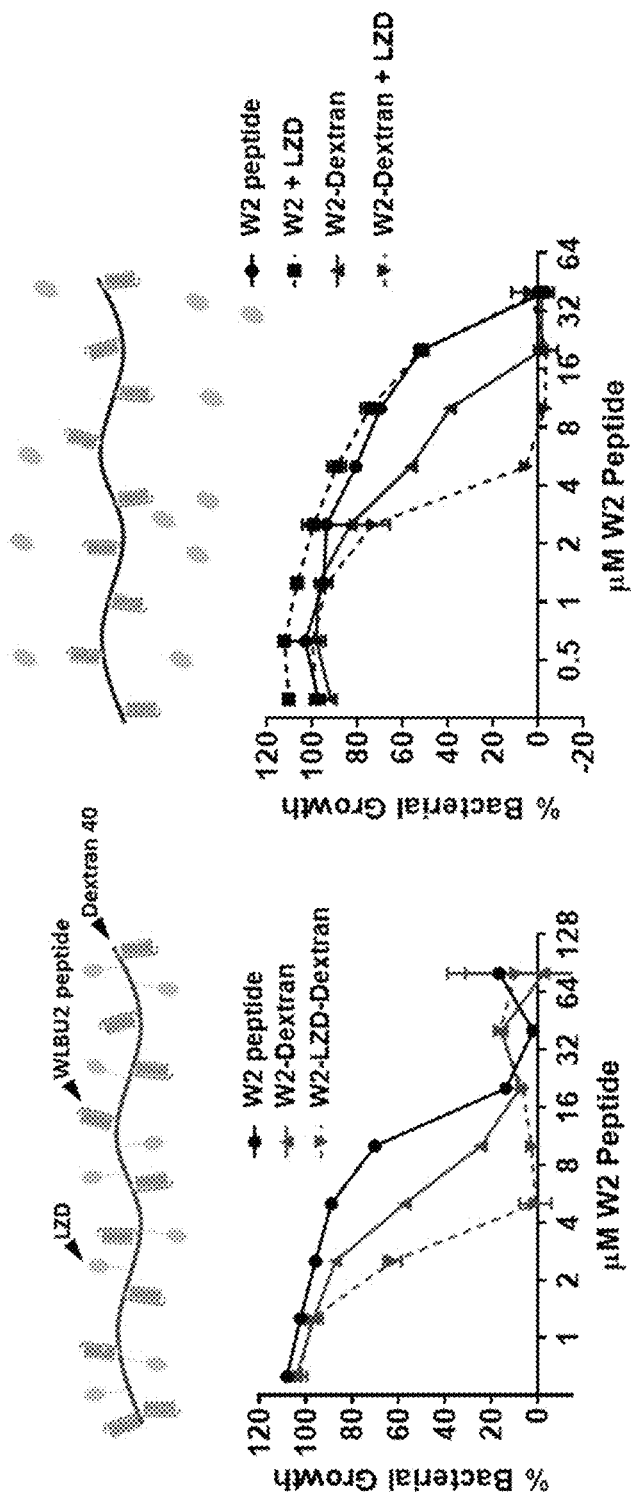
FIG. 13E shows growth inhibition of *P. aeruginosa* treated with W2-grafted dextrans and W2- and LZD-grafted dextrans (left) versus *P. aeruginosa* treated with a mixture of W2-grafted dextrans and free LZD (right). Schematics of the constructs are shown in the top. W2=WLBU2

Attachment of multiple P9b-LBU2 tandem peptides to dextran showed increased antibacterial activity (FIG. 13D), indicating that multivalency can be harnessed to increase peptide activity. The same multivalent effects were observed in WLBU2-grafted dextrans (FIG. 13E). Tethering of linezolid to WLBU2-dextran further increases antibacterial

TABLE 2

| Strain | Ciprofloxacin | Imipenem | Ceftazidime | Piperacillin | Levofloxacin | Peptide (MIC) |
|---|---|---|---|---|---|---|
| PAO1 | S | S | S | S | S | S |
| Clinical Isolate 1 | R | R | R | R | R | S |
| Clinical Isolate 2 | S | R | S | S | S | S |
| Clinical Isolate 3 | S | S | S | S | S | S |
| Clinical Isolate 4 | S | R | S | S | S | S |
| Clinical Isolate 5 | S | S | S | S | S | S |

Example 4: Antimicrobial Constructs Effectively Deliver Small Molecules into *P. aeruginosa*

Figure 11A:
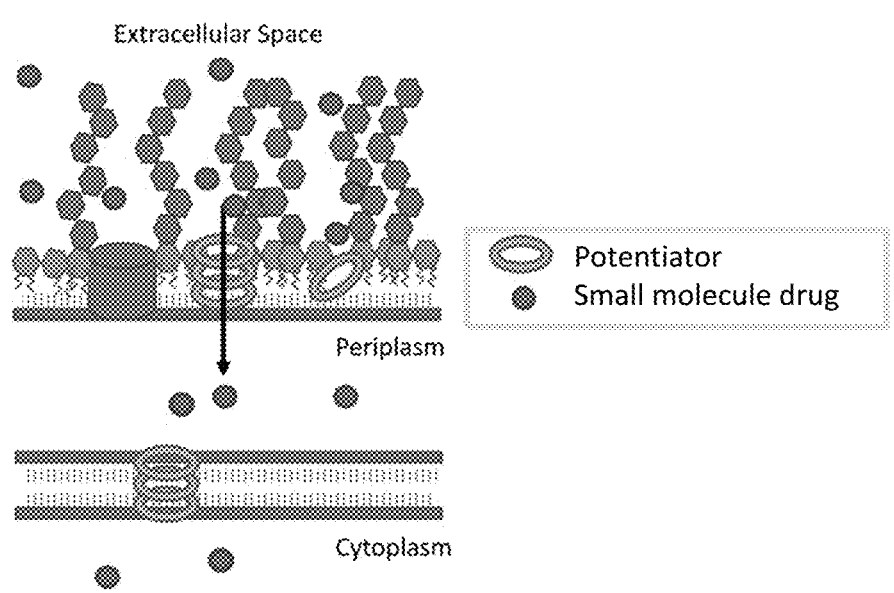
FIG. 11A is a schematic showing the mechanism of a potentiator-drug pair
Figure 11B:
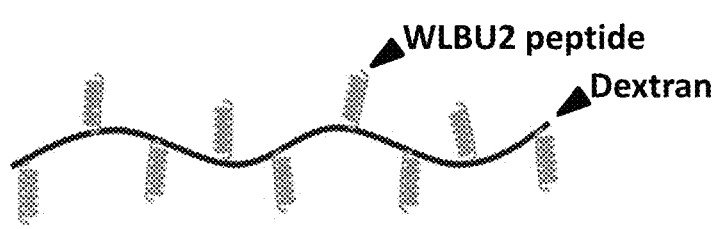
FIG. 11B is a schematic of WLBU2 peptides conjugated to a dextran molecule.

In another manifestation of the antimicrobial construct, a (1) membrane-penetrating domain and (2) a carrier were concatenated. The goal was for the delivery of small molecules which are normally unable to penetrate the double lipid membrane structure that surrounds gram negative bacteria (FIG. 11A). Such permeabilization agents or "potentiator agents" would be transformative and allow us to leverage prior investments in drug development. In the following work, a peptide-based agent that permeabilizes gram-negative membranes to increase influx of small molecules into the cytoplasm was developed. FIG. 11B shows an exemplary schematic of the construct.

Figure 12:
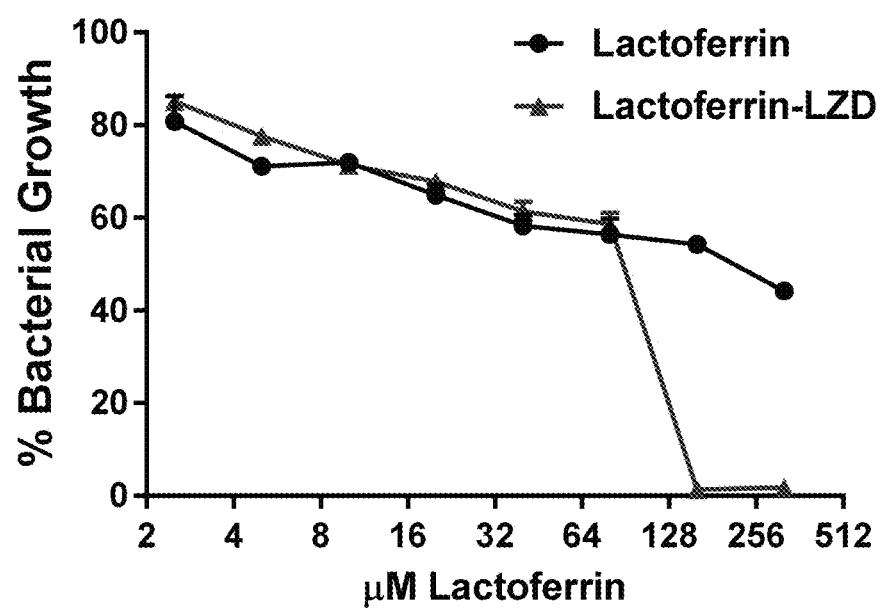
FIG. 12 is a line graph showing growth inhibition of *P. aeruginosa* when treated with linezolid chemically-conjugated to lactoferrin and lactoferrin peptide alone.

In order to identify peptides which would improve the penetration of small molecules into bacteria library of 30 peptide-linezolid conjugates was synthesized using antimicrobial peptides curated from literature. Linezolid is a small molecule that is normally unable to kill gram-negative bacteria due to its inability to cross the membrane. The peptide-linezolid library was screened in a growth inhibition assay in *P. aeruginosa*. Interestingly, lactoferrin conjugated to linezolid was found to prevent bacterial growth compared to free lactoferrin (FIG. 12). In addition, WLBU2 peptide ("W2") conjugated to linezolid was found to prevent bac-activity demonstrating that WLBU2-dextrans can be vehicles for small molecule drugs into *P. aeruginosa* (FIG. 13E, left). Furthermore, a subsequent growth inhibition assay demonstrated that multivalent WLBU2-dextrans can also facilitate activity of free linezolid into *P. aeruginosa*, offering a rapidly adaptable strategy to improve efficacy of small molecule drugs (FIG. 13E, right).

Figure 14A:
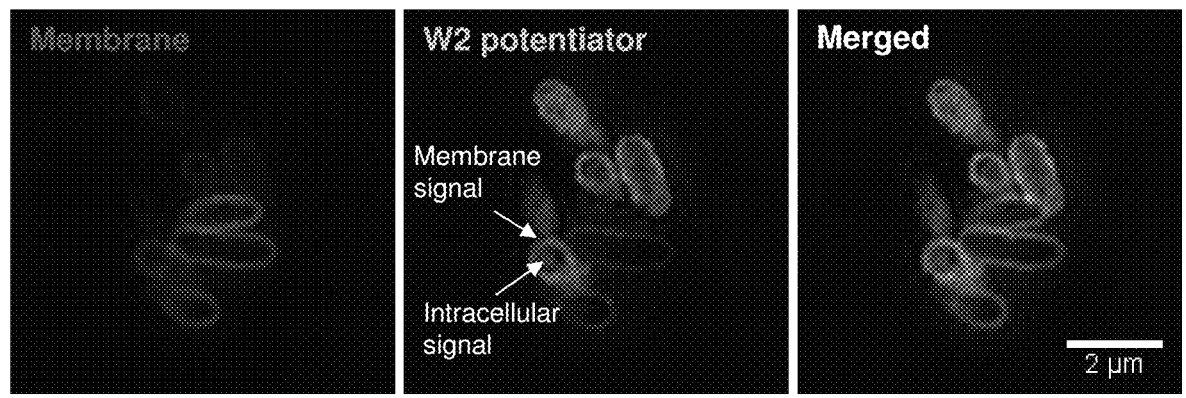
FIG. 14A provides representative images showing association of W2-grafted dextrans to the bacterial membrane and entry into the cytoplasm. W2=WLBU2
Figure 14B:
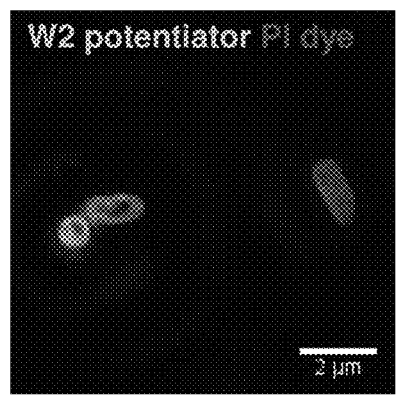
FIG. 14B provides a representative image showing permeabilization of the *P. aeruginosa* membrane by W2-grafted dextrans and entry of propidium iodide (PI) dye into the cytoplasm. W2=WLBU2

To visualize membrane permeabilization of WLBU2, *P. aeruginosa* was incubated with Alexa Fluor 488-labeld WLBU2 potentiator for 15 minutes and subsequently washed 2 times with phosphate buffer solution to remove unbound potentiator. Bacteria were then stained with a membrane dye. Using super-resolution microscopy, W2 potentiator signal was observed in the membrane as well as in the cytoplasm (FIG. 14A). To confirm potentiator-induced membrane permeabilization, bacteria were incubated with both fluorescent potentiator and a small molecule dye that does not penetrate the membrane of live cells, propidium iodide (PI). As observed in the prior experiment, there was potentiator signal in the bacterial membrane and strong, diffuse PI signal in the cytoplasm, confirming membrane permeabilization (FIG. 14B).

Figure 15A:
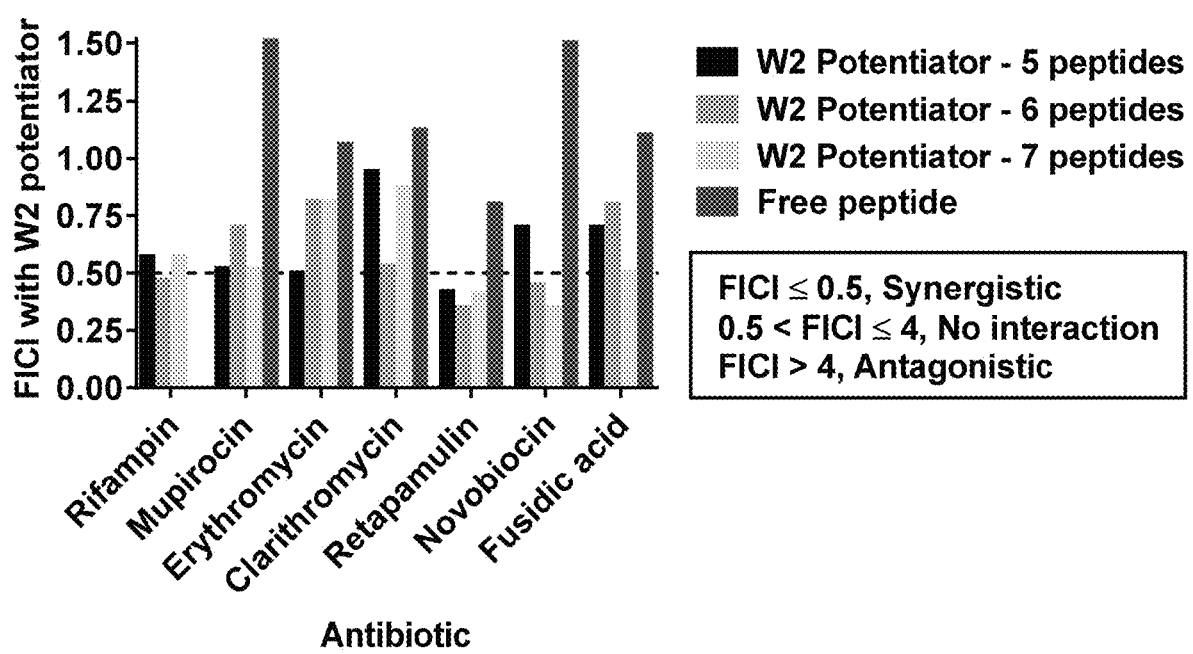
FIG. 15A provides a bar graph showing the fractional inhibitory concentration indices (FICI) of W2-grafted dextran with various antibiotics. W2=WLBU2
Figure 15B:
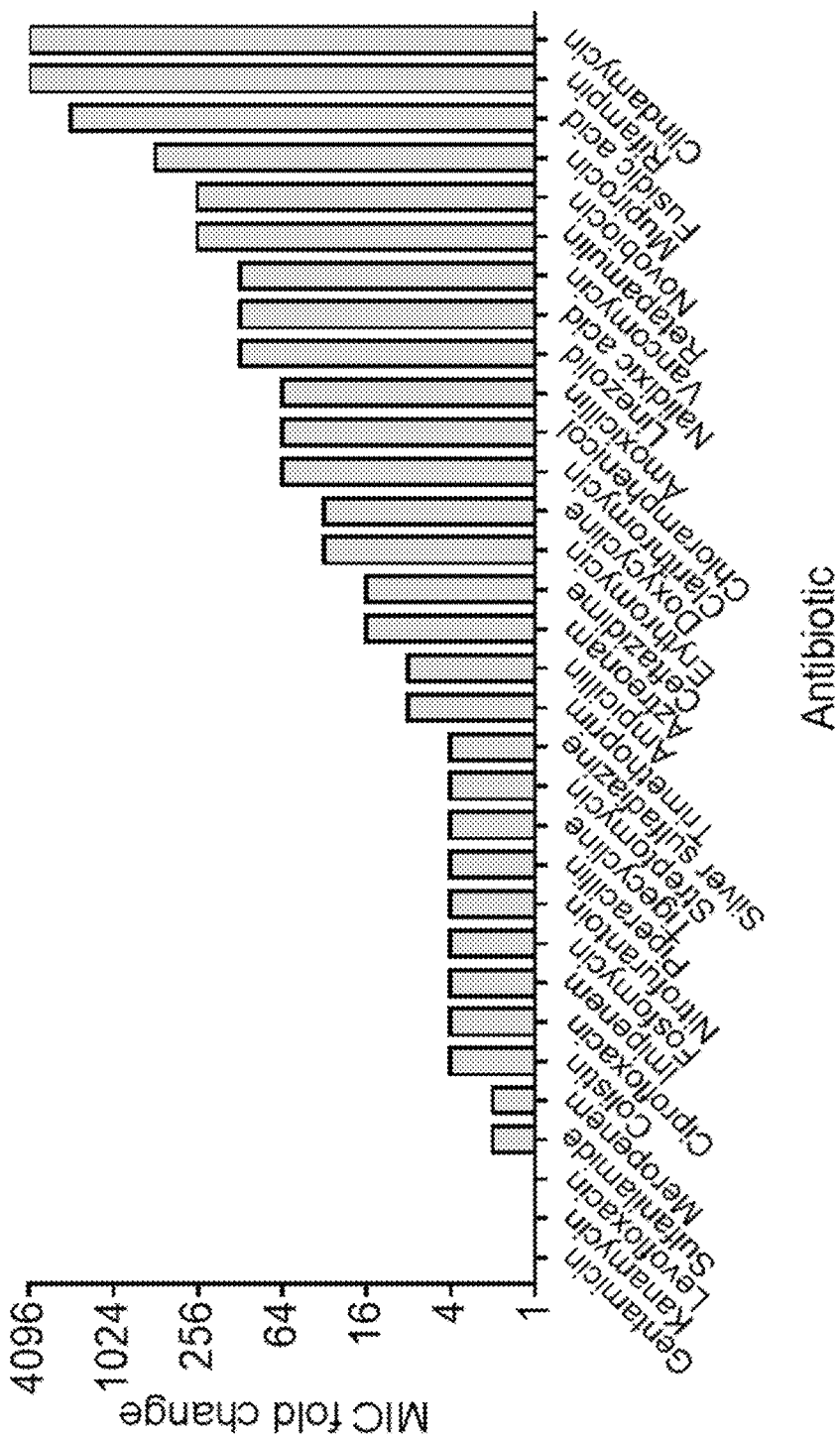
FIG. 15B provides a bar graph showing the fold reduction of minimal inhibitory concentrations (MIC) of small molecule antimicrobial drugs coupled with WLBU2-dextran in microdilution assays with *P. aeruginosa* (strain PA14).
Figures 15C, 15D:
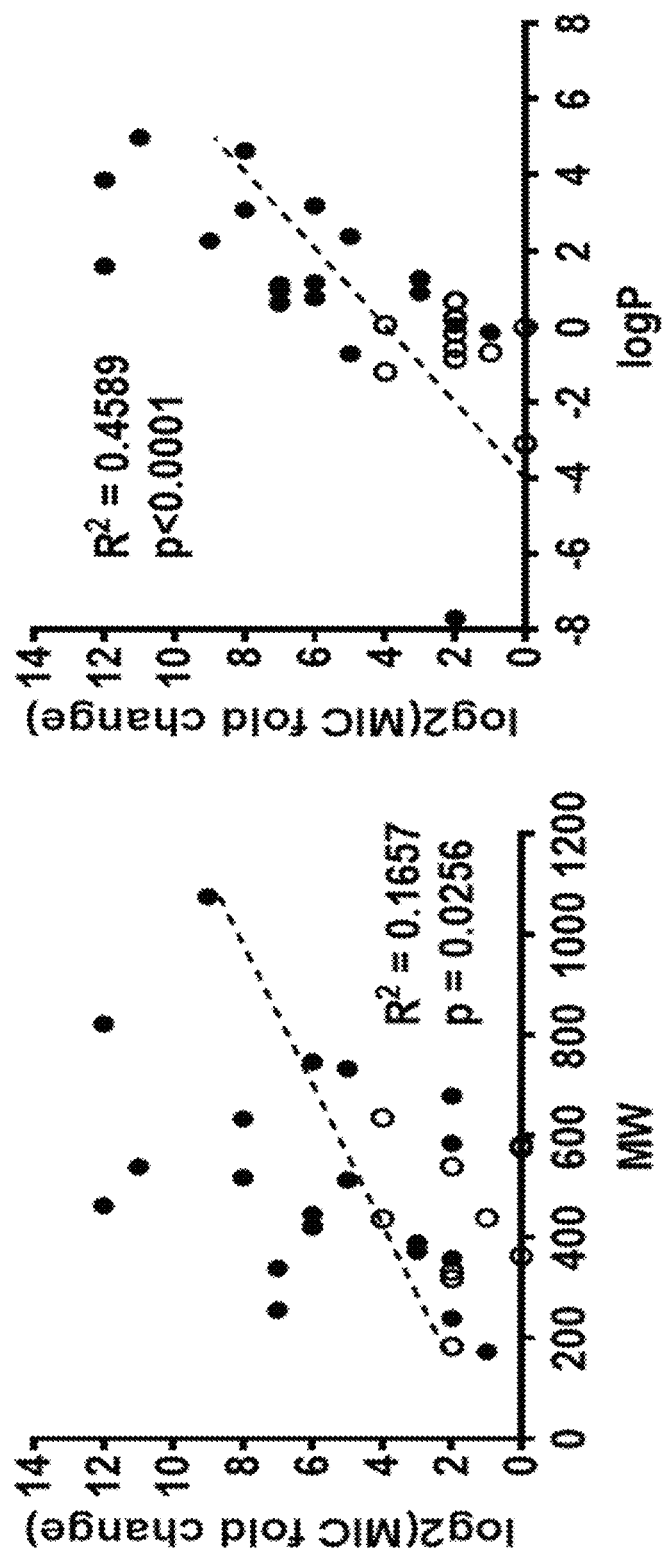
FIG. 15C is a graph showing positive correlation (p<0.05) between molecular weight of the drugs evaluated in FIG. 15B and increased activity when combined with WLBU2-dextran. Open circles indicate antibiotics that are known anti-pseudomonal drugs.
FIG. 15D is a graph showing positive correlation (p<0.0001) between log P values of drugs evaluated in FIG. 15B and increased activity when combined with WLBU2-dextran. Open circles indicate antibiotics that are known anti-pseudomonal drugs.

To assess drug potentiation of other small molecules, checkerboard assays were completed to identify drugs that had increased activity in the presence of WLBU2 potentiator. Fractional inhibitory concentration indices (FICIs) indicated synergy between WLBU2 potentiator and retapamulin as well as novobiocin (drugs from two different antibiotic classes) (FIG. 15A). FICIs are up to 3-fold lower for WLBU2 potentiator-drug pairs compared to free peptide-drug pairs indicating enhanced membrane permeabilization with the peptide in multivalent format versus monovalent. Furthermore, minimal inhibitory concentrations (MIC) were reduced by three orders of magnitude when drugs are paired with WLBU2 potentiators (FIG. 15B). Moreover, the MIC fold changed correlated significantly with the molecular weight of the drug (FIG. 15C) and lipophilicity (FIG. 15D). WLBU2-dextran had the greatest effect on large and lipophilic drugs (greater log P value), which are currently not used to treat *P. aeruginosa* infections.

Table 3 shows the MIC for linezolid and ciprofloxacin in wild-type *P. aeruginosa* strains PA14 and PA01, compared to a hyperpermeable strain Z61.

TABLE 3

| | MIC (μg/mL) | | |
| | *P. aeruginosa* strain | | |
| Compound | PA14 | PA01 | Z61 |
|---|---|---|---|
| Linezolid | >128 | >128 | 8 |
| Ciprofloxacin | 0.5 | 2 | <0.25 |

Together, these data provide evidence that antimicrobial constructs can be used in conjunction with small molecules in univalent or multivalent formats to improve anti-infective efficacy.

Sequence Summary

| SEQ ID NO | Description | Sequence |
|---|---|---|
| 1 | Lactoferrin-derived peptide | KCFQWQRNMRKVRGPPVSCIKR |
| 2 | Human lactoferrin | MKLVFLVLLFLGALGLCLAGRRRRSVQWCAVSQPEATKCFQWQRNMRRVRGPPVSCIKRDSPIQCIQAIAENRADAVTLDGGFIYEAGLAPYKLRPVAAEVYGTERQPRTHYYAVAVVKKGGSFQLNELQGLKSCHTGLRRNAGWNVPIGTLRPFLNWTGPPEPIEAAVARFFSASCVPGADKGQFPNLCRLCAGTGENKCAFSSQEPYFSYSGAFKCLRDGAGDVAFIRESTVFEDLSDEAERDEYELLCPDNTRKPVDKFKDCHLARVPSHAVVARSVNGKEDAIWNLLRQAQEKFGKDKSPKFQLFGSPSGQKDLLFKDSAIGFSRVPPRIDSGLYLGSGYFTAIQNLRKSEEEVAARRARVVWCAVGEQELRKCNQWSGLSEGSVTCSSASTTEDCIALVLKGEADAMSLDGGYVYTAGKCGLVPVLAENYKSQQSSDPDPNCVDRPVEGYLAVAVVRRSDTSLTWNSVKGKKSCHTAVDRTAGWNIPMGLLFNQTGSCKFDEYFSQSCAPGSDPRSNLCALCIGDEQGENKCVPNSNERYYGYTGAFRCLAEDAGDVAFVKGVTVLQNTDGNNNEAWAKDLKLADFALLCLDGKRKPVTEARSCHLAMAPNHAVVSRMDKVERLKQVLLHQQAKFGRNGSDCPDKFCLFQSETKNLLFNDNTECLARLHGKTTYEKYLGPQYVAGITNLKKCSTSPLLEACEFLRK |
| 3 | S413-PV | ALWKTLLKKVLKAPKKKRKV |
| 4 | CecroA + Mel | KWKLFKKIGIGAVLKVLTTGLPALIS |
| 5 | Buforin 2 | TRSSRAGLQFPVGRVHRLLRK |
| 6 | Magainin | GIGKWLHSAKKFGKAFVGEIMNS |
| 7 | Pep1 | KETWWETWWTEWSQPKKKRKV |
| 8 | Melittin | GIGAVLKVLTTGLPALISWIKRKRQQ |
| 9 | GALA | WEAALAEALAEALAEHLAEALAEALEALAA |
| 10 | Apidaecins | GNNRPVYIPQPRPPHPRL |
| 11 | Tat | YGRKKRRQRRRG |
| 12 | KFFKFFKFFK | KFFKFFKFFK |
| 13 | YTA4 | IAWVKAFIRKLRKGPLG |
| 14 | M918 | MVTVLFRRLRIRRACGPPRVRV |
| 15 | Penetratin | RQIKIWFQNRRMKWKK |
| 16 | VP22 | NAATATRGRSAASRPTQRPRAPARSASRPRRPVQ |
| 17 | HGP | LLGRRGWEVLKYWWNLLQYWSQEL |
| 18 | Bac7 | RRIRPRPPRLPRPRPRPLPFPRPG |

Sequence Summary

| SEQ ID NO | Description | Sequence |
|---|---|---|
| 19 | 6R | RRRRRR |
| 20 | HuT-cell CPP | YARVRRRGPRGYARVRRRGPRR |
| 21 | pVEC | LLIILRRRIRKQAHAHSK |
| 22 | CADY | GLWRALWRLLRSLWRLLWRA |
| 23 | MAP | KLALKLALKALKAALKLA |
| 24 | LBU1 | RVVRVVRRVVRR |
| 25 | WLBU1 | RVVRVVRRWVRR |
| 26 | LBU2 | RRVVRRVRRVVRRVVRVVRRVVRR |
| 27 | WLBU2 | RRWVRRVRRWVRRVVRVVRRWVRR |
| 28 | P9b | QRKLAAKLT |
| 29 | P9b-WLBU2 tandem peptide | QRKLAAKLTRRWVRRVRRWVRRVVRVVRRWVRR |
| 30 | (KLAKLAK)$_2$ | KLAKLAKKLAKLAK |
| 31 | (KLAKKLA)$_2$ | KLAKKLAKLAKKLA |
| 32 | (KAAKKAA)$_2$ | KAAKKAAKAAKKAA |
| 33 | (KLGKKLG)$_3$ | KLGKKLGKLGKKLGKLGKKLG |
| 34 | $_D$(KLAKLAK)$_2$ | $_DK_DL_DA_DK_DL_DA_DK_DK_DL_DA_DK_DL_DA_DK$ |
| 35 | General formula of synthetic antimicrobial peptide | $[(X_1X_2X_2)(X_1X_2X_2)X_1]_n$ |
| 36 | General formula of synthetic antimicrobial peptide | $[(X_1X_2X_2)X_1(X_1X_2X_2)]_n$ |

We claim:

1. A composition comprising an amount of an antibacterial construct effective to inhibit a gram negative bacterium in a subject and a pharmaceutically acceptable carrier, wherein the antibacterial construct comprises human lactoferrin or a human lactoferrin derived peptide coupled to an antibacterial agent, wherein the antibacterial agent is an amphipathic α-helical peptide comprising a sequence selected from the group consisting of SEQ ID NO: 35 and SEQ ID NO: 36, and wherein the composition is selective for the bacterium and has low mammalian cell toxicity.

2. The composition of claim 1, wherein the gram negative bacterium is a member of *Pseudomonas* or wherein the gram-negative bacterium is *P. aeruginosa*.

3. The composition of claim 1, which further inhibits a gram positive bacterium.

4. The composition of claim 1, wherein the antibacterial agent is covalently coupled to human lactoferrin or the human lactoferrin derived peptide.

5. The composition of claim 1, wherein the antibacterial construct comprises the human lactoferrin derived peptide.

6. The composition of claim 5, wherein the human lactoferrin derived peptide comprises the amino acid sequence set forth in SEQ ID NO: 1.

7. The composition of claim 1, wherein the peptide comprises a sequence selected from the group consisting of: $(KLAKLAK)_2$ (SEQ ID NO: 30), $(KLAKKLA)_2$ (SEQ ID NO: 31), $(KAAKKAA)_2$ (SEQ ID NO: 32), or $(KLGKKLG)_3$ (SEQ ID NO: 33).

8. The composition of claim 7, wherein the peptide comprises D-amino acids.

9. The composition of claim 8, wherein the peptide comprises the sequence $_D(KLAKLAK)_2$ (SEQ ID NO: 34).

10. The composition of claim 1, wherein the antibacterial construct further comprises a targeting moiety.

11. The composition of claim 10, wherein the targeting moiety is a microbe specific targeting moiety that targets a gram negative bacterium.

12. The composition of claim 11, wherein the gram negative bacterium is a member of *Pseudomonas* or wherein the gram negative bacterium is *P. aeruginosa*.

13. The composition of claim 12, wherein the microbe specific targeting moiety is a peptide.

14. The composition of claim 1, wherein the minimal inhibitory concentration (MIC) of the antibacterial construct is less than 5 μM.

15. The composition of claim 1, wherein the MIC of the antibacterial construct is less than 1 μM.

16. A method of treating a *Pseudomonas* infection in a subject in need thereof, comprising administering a therapeutically effective amount of the composition of claim 1.

17. A method of prolonging survival of a subject in need thereof with a *Pseudomonas* infection, comprising administering a therapeutically effective amount of the composition of claim 1.

18. The method of claim 17, wherein the *Pseudomonas* infection is a *P. aeruginosa* infection.

19. A method of inducing selective toxicity in vivo in *Pseudomonas*, comprising administering to a subject in need thereof an effective amount of the composition of claim 1, thereby inducing toxicity in the *Pseudomonas*.

\* \* \* \* \*